(12) United States Patent
Los et al.

(10) Patent No.: US 8,802,415 B2
(45) Date of Patent: Aug. 12, 2014

(54) TALAROMYCES TRANSFORMANTS

(75) Inventors: Alrik Pieter Los, The Hague (NL);
Brenda Vonk, Spijkenisse (NL); Marco Alexander Van Den Berg, Poeldijk (NL); Robbertus Antonius Damveld, Berkel en Rodenrijs (NL); Cornelis Maria Jacobus Sagt, Utrecht (NL); Adrianus Wilhelmus Hermanus Vollebregt, Naaldwijk (NL); Margot Elisabeth Francoise Schooneveld-Bergmans, Delft (NL)

(73) Assignee: DSM IP Assets B.V., Heerlen (NL)

( * ) Notice: Subject to any disclaimer, the term of this patent is extended or adjusted under 35 U.S.C. 154(b) by 138 days.

(21) Appl. No.: 13/505,697

(22) PCT Filed: Nov. 4, 2010

(86) PCT No.: PCT/EP2010/066796
§ 371 (c)(1),
(2), (4) Date: Jul. 16, 2012

(87) PCT Pub. No.: WO2011/054899
PCT Pub. Date: May 12, 2011

(65) Prior Publication Data
US 2012/0276567 A1    Nov. 1, 2012

(30) Foreign Application Priority Data

Nov. 4, 2009  (EP) .................................... 09174990

(51) Int. Cl.
*C12N 9/42*  (2006.01)
*C12P 19/14*  (2006.01)
*C12N 15/80* (2006.01)
*C12N 9/24*  (2006.01)
*C12P 21/02* (2006.01)

(52) U.S. Cl.
CPC .............. *C12N 15/80* (2013.01); *C12N 9/2477* (2013.01); *Y02E 50/343* (2013.01); *C12Y 302/01004* (2013.01); *C12Y 302/01091* (2013.01); *C12N 9/2445* (2013.01); *C12P 21/02* (2013.01); *C12Y 302/01021* (2013.01); *C12N 9/2437* (2013.01)
USPC ........................................... 435/203; 435/183

(58) Field of Classification Search
CPC .......... C12N 9/2437; C12N 9/42; C12P 19/14
USPC .................................................. 435/183, 203
See application file for complete search history.

(56) References Cited

U.S. PATENT DOCUMENTS

| 7,514,110 B1 | 4/2009 | Van Den Hombergh et al. |
| 2008/0274886 A1 | 11/2008 | Van Den Homberg et al. |

FOREIGN PATENT DOCUMENTS

| WO | 01/70998 | 9/2001 |
| WO | 02/24926 | 3/2002 |
| WO | 2007/091231 | 8/2007 |

OTHER PUBLICATIONS

International Search Report for PCT/EP2010/066796 mailed Jan. 3, 2011.
Murray et al., "Isolation of the Glucose Ixidase Gene From Talaromyces Flavus and Characterisation of Its Role in the Biocontrol of Verticillium Dahliae," Current Genetics, vol. 32, No. 5, pp. 367-375, (Nov. 1, 1997).
Karlsson et al., "Homologous Expression and Characterization of CeL61A (EG IV) of *Trichoderma reesei*," European Journal of Biochemistry, vol. 268, No. 24, pp. 6498-6507, (Dec. 1, 2001).
Murray et al., "Expreaaion in *Trichoderma reesei* and Characterisation of a Thermostable Family 3 Beta-Glucosidase From the Moderately Thermophilic Fungus *Talaromyces emersonii*," Protein Expression and Purification, vol. 38, No. 2, pp. 248-257, (Dec. 1, 2004).

*Primary Examiner* — Karen Cochrane Carlson
(74) *Attorney, Agent, or Firm* — Miles & Stockbridge, P.C.

(57) ABSTRACT

The invention relates to a *Talaromyces* transformant comprising one or more recombinant gene, capable of producing cellulase in the absence of cellulase inducer in a glucose medium, having a cellulase activity of 2 WSU/ml or more, in 16 times or more diluted supernatant or broth.

17 Claims, 12 Drawing Sheets

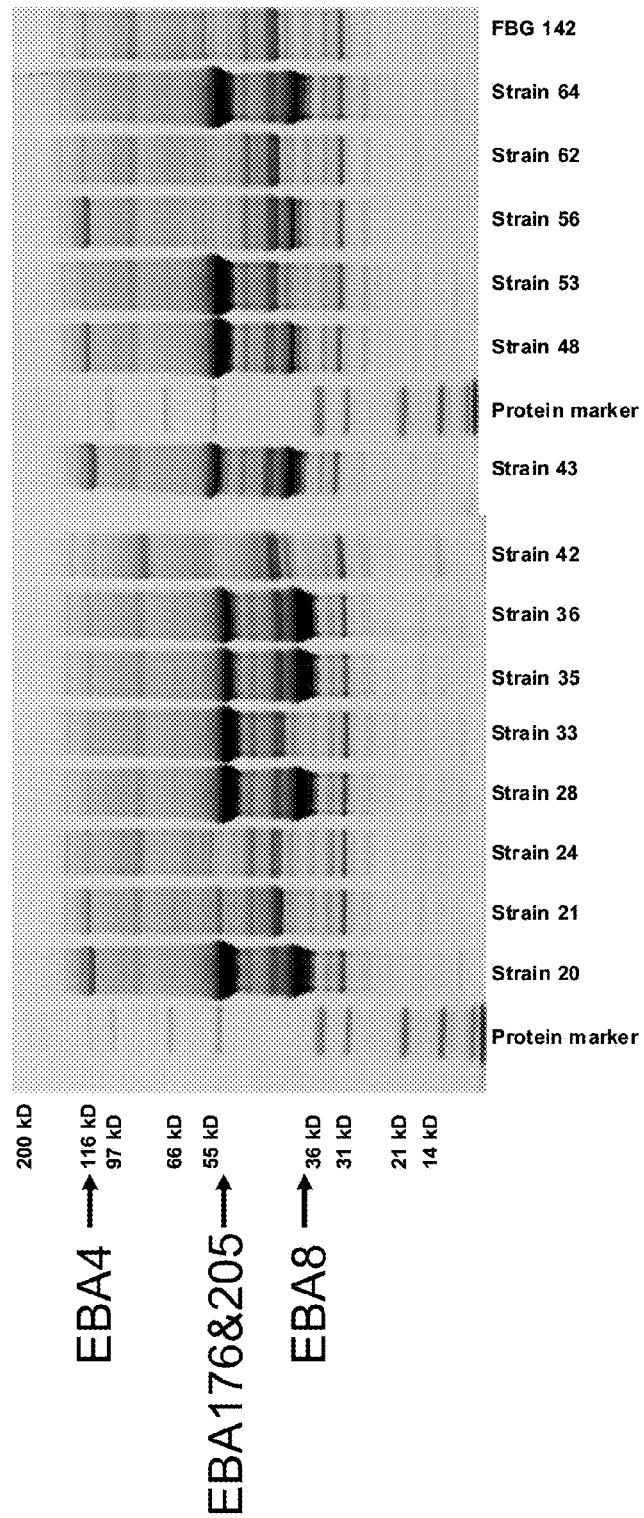

```
                           SEQUENCE LISTING

<160> NUMBER OF SEQ ID NOS: 25

<210> SEQ ID NO 1
<211> LENGTH: 22
<212> TYPE: DNA
<213> ORGANISM: Artificial Sequence
<220> FEATURE:
<223> OTHER INFORMATION: Synthetic DNA

<400> SEQUENCE: 1
tatgcagtgc tgccataacc at                                              22

<210> SEQ ID NO 2
<211> LENGTH: 22
<212> TYPE: DNA
<213> ORGANISM: Artificial Sequence
<220> FEATURE:
<223> OTHER INFORMATION: Synthetic DNA

<400> SEQUENCE: 2
gcagaagtgg tcctgcaact tt                                              22

<210> SEQ ID NO 3
<211> LENGTH: 422
<212> TYPE: PRT
<213> ORGANISM: Talaromyces emersonii
<220> FEATURE:
<221> NAME/KEY: MISC_FEATURE
<222> LOCATION: (1)..(422)
<223> OTHER INFORMATION: FLAG-tagged T. emersonii Beta-glucanase CEB
<220> FEATURE:
<221> NAME/KEY: MISC_FEATURE
<222> LOCATION: (415)..(422)
<223> OTHER INFORMATION: C-terminal FLAG-tag

<400> SEQUENCE: 3

Met Asp Arg Ile Leu Ala Leu Ile Leu Val Pro Leu Ala Thr Val Thr
1               5                   10                  15

Ala Gln Gln Ile Gly Thr Ile Pro Glu Val His Pro Lys Leu Pro Thr
            20                  25                  30

Trp Lys Cys Thr Thr Glu Gly Gly Cys Val Gln Asn Thr Ser Val
        35                  40                  45

Val Leu Glu Tyr Leu Ser His Pro Ile His Glu Val Gly Asn Ser Asp
    50                  55                  60

Val Ser Cys Val Val Ser Gly Gly Leu Asn Gln Ser Leu Cys Pro Asn
65                  70                  75                  80

Glu Glu Glu Cys Ser Lys Asn Cys Val Val Glu Gly Ala Asn Tyr Thr
                85                  90                  95

Ser Ser Gly Val His Thr Asp Gly Asp Ala Leu Thr Leu Asn Gln Tyr
            100                 105                 110

Val Thr Asn Gly Asp Gln Val Val Thr Ala Ser Pro Arg Val Tyr Leu
        115                 120                 125

Leu Ala Ser Asp Asp Glu Asp Gly Asn Tyr Ser Met Leu Gln Leu Leu
    130                 135                 140

Gly Gln Glu Leu Ser Phe Asp Val Asp Val Ser Lys Leu Val Cys Gly
145                 150                 155                 160

Met Asn Gly Ala Leu Tyr Leu Ser Glu Met Asp Ala Ser Gly Gly Arg
                165                 170                 175
```

-continued

```
Asn Ser Leu Asn Pro Ala Gly Ala Gln Tyr Gly Ser Gly Tyr Cys Asp
            180                 185                 190

Ala Gln Cys Gly Val Gln Pro Phe Ile Asn Gly Thr Val Asn Thr Gly
            195                 200                 205

Ser Leu Gly Ala Cys Cys Asn Glu Met Asp Ile Trp Glu Ala Asn Ala
210                 215                 220

Leu Ala Thr Ala Leu Thr Pro His Pro Cys Ser Val Thr Ser Ile Tyr
225                 230                 235                 240

Ala Cys Ser Gly Ala Glu Cys Gly Ser Asn Gly Val Cys Asp Lys Pro
                245                 250                 255

Gly Cys Gly Tyr Asn Pro Tyr Ala Leu Gly Asp His Asn Tyr Tyr Gly
            260                 265                 270

Pro Gly Lys Thr Val Asp Thr Ser Arg Pro Phe Thr Val Val Thr Gln
            275                 280                 285

Phe Leu Thr Asn Asp Asn Thr Thr Gly Thr Leu Thr Glu Ile Arg
            290                 295                 300

Arg Leu Tyr Val Gln Asp Gly Asn Val Ile Gly Pro Ser Pro Ser Asp
305                 310                 315                 320

Ser Val Ser Ser Ile Thr Asp Ser Phe Cys Ser Thr Val Asp Ser Tyr
                325                 330                 335

Phe Glu Pro Leu Gly Gly Leu Lys Glu Met Gly Glu Ala Leu Gly Arg
            340                 345                 350

Gly Met Val Leu Val Phe Ser Ile Trp Asn Asp Pro Gly Gln Phe Met
            355                 360                 365

Asn Trp Leu Asp Ser Gly Asn Ala Gly Pro Cys Asn Ser Thr Glu Gly
370                 375                 380

Asn Pro Ala Thr Ile Glu Ala Gln His Pro Asp Thr Ala Val Thr Phe
385                 390                 395                 400

Ser Asn Ile Arg Trp Gly Asp Ile Gly Ser Thr Phe Gln Ser Asp Tyr
                405                 410                 415

Lys Asp Asp Asp Asp Lys
            420
```

<210> SEQ ID NO 4
<211> LENGTH: 1269
<212> TYPE: DNA
<213> ORGANISM: talaromyces emersonii
<220> FEATURE:
<221> NAME/KEY: misc_feature
<222> LOCATION: (1)..(1269)
<223> OTHER INFORMATION: FLAG-tagged T. emersonii Beta-glucanase CEB
      (DNA, coding region)
<220> FEATURE:
<221> NAME/KEY: misc_feature
<222> LOCATION: (1243)..(1266)
<223> OTHER INFORMATION: C-terminal FLAG-tag

<400> SEQUENCE: 4

```
atggaccgta tactagctct gatcctggtt cctctggcca ctgtcactgc tcagcagatc      60
ggtaccatcc ccgaggtcca ccccaagctc cccacctgga agtgcaccac tgagggtgga     120
tgtgtccagc agaacacctc cgtcgtcctc gagtacctgt ctcacccat ccacgaggtt      180 ggcaactccg atgtcagctg tgttgtctcc ggtggtctga ccagtctct tgccccaac      240 gaagaagaat gctccaagaa ctgcgttgtt gagggtgcca actacacctc ctccggtgtc     300
cacaccgacg tgatgccct cacccctcaac cagtacgtca ccaacggtga ccaggttgtc    360
actgccagcc tcgtgtctcta cctccttgcc tccgacgacg aggatggcaa ctacagcatg    420
```

-continued

```
ctccagctcc ttggccagga gctttctttc gatgtcgatg tctccaagct cgtctgcggt    480
atgaacggtg ctctctacct ctccgagatg gatgccagcg gtggtcgcaa ctccctcaac    540
cctgctggtg ctcagtacgg ctctggctac tgcgatgccc agtgcggtgt ccagcccttc    600
atcaacggca ccgtcaacac tggctccctc ggtgcttgct gcaacgagat ggacatctgg    660
gaggccaacg cccttgccac tgctctgacc cccacccctt gctccgtcac ctccatctac    720
gcctgctctg gtgctgagtg cggttccaac ggtgtctgcg acaagcccgg ctgcggttac    780 aaccccctacg ctcttggtga ccacaactac tacggccccg gcaagaccgt tgacacttct    840
cgccccttca ccgttgtcac ccagttcctg accaacgaca caccaccac tggtacccctc    900 accgagatcc gccgtctgta cgtgcaggat ggcaacgtca ttggtccctc ccctccgac    960 agcgtttcct ccatcaccga ctctttctgc tccaccgttg acagctactt cgagcctctt   1020
ggtggtctga aggagatggg tgaggctctt ggccgtggta tggtcctggt gttctccatc   1080
tggaacgacc ccggccagtt catgaactgg ctcgactctg gcaacgccgg tccttgcaac   1140
agcactgagg gcaaccccgc caccattgag gctcagcacc ctgacactgc tgtcaccttc   1200
tccaacatcc gctggggtga cattggcagc accttccagt cagactacaa ggatgatgat   1260
gacaagtaa                                                           1269
```

<210> SEQ ID NO 5
<211> LENGTH: 35
<212> TYPE: DNA
<213> ORGANISM: Artificial Sequence
<220> FEATURE:
<223> OTHER INFORMATION: Synthetic DNA

<400> SEQUENCE: 5

```
cagcttaatt aacaccgtca aaatggaccg tatac                                35
```

<210> SEQ ID NO 6
<211> LENGTH: 58
<212> TYPE: DNA
<213> ORGANISM: Artificial Sequence
<220> FEATURE:
<223> OTHER INFORMATION: Synthetic DNA

<400> SEQUENCE: 6

```
ggcgcgcctt tacttgtcat catcatcctt gtagtctgac tggaaggtgc tgccaatg       58
```

<210> SEQ ID NO 7
<211> LENGTH: 892
<212> TYPE: DNA
<213> ORGANISM: Artificial Sequence
<220> FEATURE:
<223> OTHER INFORMATION: Synthetic DNA
<220> FEATURE:
<221> NAME/KEY: promoter
<222> LOCATION: (1)..(870)
<223> OTHER INFORMATION: gpd promoter
<220> FEATURE:
<221> NAME/KEY: misc_feature
<222> LOCATION: (871)..(882)
<223> OTHER INFORMATION: Restriction enzyme sites
<220> FEATURE:
<221> NAME/KEY: misc_feature
<222> LOCATION: (883)..(892)
<223> OTHER INFORMATION: Kozak sequence

<400> SEQUENCE: 7

```
cgagctctgt acagtgaccg gtgactcttt ctggcatgcg gagagacgga cggacgcaga     60
```

```
gagaagggct gagtaataag cgccactgcg ccagacagct ctggcggctc tgaggtgcag    120
tggatgatta ttaatccggg accggccgcc cctccgcccc gaagtggaaa ggctggtgtg    180
cccctcgttg accaagaatc tattgcatca tcggagaata tggagcttca tcgaatcacc    240
ggcagtaagc gaaggagaat gtgaagccag gggtgtatag ccgtcggcga aatagcatgc    300
cattaaccta ggtacagaag tccaattgct tccgatctgg taaaagattc acgagatagt    360
accttctccg aagtaggtag agcgagtacc cggcgcgtaa gctccctaat tggcccatcc    420
ggcatctgta gggcgtccaa atatcgtgcc tctcctgctt tgcccggtgt atgaaaccgg    480
aaaggccgct caggagctgg ccagcggcgc agaccgggaa cacaagctgg cagtcgaccc    540
atccggtgct ctgcactcga cctgctgagg tccctcagtc cctggtaggc agctttgccc    600
cgtctgtccg cccggtgtgt cggcggggtt gacaaggtcg ttgcgtcagt ccaacatttg    660
ttgccatatt ttcctgctct ccccaccagc tgctcttttc ttttctcttt cttttcccat    720
cttcagtata ttcatcttcc catccaagaa cctttatttc ccctaagtaa gtactttgct    780
acatccatac tccatccttc ccatccctta ttcctttgaa cctttcagtt cgagctttcc    840
cacttcatcg cagcttgact aacagctacc aagcttaatt aacaccgtca aa            892

<210> SEQ ID NO 8
<211> LENGTH: 23
<212> TYPE: DNA
<213> ORGANISM: Artificial Sequence
<220> FEATURE:
<223> OTHER INFORMATION: Synthetic DNA

<400> SEQUENCE: 8
ccaccttcaa ctccatcatg aag                                             23

<210> SEQ ID NO 9
<211> LENGTH: 20
<212> TYPE: DNA
<213> ORGANISM: Artificial Sequence
<220> FEATURE:
<223> OTHER INFORMATION: Synthetic DNA

<400> SEQUENCE: 9
ttagaagcac ttgcggtgga                                                 20

<210> SEQ ID NO 10
<211> LENGTH: 455
<212> TYPE: PRT
<213> ORGANISM: Talaromyces emersonii
<220> FEATURE:
<221> NAME/KEY: MISC_FEATURE
<222> LOCATION: (1)..(455)
<223> OTHER INFORMATION: T. emersonii cellobiohydrolase I

<400> SEQUENCE: 10
```

Met Leu Arg Arg Ala Leu Leu Ser Ser Ala Ile Leu Ala Val
1               5                   10                  15

Lys Ala Gln Gln Ala Gly Thr Ala Thr Ala Glu Asn His Pro Pro Leu
            20                  25                  30

Thr Trp Gln Glu Cys Thr Ala Pro Gly Ser Cys Thr Thr Gln Asn Gly
        35                  40                  45

Ala Val Val Leu Asp Ser Asn Trp Arg Trp Val His Asn Val Gly Gly
    50                  55                  60

Tyr Thr Asn Cys Tyr Thr Gly Asn Thr Trp Asn Pro Thr Tyr Cys Pro
65                  70                  75                  80

Asp Asp Val Thr Cys Ala Glu Asn Cys Ala Leu Asp Gly Ala Asp Tyr
            85                  90                  95

Glu Gly Thr Tyr Gly Val Thr Ser Ser Gly Ser Glu Leu Arg Leu Asn
            100                 105                 110

Phe Val Thr Gly Ser Asn Val Gly Ser Arg Leu Tyr Leu Leu Gln Asp
            115                 120                 125

Asp Glu Thr Tyr Gln Ile Phe Lys Leu Leu Asn Arg Glu Phe Thr Phe
            130                 135                 140

Asp Val Asp Val Ser Asn Leu Pro Cys Gly Leu Asn Gly Ala Leu Tyr
145                 150                 155                 160

Phe Val Ala Met Asp Ala Asp Gly Gly Val Ser Lys Tyr Pro Asn Asn
                165                 170                 175

Lys Ala Gly Ala Lys Tyr Gly Thr Gly Tyr Cys Asp Ser Gln Cys Pro
            180                 185                 190

Arg Asp Leu Lys Phe Ile Asp Gly Glu Gly Asn Val Glu Gly Trp Gln
            195                 200                 205

Pro Ser Ser Asn Asn Ala Asn Thr Gly Ile Gly Asp His Gly Ser Cys
            210                 215                 220

Cys Ala Glu Met Asp Val Trp Glu Ala Asn Ser Ile Ser Asn Ala Val
225                 230                 235                 240

Thr Pro His Pro Cys Asp Thr Pro Gly Gln Thr Met Cys Asp Gly Asp
                245                 250                 255

Asp Cys Gly Gly Thr Tyr Ser Thr Asn Arg Tyr Ala Gly Glu Cys Asp
            260                 265                 270

Pro Asp Gly Cys Asp Phe Asn Pro Tyr Arg Met Gly Asn Thr Ser Phe
            275                 280                 285

Tyr Gly Pro Gly Lys Ile Ile Asp Thr Thr Gln Pro Phe Thr Val Val
            290                 295                 300

Thr Gln Phe Leu Thr Asp Asp Gly Thr Asp Thr Gly Thr Leu Ser Glu
305                 310                 315                 320

Ile Lys Arg Phe Tyr Ile Gln Asn Gly Lys Val Ile Pro Gln Pro Asn
                325                 330                 335

Ser Asp Ile Ser Gly Val Thr Gly Asn Ser Ile Thr Thr Glu Phe Cys
            340                 345                 350

Thr Ala Gln Lys Gln Ala Phe Gly Asp Thr Asp Phe Ser Gln His
            355                 360                 365

Gly Gly Leu Ala Lys Met Gly Ala Ala Met Gln Gln Gly Met Val Leu
            370                 375                 380

Val Met Ser Leu Trp Asp Asp Tyr Ala Ala Gln Met Leu Trp Leu Asp
385                 390                 395                 400

Ser Asp Tyr Pro Thr Asn Ala Ser Ala Thr Thr Pro Gly Val Ala Arg
                405                 410                 415

Gly Thr Cys Pro Thr Asp Ser Gly Val Pro Ser Gln Val Glu Ser Gln
            420                 425                 430

Ser Pro Asn Ser Tyr Val Thr Tyr Ser Asn Ile Lys Phe Gly Pro Ile
            435                 440                 445

Asn Ser Thr Phe Thr Ala Ser
    450                 455

<210> SEQ ID NO 11
<211> LENGTH: 1368
<212> TYPE: DNA
<213> ORGANISM: Artificial Sequence
<220> FEATURE:
<223> OTHER INFORMATION: T. emersonii CBHI (DNA, coding region)

<400> SEQUENCE: 11

```
atgctccgcc gtgctcttct gctgagcagc tctgccatcc tggccgtcaa ggcccagcag      60
gctggtactg ccactgctga gaaccaccct cccttgacct ggcaggagtg cactgctcct     120
ggttcctgca ccactcagaa cggtgctgtt gtccttgaca gcaactggag atgggttcac     180
aacgtcggtg gttacaccaa ctgctacact ggcaacacct ggaaccccac ctactgcccc     240
gatgatgtca cctgcgctga aactgcgct cttgacggtg ccgactacga gggtacctac     300
ggtgtcactt cttctggctc tgagctccgt ctgaacttcg tcaccggcag caacgtcggc     360
tctcgtctct acctcctcca ggatgacgag acctaccaga tcttcaagct cctcaaccgt     420
gagttcacct tcgatgttga tgtctccaac cttccttgcg gtctgaacgg tgctctgtac     480
ttcgtcgcca tggatgccga cggtggtgtc tccaagtacc ccaacaacaa ggccggtgcc     540
aagtacggta ctggctactg cgacagccag tgccccgtg acctcaagtt cattgacggc     600
gagggcaacg tcgagggctg gcagccctcc tccaacaacg ccaacactgg tatcggtgac     660
cacggctctt gctgcgctga gatggatgtc tgggaggcca actccatctc caacgccgtc     720
accccccacc cttgcgacac ccccggccag accatgtgcg atggtgatga ctgcggtggt     780
acctactcca ccaaccgcta cgccggtgag tgcgaccccg atggctgcga cttcaacccc     840
taccgcatgg gcaacacctc cttctacggc cctggcaaga tcattgacac cacccagccc     900
ttcaccgttg tcacccagtt cctgaccgat gacggcaccg acactggtac cctctccgag     960
atcaagcgct tctacatcca gaacggcaag gtcatccccc agcccaactc cgacatctcc    1020
ggtgtcaccg gcaactccat caccactgag ttctgcactg ctcagaagca ggctttcggt    1080
gacaccgatg acttctccca gcacggtggt cttgccaaga tgggtgctgc catgcagcag    1140
ggtatggtcc tggtcatgtc cctctgggat gactacgctg ctcagatgct ctggctcgac    1200
tccgactacc ccaccaacgc ctccgccacc actcctggtg ttgctcgtgg tacctgcccc    1260
accgactctg gtgttcctag ccaggttgag agccagtccc ccaactccta cgtgacctac    1320
tccaacatca agttcggtcc catcaactcc accttcactg catcgtaa              1368
```

<210> SEQ ID NO 12
<211> LENGTH: 335
<212> TYPE: PRT
<213> ORGANISM: Talaromyces emersonii
<220> FEATURE:
<221> NAME/KEY: MISC_FEATURE
<222> LOCATION: (1)..(335)
<223> OTHER INFORMATION: T. emersonii Beta-glucanase CEA

<400> SEQUENCE: 12

```
Met Lys Phe Ser Arg Val Val Cys Gly Leu Thr Ala Ala Gly Gly Ala
1               5                   10                  15

Leu Ala Ala Pro Val Lys Glu Lys Gly Ile Lys Lys Arg Ala Ser Pro
                20                  25                  30

Phe Gln Trp Phe Gly Ser Asn Glu Ser Gly Ala Glu Phe Gly Asn Asn
            35                  40                  45

Asn Ile Pro Gly Val Glu Gly Thr Asp Tyr Thr Phe Pro Asn Thr Ser
        50                  55                  60

Ala Ile Gln Ile Leu Ile Asp Gln Gly Met Asn Ile Phe Arg Val Pro
65                  70                  75                  80

Phe Leu Met Glu Arg Met Val Pro Asn Gln Met Thr Gly Pro Val Asp
                85                  90                  95
```

Ser Ala Tyr Phe Gln Gly Tyr Ser Gln Val Ile Asn Tyr Ile Thr Ser
                100                 105                 110

His Gly Ala Ser Ala Val Ile Asp Pro His Asn Phe Gly Arg Tyr Tyr
            115                 120                 125

Asn Asn Ile Ile Ser Ser Pro Ser Asp Phe Gln Thr Phe Trp His Thr
130                 135                 140

Ile Ala Ser Asn Phe Ala Asp Asn Asp Asn Val Ile Phe Asp Thr Asn
145                 150                 155                 160

Asn Glu Tyr His Asp Met Asp Glu Ser Leu Val Val Gln Leu Asn Gln
                165                 170                 175

Ala Ala Ile Asp Gly Ile Arg Ala Ala Gly Ala Thr Ser Gln Tyr Ile
            180                 185                 190

Phe Val Glu Gly Asn Ser Trp Thr Gly Ala Trp Thr Trp Thr Gln Val
        195                 200                 205

Asn Asp Ala Met Ala Asn Leu Thr Asp Pro Gln Asn Lys Ile Val Tyr
210                 215                 220

Glu Met His Gln Tyr Leu Asp Ser Asp Gly Ser Gly Thr Ser Asp Gln
225                 230                 235                 240

Cys Val Asn Ser Thr Ile Gly Gln Asp Arg Val Glu Ser Ala Thr Ala
                245                 250                 255

Trp Leu Lys Gln Asn Gly Lys Lys Ala Ile Leu Gly Glu Tyr Ala Gly
            260                 265                 270

Gly Ala Asn Ser Val Cys Glu Thr Ala Val Thr Gly Met Leu Asp Tyr
        275                 280                 285

Leu Ala Asn Asn Thr Asp Val Trp Thr Gly Ala Ile Trp Trp Ala Ala
290                 295                 300

Gly Pro Trp Trp Gly Asp Tyr Ile Phe Ser Met Glu Pro Pro Ser Gly
305                 310                 315                 320

Ile Ala Tyr Glu Gln Val Leu Pro Leu Leu Lys Pro Tyr Leu Glu
                325                 330                 335

<210> SEQ ID NO 13
<211> LENGTH: 1008
<212> TYPE: DNA
<213> ORGANISM: Artificial Sequence
<220> FEATURE:
<223> OTHER INFORMATION: T. emersonii beta-glucanase CEA (DNA, coding
      region)

<400> SEQUENCE: 13
atgaagttct ctcgtgttgt ctgcggtctg accgctgctg gtggtgctct tgctgctcct      60
gtcaaggaga agggtatcaa gaagcgtgcc tccccttcc agtggttcgg ttccaacgag      120
agcggtgctg agttcggcaa caacaacatc cccggtgttg agggtaccga ctacaccttc      180
cccaacactt ctgccatcca gatcctgatt gaccagggca tgaacatctt ccgtgtcccc      240
ttcctgatgg agcgcatggt tcccaaccag atgactggtc tgttgactc tgcctacttc      300 cagggctact ctcaggtcat caactacatc acctcccacg gtgcctccgc cgtcattgac      360
cctcacaact tcggccgcta ctacaacaac atcatctcct cccccctccga cttccagacc      420 ttctggcaca ccattgcctc caacttcgcc gacaacgaca cgtcatctt cgacaccaac      480 aacgagtacc acgacatgga tgagagcttg gttgtccagc tcaaccaggc tgccattgat      540
ggtatccgtg ctgctggtgc caccagccag tacatcttcg tcgagggcaa cagctggact      600 ggtgctgga cctggaccca ggtcaacgat gccatggcca actgaccga cccccagaac      660 aagatcgtct acgagatgca ccagtacctc gactccgacg gcagcggtac ctccgaccag      720

-continued

```
tgcgtcaact ccaccattgg ccaggaccgt gttgagtctg ccactgcctg gctcaagcag    780
aacggcaaga aggccatcct gggtgaatac gctggtggtg ccaactccgt ctgcgagact    840
gctgtcaccg gcatgcttga ctacctcgcc aacaacaccg atgtctggac tggtgccatc    900
tggtgggctg ctggtccctg gtggggtgac tacatcttct ccatggagcc tcctccggc    960 attgcctacg agcaggtcct tcctctcctc aagccctacc tcgaataa              1008
```

<210> SEQ ID NO 14
<211> LENGTH: 857
<212> TYPE: PRT
<213> ORGANISM: Talaromyces emersonii
<220> FEATURE:
<221> NAME/KEY: MISC_FEATURE
<222> LOCATION: (1)..(857)
<223> OTHER INFORMATION: T. emersonii Beta-glucosidase

<400> SEQUENCE: 14

Met Arg Asn Gly Leu Leu Lys Val Ala Leu Ala Ala Ala Ser Ala
1               5                   10                  15

Val Asn Gly Glu Asn Leu Ala Tyr Ser Pro Pro Phe Tyr Pro Ser Pro
            20                  25                  30

Trp Ala Asn Gly Gln Gly Asp Trp Ala Glu Ala Tyr Gln Lys Ala Val
        35                  40                  45

Gln Phe Val Ser Gln Leu Thr Leu Ala Glu Lys Val Asn Leu Thr Thr
    50                  55                  60

Gly Thr Gly Trp Glu Gln Asp Arg Cys Val Gly Gln Val Gly Ser Ile
65                  70                  75                  80

Pro Arg Leu Gly Phe Pro Gly Leu Cys Met Gln Asp Ser Pro Leu Gly
                85                  90                  95

Val Arg Asp Thr Asp Tyr Asn Ser Ala Phe Pro Ala Gly Val Asn Val
            100                 105                 110

Ala Ala Thr Trp Asp Arg Asn Leu Ala Tyr Arg Arg Gly Val Ala Met
        115                 120                 125

Gly Glu Glu His Arg Gly Lys Gly Val Asp Val Gln Leu Gly Pro Val
    130                 135                 140

Ala Gly Pro Leu Gly Arg Ser Pro Asp Ala Gly Arg Asn Trp Glu Gly
145                 150                 155                 160

Phe Ala Pro Asp Pro Val Leu Thr Gly Asn Met Met Ala Ser Thr Ile
                165                 170                 175

Gln Gly Ile Gln Asp Ala Gly Val Ile Ala Cys Ala Lys His Phe Ile
            180                 185                 190

Leu Tyr Glu Gln Glu His Phe Arg Gln Gly Ala Gln Asp Gly Tyr Asp
        195                 200                 205

Ile Ser Asp Ser Ile Ser Ala Asn Ala Asp Asp Lys Thr Met His Glu
    210                 215                 220

Leu Tyr Leu Trp Pro Phe Ala Asp Ala Val Arg Ala Gly Val Gly Ser
225                 230                 235                 240

Val Met Cys Ser Tyr Asn Gln Val Asn Asn Ser Tyr Ala Cys Ser Asn
                245                 250                 255

Ser Tyr Thr Met Asn Lys Leu Leu Lys Ser Glu Leu Gly Phe Gln Gly
            260                 265                 270

Phe Val Met Thr Asp Trp Gly Gly His His Ser Gly Val Gly Ser Ala
        275                 280                 285

Leu Ala Gly Leu Asp Met Ser Met Pro Gly Asp Ile Ala Phe Asp Ser
    290                 295                 300

```
Gly Thr Ser Phe Trp Gly Thr Asn Leu Thr Val Ala Val Leu Asn Gly
305                 310                 315                 320

Ser Ile Pro Glu Trp Arg Val Asp Asp Met Ala Val Arg Ile Met Ser
                325                 330                 335

Ala Tyr Tyr Lys Val Gly Arg Asp Arg Tyr Ser Val Pro Ile Asn Phe
            340                 345                 350

Asp Ser Trp Thr Leu Asp Thr Tyr Gly Pro Glu His Tyr Ala Val Gly
        355                 360                 365

Gln Gly Gln Thr Lys Ile Asn Glu His Val Asp Val Arg Gly Asn His
    370                 375                 380

Ala Glu Ile Ile His Glu Ile Gly Ala Ala Ser Ala Val Leu Leu Lys
385                 390                 395                 400

Asn Lys Gly Gly Leu Pro Leu Thr Gly Thr Glu Arg Phe Val Gly Val
                405                 410                 415

Phe Gly Lys Asp Ala Gly Ser Asn Pro Trp Gly Val Asn Gly Cys Ser
            420                 425                 430

Asp Arg Gly Cys Asp Asn Gly Thr Leu Ala Met Gly Trp Gly Ser Gly
        435                 440                 445

Thr Ala Asn Phe Pro Tyr Leu Val Thr Pro Gln Ala Ile Gln Arg
450                 455                 460

Glu Val Leu Ser Arg Asn Gly Thr Phe Thr Gly Ile Thr Asp Asn Gly
465                 470                 475                 480

Ala Leu Ala Glu Met Ala Ala Ala Ser Gln Ala Asp Thr Cys Leu
                485                 490                 495

Val Phe Ala Asn Ala Asp Ser Gly Glu Gly Tyr Ile Thr Val Asp Gly
                500                 505                 510

Asn Glu Gly Asp Arg Lys Asn Leu Thr Leu Trp Gln Gly Ala Asp Gln
                515                 520                 525

Val Ile His Asn Val Ser Ala Asn Cys Asn Asn Thr Val Val Leu
    530                 535                 540

His Thr Val Gly Pro Val Leu Ile Asp Asp Trp Tyr Asp His Pro Asn
545                 550                 555                 560

Val Thr Ala Ile Leu Trp Ala Gly Leu Pro Gly Gln Glu Ser Gly Asn
                565                 570                 575

Ser Leu Val Asp Val Leu Tyr Gly Arg Val Asn Pro Gly Lys Thr Pro
            580                 585                 590

Phe Thr Trp Gly Arg Ala Arg Asp Asp Tyr Gly Ala Pro Leu Ile Val
        595                 600                 605

Lys Pro Asn Asn Gly Lys Gly Ala Pro Gln Gln Asp Phe Thr Glu Gly
    610                 615                 620

Ile Phe Ile Asp Tyr Arg Arg Phe Asp Lys Tyr Asn Ile Thr Pro Ile
625                 630                 635                 640

Tyr Glu Phe Gly Phe Gly Leu Ser Tyr Thr Thr Phe Glu Phe Ser Gln
                645                 650                 655

Leu Asn Val Gln Pro Ile Asn Ala Pro Pro Tyr Thr Pro Ala Ser Gly
            660                 665                 670

Phe Thr Lys Ala Ala Gln Ser Phe Gly Gln Pro Ser Asn Ala Ser Asp
        675                 680                 685

Asn Leu Tyr Pro Ser Asp Ile Glu Arg Val Pro Leu Tyr Ile Tyr Pro
    690                 695                 700

Trp Leu Asn Ser Thr Asp Leu Lys Ala Ser Ala Asn Asp Pro Asp Tyr
705                 710                 715                 720
```

Gly Leu Pro Thr Glu Lys Tyr Val Pro Pro Asn Ala Thr Asn Gly Asp
            725                 730                 735

Pro Gln Pro Ile Asp Pro Ala Gly Gly Ala Pro Gly Gly Asn Pro Ser
        740                 745                 750

Leu Tyr Glu Pro Val Ala Arg Val Thr Thr Ile Ile Thr Asn Thr Gly
    755                 760                 765

Lys Val Thr Gly Asp Glu Val Pro Gln Leu Tyr Val Ser Leu Gly Gly
770                 775                 780

Pro Asp Asp Ala Pro Lys Val Leu Arg Gly Phe Asp Arg Ile Thr Leu
785                 790                 795                 800

Ala Pro Gly Gln Gln Tyr Leu Trp Thr Thr Thr Leu Thr Arg Arg Asp
            805                 810                 815

Ile Ser Asn Trp Asp Pro Val Thr Gln Asn Trp Val Val Thr Asn Tyr
        820                 825                 830

Thr Lys Thr Ile Tyr Val Gly Asn Ser Ser Arg Asn Leu Pro Leu Gln
    835                 840                 845

Ala Pro Leu Lys Pro Tyr Pro Gly Ile
    850                 855

<210> SEQ ID NO 15
<211> LENGTH: 2574
<212> TYPE: DNA
<213> ORGANISM: Artificial Sequence
<220> FEATURE:
<223> OTHER INFORMATION: T. emersonii beta-glucosidase (DNA, coding
      region)

<400> SEQUENCE: 15

| | |
|---|---|
| atgcgcaacg gtctgctcaa ggttgctgct cttgctgctg cctccgccgt caacggcgag | 60 |
| aacctggcct actctcctcc cttctacccc tccccctggg ccaacggcca gggtgactgg | 120 |
| gctgaggcct accagaaggc cgtccagttc gtcagccagc tcaccctggc tgagaaggtc | 180 |
| aacctgacca ctggtactgg ctgggagcag accgctgcg ttggccaggt cggctccatc | 240 |
| ccccgtcttg gtttccccgg tctttgcatg caggactctc ctcttggtgt ccgtgacacc | 300 |
| gactacaact ctgctttccc tgctggtgtc aacgtcgctg ccacctggga ccgcaacctg | 360 |
| gcctaccgcc gtggtgttgc catgggtgag gagcaccgtg gcaagggtgt tgatgtccag | 420 |
| ctcggtcctg ttgctggtcc tctgggccgc tctcccgatg ctggccgcaa ctgggagggt | 480 |
| ttcgctcctg accccgtcct cactggtaac atgatggcct ccaccatcca gggtatccag | 540 |
| gatgctggtg tcattgcctg cgccaagcac ttcatcctgt acgagcagga gcacttccgc | 600 |
| cagggtgctc aggatggcta cgatatatct gactccatct ccgccaacgc cgatgacaag | 660 |
| accatgcacg agctctacct ctggcccttc gccgatgccg tccgtgctgg tgttggctcc | 720 |
| gtcatgtgct cctacaacca ggtcaacaac tcctacgcct gctccaacag ctacaccatg | 780 |
| aacaagctct tgaaatcaga gcttggtttc caggttttcg tcatgactga ctggggtggt | 840 |
| caccactctg tgttggttc cgctcttgct ggtcttgaca tgagcatgcc cggtgacatt | 900 |
| gctttcgact ccggtaccct cttctgggt accaacctga ccgttgccgt cctcaacggc | 960 |
| agcatccccg aatggcgtgt cgatgacatg gccgtccgta tcatgtctgc ctactacaag | 1020 |
| gtcggtcgtg accgctactc cgtccccatc aacttcgaca ctggaccct cgacacctac | 1080 |
| ggccctgagc actacgccgt cggccagggt cagaccaaga tcaacgagca cgttgatgtc | 1140 |
| cgtggcaacc acgctgagat catccacgag atcggtgctg cctccgccgt cctcctcaag | 1200 |
| aacaagggtg tcctgccctt gactggtact gagcgcttcg tcggtgtgtt cggcaaggat | 1260 |

```
gccggttcca acccctgggg tgtcaacggc tgctccgacc gtggctgcga caacggcacc   1320
ctcgccatgg gctggggcag cggtactgcc aacttcccct acctggtcac ccccgagcag   1380
gccatccagc gtgaggtcct ttctcgcaac ggcaccttca ctggtatcac cgacaacggt   1440
gctcttgctg agatggctgc tgctgcctcc caggccgaca cctgcctggt ctttgccaac   1500
gccgacagcg gtgagggcta catcaccgtt gacggcaacg agggtgaccg caagaacctg   1560
accctctggc agggtgccga ccaggtcatc cacaacgttt ccgccaactg caacaacact   1620
gttgttgtcc tccacaccgt cggtcctgtc ctgattgatg actggtacga ccaccccaac   1680
gtcactgcca tcctctgggc tggtctgccc ggtcaggagt ccggcaactc gctagttgat   1740
gtcctctacg gccgtgtcaa ccccggcaag actcccttca cctggggtcg tgctcgtgat   1800
gactacggtg ctcctctgat tgtcaagccc aacaacggca agggtgctcc tcagcaggac   1860
ttcaccgagg gtatcttcat tgactaccgc cgcttcgaca agtacaacat caccccccatc   1920
tacgagttcg gtttcggtct gagctacacc accttcgagt ctcccagct caacgtccag   1980
cccatcaacg ctcctcccta cactcccgcc tccggtttca ccaaggctgc tcagtccttc   2040
ggccagccct ccaacgcctc cgacaacctc taccccccg acattgagcg tgttcctctg   2100
tacatctacc cctggctcaa cagcactgac ctcaaggcct ctgccaacga ccccgactac   2160
ggccttccta ctgagaagta cgtgcctccc aacgccacca cggtgaccc ccagcccatt   2220
gaccctgctg gtggtgctcc tggtggcaac ccctccctct acgagcctgt tgctcgtgtc   2280
accaccatca tcaccaacac tggcaaggtc actggtgatg aggttcctca gctctacgtc   2340
agccttggtg gtcccgatga tgctcccaag gtcctccgtg gtttcgaccg tatcaccctg   2400
gctcctggcc agcagtacct ctggaccacc ccctcaccc gcgtgacat ctccaactgg   2460
gaccccgtca cccagaactg ggttgtcacc aactacacca gaccatcta cgtcggcaac   2520
agctctcgca acctgcccct ccaggctcct ctcaagccct accccggcat ataa           2574
```

<210> SEQ ID NO 16
<211> LENGTH: 459
<212> TYPE: PRT
<213> ORGANISM: Talaromyces emersonii
<220> FEATURE:
<221> NAME/KEY: MISC_FEATURE
<222> LOCATION: (1)..(459)
<223> OTHER INFORMATION: T. emersonii cellobiohydrolase II

<400> SEQUENCE: 16

```
Met Arg Asn Leu Leu Ala Leu Ala Pro Ala Ala Leu Leu Gly Ala
 1               5                  10                  15

Ala Asp Ala Gln Gln Ser Leu Trp Gly Gln Cys Gly Gly Asn Ser Trp
            20                  25                  30

Thr Gly Ala Thr Asp Cys Ala Ala Gly Ala Thr Cys Ser Thr Ile Asn
        35                  40                  45

Ser Tyr Tyr Ala Gln Cys Val Pro Ala Thr Ala Thr Pro Thr Thr Leu
    50                  55                  60

Thr Thr Thr Thr Lys Pro Ser Ser Thr Ala Pro Thr Thr Pro Pro Pro
65                  70                  75                  80

Thr Ser Ala Thr Thr Thr Gly Thr Gly Ser Ala Thr Ser Pro Ser Ile
                85                  90                  95

Thr Ala Ser Ala Ser Gly Asn Pro Phe Val Gly Tyr Gln Leu Tyr Ala
            100                 105                 110

Asn Pro Tyr Tyr Ala Ser Glu Val Ile Ser Leu Ala Ile Pro Ser Leu
```

```
            115                 120                 125
Ser Ser Glu Leu Val Pro Lys Ala Ser Glu Val Ala Lys Val Pro Ser
    130                 135                 140

Phe Val Trp Leu Asp Gln Ala Ala Lys Val Pro Asn Met Gly Glu Tyr
145                 150                 155                 160

Leu Lys Asp Ile Gln Ser Gln Asn Ala Ala Gly Ala Asp Pro Pro Ile
                165                 170                 175

Ala Gly Ile Phe Val Val Tyr Asp Leu Pro Asp Arg Asp Cys Ala Ala
            180                 185                 190

Ala Ala Ser Asn Gly Glu Phe Ser Ile Ala Asn Asn Gly Val Ala Leu
        195                 200                 205

Tyr Lys Gln Tyr Ile Asp Ser Ile Arg Glu Gln Leu Thr Thr Tyr Ser
    210                 215                 220

Asp Val His Thr Ile Leu Ile Ile Glu Pro Asp Ser Leu Ala Asn Leu
225                 230                 235                 240

Val Thr Asn Leu Asn Val Ala Lys Cys Ala Asn Ala Gln Gly Ala Tyr
                245                 250                 255

Leu Glu Cys Ile Asn Tyr Ala Ile Thr Gln Leu Asn Leu Pro Asn Val
            260                 265                 270

Ala Met Tyr Leu Asp Ala Gly His Ala Gly Trp Leu Gly Trp Ser Ala
        275                 280                 285

Asn Leu Gln Pro Ala Ala Gln Leu Phe Ala Glu Val Tyr Lys Asn Ala
    290                 295                 300

Ser Ser Pro Ala Ser Val Arg Gly Leu Ala Thr Asn Val Ala Asn Tyr
305                 310                 315                 320

Asn Ala Trp Thr Ile Ser Pro Cys Pro Ser Tyr Thr Gln Gly Asp Pro
                325                 330                 335

Asn Cys Asp Glu Glu Asp Tyr Val Asn Ala Leu Ala Pro Leu Leu Gln
            340                 345                 350

Ser Gln Gly Phe Asn Ala Tyr Phe Ile Thr Asp Thr Ser Arg Asn Gly
        355                 360                 365

Val Gln Pro Thr Lys Gln Asn Gln Trp Gly Asp Trp Cys Asn Val Ile
    370                 375                 380

Gly Thr Gly Phe Gly Val Arg Pro Thr Thr Asp Thr Gly Asn Pro Leu
385                 390                 395                 400

Glu Asp Ala Phe Val Trp Val Lys Pro Gly Gly Glu Ser Asp Gly Thr
                405                 410                 415

Ser Asn Thr Thr Ser Pro Arg Tyr Asp Tyr His Cys Gly Leu Ser Asp
            420                 425                 430

Ala Leu Gln Pro Ala Pro Glu Ala Gly Thr Trp Phe Gln Ala Tyr Phe
        435                 440                 445

Glu Gln Leu Leu Thr Asn Ala Asn Pro Pro Phe
    450                 455

<210> SEQ ID NO 17
<211> LENGTH: 1380
<212> TYPE: DNA
<213> ORGANISM: Talaromyces emersonii

<400> SEQUENCE: 17
atgcgaaatc tgcttgctct tgcaccggca gcgctgcttc tcggcgcagc ggacgcgcaa      60
caatccctct ggggacaatg cggagggaat tcgtggactg gagcgacgga ttgtgctgca     120
ggagcgacgt gcagcaccat caattcttac tacgcacaat gcgtccctgc aacggccact     180
```

-continued

```
cctaccacgt tgacgacaac gacaaagccc tcgtcgactg cgccaacgac ccctcctccg      240
acgtcagcga cgaccacagg cactggatcg gcgacatcgc cctccatcac cgcgtctgcg      300
tccggcaacc cctttgtcgg ataccagctc tacgccaacc cgtactatgc ctctgaggtg      360
attagcctgg ccatcccgtc gctaagcagc gagctggttc ccaaggcgag cgaggtggcc      420
aaggtgccgt cttttgtctg gctcgatcaa gcggccaaag tgcccaacat gggcgagtat      480
ctgaaagaca tccagtccca gaatgcggcc ggcgcagacc ctccgattgc aggcatcttc      540
gtcgtttacg acctacctga ccgcgactgc gcggcggcag cgagcaatgg cgagttctcc      600
atcgccaaca acggcgttgc cctgtacaag caatacatcg actcgatccg cgagcagctg      660
acgacgtatt cggatgtgca caccatcctg atcattgaac ccgacagcct ggccaacctg      720
gtcaccaacc tgaacgtggc gaaatgcgcg aatgcccagg cgcctatct cgaatgcatc       780
aactacgcca tcacgcagct caacctgccg aatgtggcca tgtatcttga tgctggacac      840
gccggatggc taggctggtc agcaaaacct caacccgctg cgcagctgtt tgcagaggtc      900
tacaagaacg cctcgtcgcc ggcctcggtg cgcggtctcg cgaccaacgt cgccaactac      960
aacgcctgga cgatcagccc gtgcccgtcg tacacgcagg gcgaccccaa ctgcgacgag     1020
gaggactatg tgaatgccct tgcgccgctg cttcagagcc aggggtttaa tgcgtacttt     1080
atcactgata catcccgcaa cggcgtccaa ccccaccaagc agaaccaatg gggcgactgg    1140
tgcaacgtca tcggcaccgg gttcggcgtc cgcccgacga ctgacactgg caaccctctc     1200
gaggacgcct tcgtctgggt caagccgggt ggcgagagcg atggcacgtc taacacgacc     1260
tctccgcgat acgactacca ctgcgggctg agcgatgcgc tgcagccggc tccggaggcg     1320
ggaacttggt tccaggcgta ctttgagcag ctgcttacga atgccaatcc gccgttctga     1380
```

<210> SEQ ID NO 18
<211> LENGTH: 209
<212> TYPE: PRT
<213> ORGANISM: Talaromyces emersonii
<220> FEATURE:
<221> NAME/KEY: MISC_FEATURE
<222> LOCATION: (1)..(209)
<223> OTHER INFORMATION: Talaromyces emersonii unknown protein

<400> SEQUENCE: 18

```
Met Lys Gln Thr Ala Val Leu Pro Ile Leu Pro Ile Leu Phe Thr Thr
1               5                   10                  15

Ala Arg Ala Gly Asn Ile Leu Trp Ser Gly Ile Phe Asn Ser Ser Val
                20                  25                  30

Thr Val Ala Asp Phe Asp Leu Trp Ser Trp Ser Asn Gln Ile Glu Pro
            35                  40                  45

Trp Gln Trp Tyr Ile His Gly Ser Gly Pro Thr Ser Glu Tyr Leu Gly
        50                  55                  60

Leu Ser Pro Asp Phe Lys Asn Pro Ala Asp Thr Ser Asp Ala Gln Gly
65                  70                  75                  80

Ile Arg Ile Thr Ile Ser His Phe Thr Glu Ile Lys Tyr Gly Thr Leu
                85                  90                  95

Ser Gly Gln Thr Ala Pro Asp Asn Thr Leu Arg Trp Asp Val Gln Ser
            100                 105                 110

Val Thr Gln Trp Ser Thr Gln Leu Val Pro Asp Asn Trp Tyr Asn Phe
        115                 120                 125

Ala Tyr Asp Ile Asp Phe Asp Ala Gly Thr Val Gly Leu Trp Ala Ser
    130                 135                 140
```

Asn Gly Ser Asp Pro Leu Gln Gln Val Val Ala Pro Ile Ser Ala Ala
145                 150                 155                 160

Thr Ser Thr Asn Ser Glu Asp Trp His Val Gly Glu Leu Arg Leu Pro
                165                 170                 175

Asn Gly Gly Ser Asp Pro Ala Pro Glu Asp Trp Tyr Trp Ser Gly Ile
            180                 185                 190

Trp Ile Glu Gln Ala Pro Ile Thr Thr Ser Ile Ala Gly Pro Leu Ala
        195                 200                 205

Ser

<210> SEQ ID NO 19
<211> LENGTH: 630
<212> TYPE: DNA
<213> ORGANISM: Artificial Sequence
<220> FEATURE:
<223> OTHER INFORMATION: Talaromyces emersonii unknown protein (DNA
      coding region)

<400> SEQUENCE: 19
atgaagcaga cagcagtcct ccccattctt ccaatcctct tcaccaccgc tcgcgcgggc      60
aatatcctct ggagcggaat cttcaattcc tccgtcacgg ttgcggactt tgatttgtgg     120
tcctggtcca accagatcga gccatggcaa tggtacatcc acggcagtgg gccgacgagc     180
gagtatctgg gtctgtcgcc tgatttcaag aatccagcgg atacgagcga tgcgcagggc     240
ataaggatta caattagcca cttcaccgaa ataaaatacg gcacgctgag cggacaaacc     300
gccccggata cacgctgcg ctgggacgtg caatccgtca cgcagtggtc gacgcaactg      360
gtgccagaca actggtacaa ctttgcgtac gacatcgact tcgacgcggg gaccgtcggc     420
ctctgggcgt ccaacggctc ggatccgctg cagcaggtcg tggcgcccat cagcgcggcg     480
acgtcgacca attctgaaga ctggcacgtc ggcgagttgc gtttgcccaa cggtggttcg     540
gacccggcgc ctgaggactg gtactggtct ggtatttgga ttgagcaggc tcctattacg     600
acgagcattg cggggccgtt ggctagctaa                                      630

<210> SEQ ID NO 20
<211> LENGTH: 632
<212> TYPE: PRT
<213> ORGANISM: Talaromyces emersonii
<220> FEATURE:
<221> NAME/KEY: MISC_FEATURE
<222> LOCATION: (1)..(632)
<223> OTHER INFORMATION: Talaromyces emersonii Swollenin

<400> SEQUENCE: 20

Met Gln Val Ser Arg Ile Ala Ala Leu Ala Ala Leu Leu Gln Gly Ala
1               5                   10                  15

Trp Ala Gln Ala Gly Pro Tyr Ala Gln Cys Gly Gly Leu Gly Tyr Ser
            20                  25                  30

Gly Ser Thr Val Cys Thr Ala Gly Tyr Ile Cys Thr Ser Gln Asn Pro
        35                  40                  45

Tyr Tyr Tyr Gln Cys Val Pro Ala Thr Ala Thr Thr Ile Ala Ala
    50                  55                  60

Thr Thr Thr Thr Ser Pro Ala Ser Ala Ser Ser Thr Ser Thr Ala Pro
65                  70                  75                  80

Ser Thr Thr Cys Thr Gly Thr Phe Thr Pro Ile Ser Ala Ala Asp Phe
            85                  90                  95

Val Ala Asn Leu Asn Pro Gly Trp Asn Leu Gly Asn Thr Leu Asp Ala
            100                 105                 110

```
Ile Pro Asp Glu Gly Ser Trp Asn Asn Pro Val Pro Leu Thr
    115                 120                 125

Phe Asp Asp Val Lys Ala Ala Gly Phe Lys Ser Val Arg Leu Pro Val
130                 135                 140

Thr Tyr Ala Tyr His Phe Val Gly Gly Ser Pro Asp Trp Thr Ile Asn
145                 150                 155                 160

Ala Thr Trp Leu Gln Arg Val Ser Asp Val Asp Met Ile Thr Ser
                165                 170                 175

Arg Gly Leu Tyr Ala Ile Val Asn Ala His His Asp Ser Trp Ile Trp
                180                 185                 190

Ala Asp Val Thr Gln Pro Gly Ala Asn Leu Thr Met Ile Glu Glu Lys
                195                 200                 205

Phe Tyr Arg Leu Trp Tyr Gln Val Gly Ser Lys Leu Ala Cys Lys Ser
                210                 215                 220

Ser Leu Val Ala Phe Glu Pro Ile Asn Glu Pro Pro Cys Asn Asp Ala
225                 230                 235                 240

Thr Asp Ala Ala Glu Ile Asn Lys Leu Asn Ala Ile Phe Leu Lys Ala
                245                 250                 255

Ile Asn Asp Ala Gly Gly Phe Asn Ala Gln Arg Val Val Thr Leu Val
                260                 265                 270

Gly Gly Gly Glu Asp Ser Val Lys Thr Ser Glu Trp Phe Val Ala Pro
                275                 280                 285

Thr Gly Tyr Pro Asn Pro Tyr Ala Ile Gln Phe His Tyr Tyr Asn Pro
                290                 295                 300

Tyr Asp Phe Ile Phe Ser Ala Trp Gly Lys Thr Ile Trp Gly Ser Glu
305                 310                 315                 320

Ser Asp Lys Ser Ala Leu Ser Thr Asp Leu Gln Leu Ile Arg Asn Asn
                325                 330                 335

Phe Thr Thr Val Pro Leu Leu Ile Gly Glu Tyr Asp Ala Ser Pro Thr
                340                 345                 350

Asn Cys Glu Thr Ala Ala Arg Trp Lys Tyr Phe Asp Tyr Phe Ile Arg
                355                 360                 365

Thr Ala Ser Ala Leu Asn Ile Ser Thr Ile Leu Trp Asp Asn Gly Gly
                370                 375                 380

Asp His Leu Asp Arg Thr Thr Gly Thr Trp Arg Asp Pro Ser Ala Ile
385                 390                 395                 400

Asn Ile Ile Met Asp Ala Thr Gly Gly Ile Thr Asn Ser Leu Pro Asp
                405                 410                 415

Ser Thr Glu Asp Pro Ser Ala Thr Thr Gln Trp Ser Ser Ala Tyr Ile
                420                 425                 430

Phe His Lys Tyr Gly Asp Pro Val Ser Asp Gln Ser Leu Pro Phe Leu
                435                 440                 445

Phe Asn Gly Asn Ser Val Ser Ser Ile Ser Ala Ser Asp Gly Thr Lys
450                 455                 460

Leu Thr Ala Asp Thr Asp Tyr Val Val Ala Gly Ser Asn Ile Thr Phe
465                 470                 475                 480

Lys Ala Ser Phe Leu Ser Lys Tyr Leu Ser Ser Thr Thr Ala Pro Gly
                485                 490                 495

Ile Leu Ala Asn Leu Thr Val Ser Phe Ser Ala Gly Ala Ser Glu Val
                500                 505                 510

Ile Gln Leu Val Gln Trp Lys Thr Pro Ser Leu Ser Ser Thr Ser Ala
                515                 520                 525
```

```
Val Ala Ser Ala Val Asn Gly Ser Asp Leu Tyr Ile Pro Ile Thr Trp
            530                 535                 540

Gly Gly Ile Pro Lys Pro Ala Ala Val Lys Ala Val Glu Ala Asn Gly
545                 550                 555                 560

Asn Tyr Leu Val Asp Ser Trp Thr Glu Tyr Leu Pro Ala Ile Gln Gln
                565                 570                 575

Gly Arg Thr Thr Tyr Ser Ser Gln Trp Asn Trp Asp Asp Ser His Val
            580                 585                 590

Ile Ile Thr Ala Ala Thr Ile Ser Asp Val Leu Ala Ala Gly Gln Thr
            595                 600                 605

Thr Val Phe Thr Phe Glu Phe Tyr Pro Arg Asp Asn Gly Val Val Asn
610                 615                 620

Ala Val Asn Phe Thr Leu Thr Val
625                 630

<210> SEQ ID NO 21
<211> LENGTH: 1932
<212> TYPE: DNA
<213> ORGANISM: Artificial Sequence
<220> FEATURE:
<223> OTHER INFORMATION: Talaromyces emersonii Swollenin (DNA coding
      region)

<400> SEQUENCE: 21
```

| | | | | | |
|---|---|---|---|---|---|
| atgcaggtct | ctcgtatcgc | tgcacttgct | gccctcctgc | agggtgcctg | ggcacaagca | 60 |
| ggcccctacg | ctcagtgcgg | cggactcggc | tattcaggaa | gcaccgtctg | cactgcaggt | 120 |
| tatatctgca | cttcacagaa | tccttattat | atcagtgtg | tcccggcaac | agcaacgact | 180 |
| acaatcgcag | caacgactac | aacctcgcct | gcttcagcat | cctccacttc | cactgcccct | 240 |
| tcgaccactt | gcactgggac | gttcacgccc | atctcagccg | ccgactttgt | cgccaatctc | 300 |
| aatcccggat | ggaacttggg | aaacacactc | gatgcaatcc | ccgacgaagg | gtcatggaat | 360 |
| aatcctcccg | ttgtgccgtt | gacgtttgac | gatgtgaaag | cggcgggttt | caagagcgtc | 420 |
| agacttccag | tcacctatgc | atatcacttt | gtaggtggct | cccctgactg | gaccatcaac | 480 |
| gcgacatggc | tgcagagggt | atccgacgtg | gttgacatga | tcacatcccg | cggggttgtac | 540 |
| gccatcgtca | acgctcatca | cgactcgtgg | atctgggcgg | acgtaaccca | gccaggcgca | 600 |
| aatctgacca | tgatcgagga | aaagttctac | cgtctctggt | accaagtagg | cagcaagctg | 660 |
| gcgtgcaagt | ccagcctggt | cgcattcgag | cccatcaacg | aaccgccctg | caacgatgcg | 720 |
| actgacgccg | ccgaaatcaa | caagctgaat | gccatcttcc | tgaaggcaat | caacgatgcc | 780 |
| ggcggattca | atgcccagcg | cgtggtgacc | ctcgttggtg | gcggcgagga | cagcgtcaag | 840 |
| acatcggagt | ggttcgtggc | gccgacgggg | tatccgaatc | cttatgcgat | tcagttccac | 900 |
| tactacaatc | cttatgattt | tatttttcagc | gcatggggca | agacgatctg | ggctcagaa | 960 |
| tccgacaaat | ccgccctgtc | gaccgatctc | caactgatcc | gaaacaactt | cactaccgtt | 1020 |
| cctcttctga | tcggagaata | cgatgcgtcc | ccgacaaact | gcgaaacggc | cgcgcggtgg | 1080 |
| aagtacttcg | actatttcat | ccgcaccgct | agcgcgctca | acatatcaac | catcctgtgg | 1140 |
| gataacggtg | agatcatct | cgaccgtacg | accggcacct | ggcgcgatcc | atctgccatc | 1200 |
| aacatcatca | tggacgcaac | cgggggaatc | accaacagcc | tgcccgacag | cacggaggat | 1260 |
| ccgagcgcga | cgacgcagtg | gtcgtccgcg | tacatcttcc | acaaatacgg | ggatccggtc | 1320 |
| agcgatcaga | gtctcccgtt | cctgttcaac | gggaactccg | tttcgtcgat | cagtgcgtcg | 1380 |
| gacgggacga | aattaacggc | tgatacggac | tacgtcgttg | ccggctcgaa | tatcacattc | 1440 |

```
aaggcgtcgt tcctctcgaa atacctctct tcgacaaccg cgccgggcat tctcgccaat    1500
ctgaccgtga gcttctctgc gggtgcttcg gaggtgatcc agctcgtgca gtggaaaacg    1560
ccttcactgt cgtccacttc cgcggttgcg tctgccgtca acggctccga tctttacatc    1620
cctatcacct ggggcggtat accgaagcca gcggccgtga agccgtcga ggcgaatggg     1680 aactacctcg tcgacagctg acggaatac ctacctgcga tccagcaggg gaggacaaca     1740
tacagcagcc agtggaactg ggacgactcg catgtcatca tcactgcagc gacaatcagc    1800
gacgttcttg ctgcgggcca cgactgtg tttacgttcg agttttatcc tcgagataac      1860
ggggttgtca acgcggtcaa ttttacgctg actgtgtaaa tacgtacaat caatccattt    1920
cgctatagtt aa                                                        1932

<210> SEQ ID NO 22
<211> LENGTH: 300
<212> TYPE: PRT
<213> ORGANISM: Talaromyces emersonii
<220> FEATURE:
<221> NAME/KEY: MISC_FEATURE
<222> LOCATION: (1)..(300)
<223> OTHER INFORMATION: Talaromyces emersonii acetyl xylan esterase

<400> SEQUENCE: 22

Met Ala Arg Phe Ser Ile Leu Ser Ala Ile Tyr Leu Tyr Ile Leu Leu
1               5                   10                  15

Val Gly Ser Cys Leu Ala Gln Val Pro Arg Gly Ser Leu Gln Gln Val
            20                  25                  30

Thr Asn Phe Gly Ser Asn Pro Thr Asn Val Gly Met Tyr Ile Tyr Val
        35                  40                  45

Pro Asn Asn Leu Ala Ala Lys Pro Gly Ile Val Val Ala Ile His Tyr
    50                  55                  60

Cys Thr Gly Ser Ala Gln Ala Tyr Tyr Ser Gly Thr Pro Tyr Ala Gln
65                  70                  75                  80

Leu Ala Glu Gln Tyr Gly Phe Ile Val Ile Tyr Pro Ser Ser Pro Tyr
                85                  90                  95

Ser Gly Thr Cys Trp Asp Val Ser Gln Ala Ala Leu Thr His Asn
            100                 105                 110

Gly Gly Gly Asp Ser Asn Ser Ile Ala Asn Met Val Thr Trp Thr Ile
        115                 120                 125

Gln Gln Tyr Asn Ala Asp Thr Ser Lys Val Phe Val Thr Gly Ser Ser
    130                 135                 140

Ser Gly Ala Met Met Thr Asn Val Met Ala Ala Thr Tyr Pro Glu Leu
145                 150                 155                 160

Phe Ala Ala Ala Thr Val Tyr Ser Gly Val Ala Ala Gly Cys Phe Val
                165                 170                 175

Ser Ser Thr Asn Gln Val Asp Ala Trp Asn Ser Ser Cys Ala Leu Gly
            180                 185                 190

Gln Val Val Asn Thr Pro Gln Val Trp Ala Gln Val Ala Glu Asn Met
        195                 200                 205

Tyr Pro Gly Tyr Asn Gly Pro Arg Pro Arg Met Gln Ile Tyr His Gly
    210                 215                 220

Ser Ala Asp Thr Thr Leu Tyr Pro Gln Asn Tyr Tyr Glu Glu Cys Lys
225                 230                 235                 240

Gln Trp Ala Gly Val Phe Gly Tyr Asp Tyr Asn Asn Pro Gln Gln Val
                245                 250                 255
```

```
Glu Gln Asn Thr Pro Glu Ala Asn Tyr Gln Thr Thr Ile Trp Gly Pro
            260                 265                 270

Asn Leu Gln Gly Ile Tyr Ala Thr Gly Val Gly His Thr Val Pro Ile
        275                 280                 285

His Gly Gln Gln Asp Met Glu Trp Phe Gly Phe Ala
    290                 295                 300

<210> SEQ ID NO 23
<211> LENGTH: 903
<212> TYPE: DNA
<213> ORGANISM: Talaromyces emersonii

<400> SEQUENCE: 23
atggcacgct tttcaattct ttctgctatc tatctctata tccttttggt cggttcctgt      60
cttgcccagg tgcctcgtgg ctcgcttcag caggtcacca atttcgggtc caatccgacc     120
aatgtgggca tgtacattta tgtgccaaac aatctggctg cgaaaccggg gatagtcgtg     180
gccattcatt actgcactgg ttccgcgcag gcatactatt ctggcacccc gtacgcacag     240
ttggcagagc agtatggctt catcgtcatc tacccgagca gcccatacag cggcacctgc     300
tgggatgtca gctcgcaggc agccctcacc cacaacggcg gtggagacag caactcgatt     360
gccaatatgg tcacctggac gatccagcaa tataacgcgg acacgagcaa ggtctttgtg     420
acagggagca gctctggagc gatgatgacg aacgtcatgg cagccaccta ccccgagctc     480
ttcgctgcag ccaccgtcta ctcgggcgtt gcggcaggat gcttcgtttc gtccacgaac     540
caggtcgacg catggaacag cagctgcgcc ttgggccagg tcgtcaacac gccgcaggta     600
tgggcccagg tggccgaaaa catgtacccg ggctacaacg gccccgacc ccggatgcag      660
atctaccacg gcagcgccga cacgacgctc tacccgcaga actactacga ggagtgcaag     720
cagtgggccg gcgtctttgg ctacgactac aacaaccccc agcaggttga gcagaacacg     780
cccgaggcca actatcagac cacgatctgg ggccccgaacc tgcaggggat ctacgctacg     840
ggagttggcc atacggttcc tatccatggt cagcaggaca tggagtggtt tgggtttgcg     900
tag                                                                   903

<210> SEQ ID NO 24
<211> LENGTH: 408
<212> TYPE: PRT
<213> ORGANISM: Talaromyces emersonii
<220> FEATURE:
<221> NAME/KEY: MISC_FEATURE
<222> LOCATION: (1)..(408)
<223> OTHER INFORMATION: Talaromyces emersonii xylanase

<400> SEQUENCE: 24

Met Val Arg Leu Ser Pro Val Leu Leu Ala Ser Ile Ala Gly Ser Gly
1               5                  10                  15

Leu Pro Leu Ala Gln Ala Ala Gly Leu Asn Thr Ala Ala Lys Ala Ile
            20                  25                  30

Gly Leu Lys Tyr Phe Gly Thr Ala Thr Asp Asn Pro Glu Leu Ser Asp
        35                  40                  45

Thr Ala Tyr Glu Thr Gln Leu Asn Asn Thr Gln Asp Phe Gly Gln Leu
    50                  55                  60

Thr Pro Ala Asn Ser Met Lys Trp Asp Ala Thr Glu Pro Glu Gln Asn
65                  70                  75                  80

Val Phe Thr Phe Ser Ala Gly Asp Gln Ile Ala Asn Leu Ala Lys Ala
                85                  90                  95
```

```
Asn Gly Gln Met Leu Arg Cys His Asn Leu Val Trp Tyr Asn Gln Leu
            100                 105                 110

Pro Ser Trp Val Thr Ser Gly Ser Trp Thr Asn Glu Thr Leu Leu Ala
        115                 120                 125

Ala Met Lys Asn His Ile Thr Asn Val Val Thr His Tyr Lys Gly Gln
    130                 135                 140

Cys Tyr Ala Trp Asp Val Val Asn Glu Ala Leu Asn Asp Asp Gly Thr
145                 150                 155                 160

Tyr Arg Ser Asn Val Phe Tyr Gln Tyr Ile Gly Glu Ala Tyr Ile Pro
                165                 170                 175

Ile Ala Phe Ala Thr Ala Ala Ala Ala Asp Pro Asn Ala Lys Leu Tyr
            180                 185                 190

Tyr Asn Asp Tyr Asn Ile Glu Tyr Pro Gly Ala Lys Ala Thr Ala Ala
        195                 200                 205

Gln Asn Leu Val Lys Leu Val Gln Ser Tyr Gly Ala Arg Ile Asp Gly
    210                 215                 220

Val Gly Leu Gln Ser His Phe Ile Val Gly Glu Thr Pro Ser Thr Ser
225                 230                 235                 240

Ser Gln Gln Gln Asn Met Ala Ala Phe Thr Ala Leu Gly Val Glu Val
                245                 250                 255

Ala Ile Thr Glu Leu Asp Ile Arg Met Gln Leu Pro Glu Thr Glu Ala
            260                 265                 270

Leu Leu Thr Gln Gln Ala Thr Asp Tyr Gln Ser Thr Val Gln Ala Cys
        275                 280                 285

Ala Asn Thr Lys Gly Cys Val Gly Ile Thr Val Trp Asp Trp Thr Asp
    290                 295                 300

Lys Tyr Ser Trp Val Pro Ser Thr Phe Ser Gly Tyr Gly Asp Ala Cys
305                 310                 315                 320

Pro Trp Asp Ala Asn Tyr Gln Lys Lys Pro Ala Tyr Glu Gly Ile Leu
                325                 330                 335

Thr Gly Leu Gly Gln Thr Val Ser Thr Thr Tyr Ile Ile Ser Pro
            340                 345                 350

Thr Thr Ser Val Gly Thr Gly Thr Thr Thr Ser Ser Gly Gly Ser Gly
        355                 360                 365

Gly Thr Thr Gly Val Ala Gln His Trp Glu Gln Cys Gly Gly Leu Gly
    370                 375                 380

Trp Thr Gly Pro Thr Val Cys Ala Ser Gly Tyr Thr Cys Thr Val Ile
385                 390                 395                 400

Asn Glu Tyr Tyr Ser Gln Cys Leu
                405

<210> SEQ ID NO 25
<211> LENGTH: 1227
<212> TYPE: DNA
<213> ORGANISM: Talaromyces emersonii

<400> SEQUENCE: 25
atggttcgcc tcagtccagt cttgctcgcc tccatcgcag gctctggcct gcctctagcc      60
caagcagcag gcctcaacac agccgccaaa gccatcggcc tgaaatactt tggcacagcg     120
accgacaacc ccgagctgag cgacaccgcg tacgagacgc agctcaacaa cacgcaggat     180
ttcgggcagt tgacgccggc gaattcgatg aagtgggatg ccaccgagcc cgagcagaat     240
gtcttcacgt ttagccgcgg cgatcagatt gccaacttgg ccaaggcgaa tggccagatg     300
ttgcggtgtc ataatcttgt ttggtacaat cagttgccgt cgtgggtcac cagtggctcc     360
```

```
tggaccaacg agacgctgct tgctgccatg aagaatcaca tcaccaacgt cgttacccat    420
tacaagggcc agtgctacgc atgggatgtc gttaatgagg ccctcaacga cgacggcacc    480
taccgcagca acgtcttcta ccagtacatc ggtgaggcgt acatccccat cgccttcgcg    540
acggccgccg ccgccgaccc caacgccaag ctgtactaca acgactacaa catcgagtac    600
ccgggggcca aggcgacggc ggcgcagaac ctggtcaagc tggtgcagtc gtacggcgcg    660
cgcatcgacg gcgtcggcct gcagtcgcac ttcatcgtgg gcgagacgcc cagcaccagc    720
tcccagcagc agaacatggc cgccttcacg gcgctgggcg tcgaggtcgc catcaccgag    780
ctcgacatcc gcatgcagct gcccgagacg gaagccctgc tgacgcagca ggccaccgac    840
taccagagca ccgtgcaggc ctgcgccaac accaagggct gcgtcggcat caccgtctgg    900
gactggaccg acaagtactc gtgggtgccc agcaccttct cgggctatgg cgacgcctgt    960
ccctgggacg ccaactacca gaagaagccc gcgtacgaag gcatcctcac tgggcttgga    1020
cagacggtca ccagcaccac ctacatcatc tcgccgacga cgtctgtcgg aacgggcacg    1080
acgacctcga gcggcggaag cggcggcacg actggcgtgg cccagcattg ggagcagtgc    1140
ggtggactgg gctggactgg tccgacggtt tgcgcaagtg gctacacttg cactgtcatc    1200
aatgagtatt actcgcagtg tctgtaa                                       1227
```

TALAROMYCES TRANSFORMANTS

CROSS REFERENCE TO RELATED APPLICATIONS

This application is a §371 National Stage Application of PCT/EP2010/066796, filed Nov. 4, 2010, which claims priority to European Application No. 09174990.3, filed Nov. 4, 2009.

BACKGROUND OF THE INVENTION

1. Field of the Invention

The invention relates to a process for the production of *Talaromyces* transformants, to *Talaromyces* transformants and to a process for production of polypeptide using the *Talaromyces* transformants. The invention also relates to a process for saccharification of lignocellulosic material, wherein the lignocellulosic material is contacted with the transformant or a cellulase, hemicellulase and/or pectinase produced by the transformant, and sugars are produced. Further the invention relates to a process for the preparation of a fermentation product, for instance ethanol, wherein those sugars are fermented with a fermenting microorganism, preferably yeast, to produce the fermentation product.

2. Description of Related Art

Carbohydrates constitute the most abundant organic compounds on earth. However, much of this carbohydrate is sequestered in complex polymers including starch (the principle storage carbohydrate in seeds and grain), and a collection of carbohydrates and lignin known as lignocellulose. The main carbohydrate components of lignocellulose are cellulose, hemicellulose, and pectins. These complex polymers are often referred to collectively as lignocellulose.

Bioconversion of renewable lignocellulosic biomass to a fermentable sugar that is subsequently fermented to produce alcohol (e.g., ethanol) as an alternative to liquid fuels has attracted an intensive attention of researchers since 1970s, when the oil crisis broke out because of decreasing the output of petroleum by OPEC. Ethanol has been widely used as a 10% blend to gasoline in the USA or as a neat fuel for vehicles in Brazil in the last two decades. More recently, the use of E85, an 85% ethanol blend has been implemented especially for clean city applications. The importance of fuel bioethanol will increase in parallel with increases in prices for oil and the gradual depletion of its sources. Additionally, fermentable sugars are being used to produce plastics, polymers and other biobased products and this industry is expected to grow substantially therefore increasing the demand for abundant low cost fermentable sugars which can be used as a feed stock in lieu of petroleum based feedstocks.

The sequestration of such large amounts of carbohydrates in plant biomass provides a plentiful source of potential energy in the form of sugars, both five carbon and six carbon sugars that could be utilized for numerous industrial and agricultural processes. However, the enormous energy potential of these carbohydrates is currently under-utilized because the sugars are locked in complex polymers, and hence are not readily accessible for fermentation. Methods that generate sugars from plant biomass would provide plentiful, economically-competitive feedstocks for fermentation into chemicals, plastics, such as for instance succinic acid and (bio) fuels, including ethanol, methanol, butanol synthetic liquid fuels and biogas.

Regardless of the type of cellulosic feedstock, the cost and hydrolytic efficiency of enzymes are major factors that restrict the commercialization of the biomass bioconversion processes. The production costs of microbially produced enzymes are tightly connected with a productivity of the enzyme-producing strain and the final activity yield in the fermentation broth.

In spite of the continued research of the last few decades to understand enzymatic lignocellulosic biomass degradation and cellulase production, it remains desirable to discover or to engineer new highly active cellulases and hemicellulases. It would also be highly desirable to construct highly efficient enzyme compositions capable of performing rapid and efficient biodegradation of lignocellulosic materials.

Such enzyme compositions may be used to produce sugars for fermentation into chemicals, plastics, such as for instance succinic acid and (bio) fuels, including ethanol, methanol, butanol, synthetic liquid fuels and biogas, for ensiling, and also as enzyme in other industrial processes, for example in the food or feed, textile, pulp or paper or detergent industries and other industries.

One genus of microorganisms that is known to produce suitable enzymes for enzymatic lignocellulosic biomass degradation is the genus *Talaromyces*. *Talaromyces* is a filamentous fungus.

Jain, S. et al, Mol Gen Genet (1992), 234, 489-493 discloses a transformation system for the fungus *Talaromyces* sp CL240. No expression of polypeptides is disclosed.

Murray, F. R. et al, Curr Genet (1997), 32, 367-375 discloses over-expression of the glucose oxidase gene from *Talaromyces flavus* in *Talaromyces macrosporus*. The effect fungal isolates on growth inhibition of *V. dahliae* was studied.

WO200170998 discloses *Talaromyces emersonii* beta-glucanases. On page 16, it is described that the polynucleotide of beta-glucanase may be heterologously expressed in a host, e.g. a yeast cell.

WO200224926 discloses *Talaromyces emersonii* xylanase. On page 24, $5^{th}$ paragraph, it is described that production of the polypeptide may be achieved by recombinant expression of the xylanase DNA sequence in a suitable homologous or heterologous host cell. In paragraph 7, it is said that the host cell may over-express the polypeptide, and techniques for engineering over-expression are well known from WO99/32617. WO99/32617 relates to expression cloning, but does not disclose cloning in *Talaromyces* host.

WO2007091231 discloses strains of *Talaromyces emersonii* which are thermostable and encode thermostable enzymes, and also discloses enzyme compositions produced by the *Talaromyces emersonii* strains. No recombinant production of homologous or heterologous polypeptides is disclosed. In table 1 shows inducing carbon sources were added in an amount of 0.2-6%. Solka floc and glucose (2%) were included for comparative purposes. On page 78, line 28 it is said that "glucose does not completely repress exoglucosidase production by the *T. emersonii* strains (table 31A). Table 31A shows that IMI393751 produces beta-glucosidase activity of 31.90 IU with glucose as carbon source, but no other cellulase activities, e.g. glucanases or xylanases. Due to lack of such enzyme activities, the strain IMI393751 is not suitable for the production of cellulases for the conversion of lignocellulose on glucose as carbon source.

SUMMARY

The presence of a cellulase inducer, necessary sofar in *Talaromyces* cellulase production methods, has several disadvantages. First, the inducer, such as a plant material, may have a variable composition, which is disadvantageous for the controllability of the cellulase production process. Secondly, energy is required to sterilise plant material for induction.

Thirdly, plant material will heavily pollute the equipment. Fourthly, the inducer may result in a higher viscosity of the cellulase production medium. Fifthly, the presence of inducer, in particular when it has been pre-treated, may result in the production of inhibitors that may be detrimental to *Talaromyces*. There is therefore a need for an improved process and improved *Talaromyces* strains for production of polypeptide compositions suitable for enzymatic lignocellulosic biomass degradation in *Talaromyces*.

It is therefor an object of the invention to provide *Talaromyces* strains suitable in the conversion of lignocellulose to sugar. A further object is to provide such *Talaromyces* strains that may be produced in glucose medium, without cellulase inducers. The invention now provides a process for production of a *Talaromyces* transformant comprising the steps of:

(a) providing one or more expression cassettes capable of producing one or more polypeptides of interest and comprising one or more polynucleotide of interest coding for cellulase, hemicellulase and/or pectinase and at least one promoter for expression of the polynucleotide;
(b) providing a selection marker included in the expression cassette of (a) or included in a dedicated selection marker polynucleotide;
(c) transfecting a *Talaromyces* host with the one or more expression cassette from (a) and/or the selection marker from (b);
(d) selecting a *Talaromyces* transformant which contains one or more polynucleotides encoding cellulase, hemicellulase and/or pectinase and
(e) isolating the *Talaromyces* transformant.

The invention further provides *Talaromyces* transformants comprising one or more recombinant gene, capable of producing cellulase in the absence of cellulase inducer in a glucose medium, having a cellulase activity of 2 WSU/ml or more in 16 times or more diluted supernatant or broth, obtainable according to the above process.

The *Talaromyces* transformants of the invention may be cultured on a medium comprising a suitable carbon source, such as sugar, e.g. glucose, without cellulase inducer (glucose is herein not a cellulase inducer, i.e. cellulase inducer does not include glucose) and produce cellulases which have lignocellulose degrading activity.

The invention further relates to a process for production of a polypeptide composition of one or more cellulases, hemicellulases and/or pectinases comprising the steps of:

(a) providing one or more expression cassettes capable of producing one or more polypeptides of interest and comprising one or more polynucleotide of interest coding for cellulase, hemicellulase and/or pectinase and at least one promoter for expression of the polynucleotide;
(b) providing a selection marker included in the expression cassette of (a) or included in a dedicated selection marker polynucleotide;
(c) transfecting a *Talaromyces* host with the one or more expression cassette from (a) and/or the selection marker from (b);
(d) optionally selecting a *Talaromyces* transformant which contains one or more polynucleotides encoding cellulase, hemicellulase and/or pectinase;
(e) producing the polypeptide by culturing the *Talaromyces* transformant in a suitable culture medium in which a cellulase inducer is substantially absent; and
(f) optionally recovering the polypeptide composition;

Further embodiments are described below in the detailed description of the invention.

Figure 1:
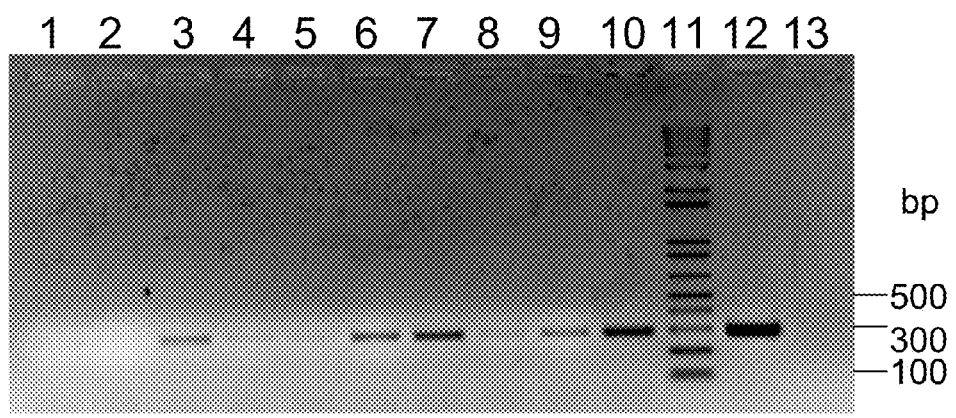
FIG. 1. Detection of PCR fragment of the β-lactamase gene of pAN8-1. Agarose gel showing the 278 nucleotides β-lactamase gene PCR fragment in *T. emersonii* transformants. Lanes 1-10 contain PCR fragments of PCR reactions using chromosomal DNA of 10 pAN8-1 *T. emersonii* transformants as template; lane 11 contains a molecular weight marker; lane 12 contains the PCR fragment of a PCR reaction using pAN8-1 plasmid as template for PCR; lane 13 contains a PCR reaction mix using the chromosomal DNA of een empty strain as template.

(4A): SDS-PAGE detection of FLAG-tagged *T. emersonii* beta-glucanase CEB protein, expressed in *T. emersonii* grown in *Talaromyces* medium 1 (lanes 1-3) and *Talaromyces* medium 2 (lanes 5-7). Supernatants of *T. emersonii* pGBFINEBA7 transformant 1#6 (lanes 1, 5) and 1#14 (lanes 2, 6) harvested from 72 hours cultures; lanes 3 and 7 contain supernatants of a 72 hours culture of an empty strain; lane 4 contains a molecular weight marker.

(4B): Western blot detection of FLAG-tagged *T. emersonii* beta-glucanase CEB protein, expressed in *T. emersonii* grown in *Talaromyces* medium 1 (lanes 2-7) and *Talaromyces* medium 2 (lanes 9-14), using a FLAG-tag specific antibody. Lanes 1 and 8 contain a molecular weight marker; lanes 2, 3, 9 and 10 contain supernatants of pGBFINEBA7 *T. emersonii* transformant 1#6 harvested from a 72 hours (lane 2, 9) and 96 hours (lane 3, 10) culture; lanes 4, 5, 11 and 12 contain supernatants of pGBFINEBA7 *T. emersonii* transformant 1#14 harvested from a 72 hours (lane 4, 11) and 96 hours (lane 5, 12) culture; lane 6 and 13, and 7 and 14 contain supernatants of, respectively, 72 hours and 96 hours cultures of an empty strain.

(4C): Copy number determination of transformants by PCR. Agarose gel showing the 1285 nucleotides expression cassette PCR fragment and the 373 nucleotides actin genomic control/reference PCR fragment of *T. emersonii* transformants. The intensity of the 1285 nucleotides PCR product of the EBA7 gene is indicative for the copy number of the gene, upon normalization of the 1285 nt PCR signal with the 373 nt actin genomic reference signal. PCR fragments of pGBFINEBA7 transformant 1#6 and 1#14 are shown in lane 1 and 2, respectively; lane 3 shows a molecular weight marker; PCR fragments of pGBFIN-Pgpd-EBA7 transformant 8#14, 8#18, and 8#32 are shown in lane 4, 5, and 6, respectively.

Figure 5:
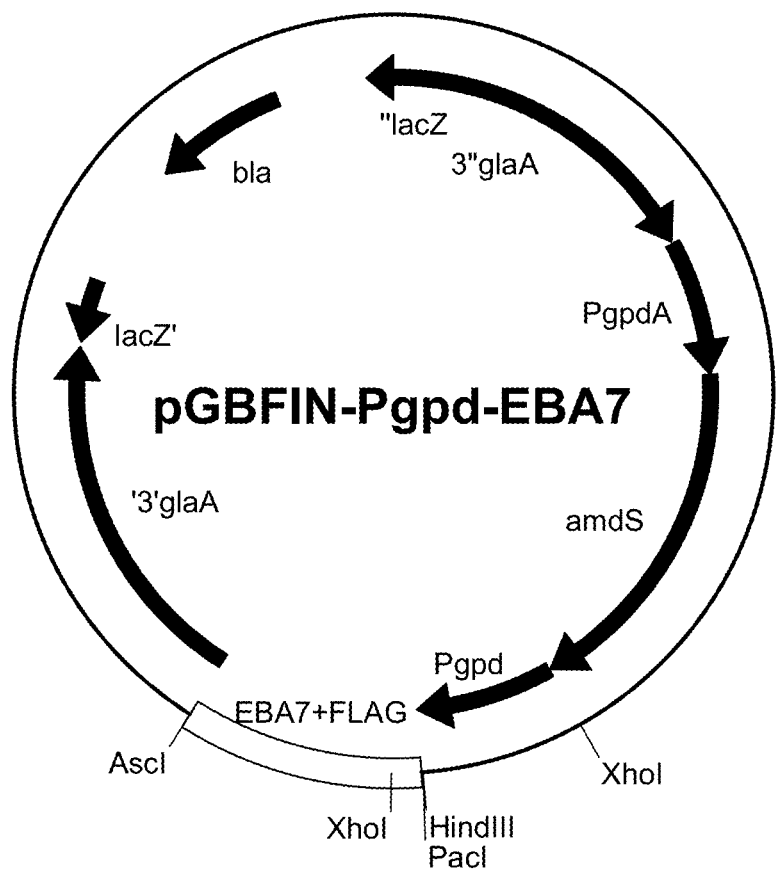

FIG. 5. Map of pGBFIN-Pgpd-EBA7 for expression of FLAG-tagged *T. emersonii* beta-glucanase CEB protein under control of the gpd promoter. pGBFIN-Pgpd-EBA7 is a pGBFIN38-based plasmid. Depicted are the FLAG-tagged *T.*

*emersonii* beta-glucanase CEB protein (EBA7+FLAG) expressed from the *Aspergillus nidulans* glyceraldehyde-3-phosphate dehydrogenase promoter (Pgpd). In addition, the selection marker gene (amdS), expressed from the *Aspergillus nidulans* glyceraldehyde-3-phosphate dehydrogenease promoter (Pgpd) and the glucoamylase flanks (3' glaA and 3"glaA) of the expression cassette are depicted.

Figure 6:
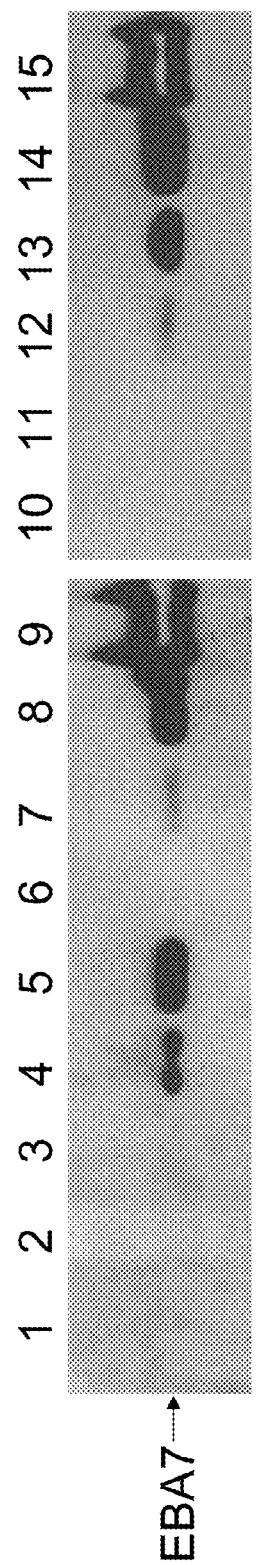

FIG. 6. Comparison of *T. emersonii* beta-glucanase CEB protein expression in *T. emersonii* under control of either the *A. niger* glaA promoter or the *A. nidulans* gpd promoter.

Western blot showing FLAG-tagged *T. emersonii* beta-glucanase CEB protein, expressed in *T. emersonii*. Lanes 1, 10 and 11 contain 15 µl (lane 1), 15 µl of 10 times diluted supernatant (lane 10) and 5 µl (lane 11) of supernatant of a 72 hours culture of an empty strain; lanes 3-5 contain 15 µl of 10 times diluted supernatant (lane 3), 5 µl (lane 4) and 15 µl (lane 5) of supernatant of *T. emersonii* pGBFIN-Pgpd-EBA7 transformant 8#14 harvested from a 72 hours culture; lanes 6-8 contain 15 µl of 10 times diluted supernatant (lane 6), 5 µl (lane 7) and 15 µl (lane 8) of supernatant of *T. emersonii* pGBFIN-Pgpd-EBA7 transformant 8#18 harvested from a 72 hours culture; lanes 12-14 contain 15 µl of 10 times diluted supernatant (lane 12), 5 µl (lane 13) and 15 µl (lane 14) of supernatant of *T. emersonii* pGBFIN-Pgpd-EBA7 transformant 8#32 harvested from a 72 hours culture; lanes 9 and 15 contain 15 µl of 100 times diluted supernatant of *T. emersonii* pGBFINEBA7 transformant 1#6 (glaA promoter) harvested from a 72 hours culture (due to the strong signal the bands are overexposed); lane 2 contains a molecular weight marker.

Figure 7:
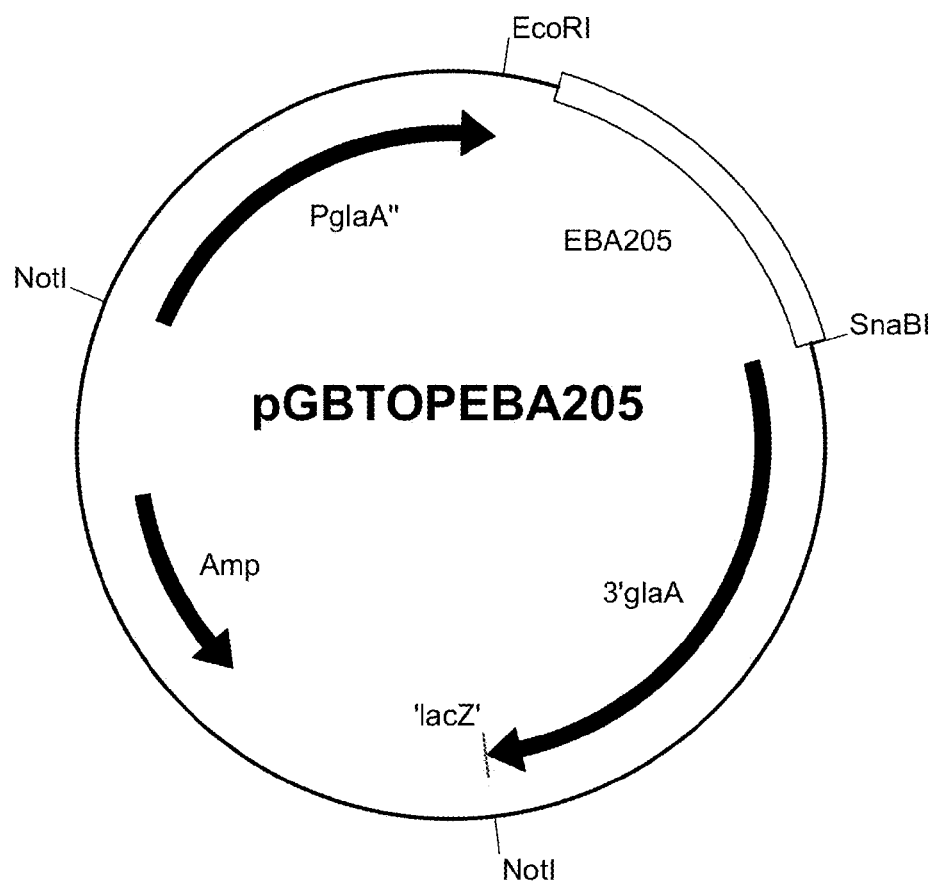

FIG. 7: Map of pGBTOPEBA205 for expression of *T. emersonii* CBHI in *T. emersonii*. Depicted are EBA205 expressed from the glucoamylase promoter (PglaA). In addition, the glucoamylase flank (3' glaA) of the expression cassette is depicted.

Figure 8:
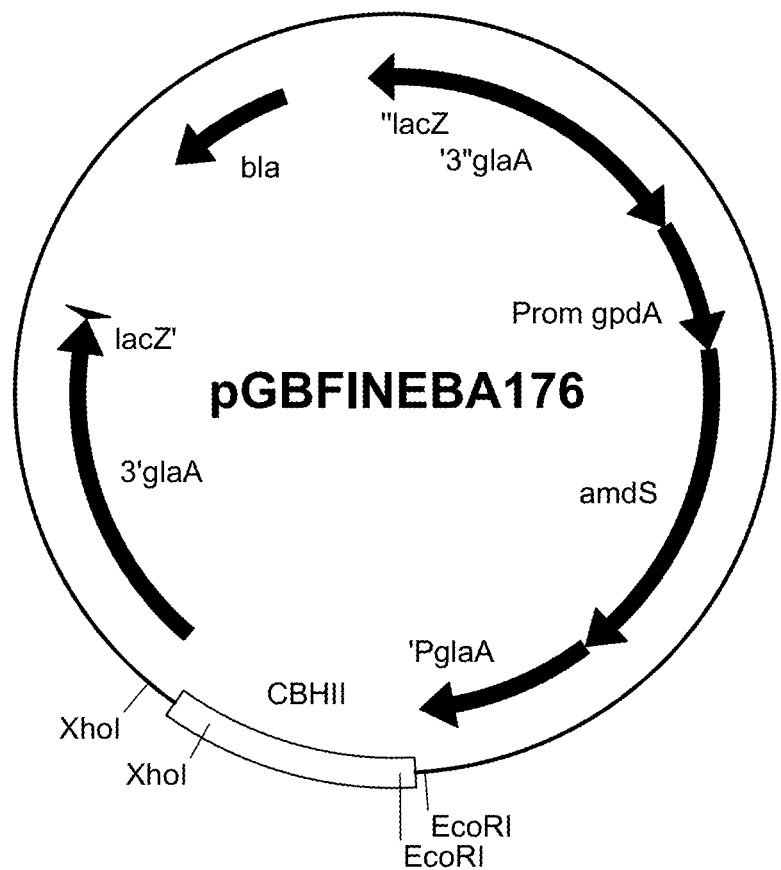

FIG. 8: Map of pGBFINEBA176 for expression of *T. emersonii* CBHI in *T. emersonii*. pGBFINEBA176 is a pGBFIN11-based plasmid. Depicted is the EBA176 gene expressed from the glucoamylase promoter (PglaA). In addition, the selection marker gene (amdS), expressed from the *Aspergillus nidulans* glyceraldehyde-3-phosphate dehydrogenease promoter (Pgpd) and the glucoamylase flanks (3' glaA and 3"glaA) of the expression cassette are depicted.

FIG. 9. Detection of multiple recombinant *T. emersonii* cellulases in *T. emersonii*.

(9A). SDS-PAGE detection of *T. emersonii* cellulases expressed in *T. emersonii*. *T. emersonii* was transformed with a mix of pGBTOPEBA4, pGBTOPEBA8, pGBFINEBA176, and pGBTOPEBA205. Approximately 400 transformants were grown in 96-well plates and screened for expression of at least one cellulase by E-PAGE gel analysis. Interesting transformants were grown in shake flasks containing glucose-based medium and proteins in supernatants harvested from 72 hours cultures were TCA-precipitated and analysed by SDS-PAGE analysis. FBG142 is the empty strain.

(9B). Graph showing WSU activity in transformants. Transformants were grown for 72 hours in glucose-based medium and WSU activity was determined in 16-times diluted supernatants of the cultures. FBG142 is the empty strain.

BRIEF DESCRIPTION OF THE SEQUENCE LISTING

SEQ ID NO: 1 sets out the DNA sequence of PCR primer 1;
SEQ ID NO: 2 sets out the DNA sequence of PCR primer 2;
SEQ ID NO: 3 sets out the amino acid sequence of the FLAG-tagged *T. emersonii* β-glucanase CEB (protein);
SEQ ID NO: 4 sets out the coding sequence of the FLAG-tagged *T. emersonii* β-glucanase CEB (DNA, coding region);
SEQ ID NO: 5 sets out the DNA sequence of PCR primer 3;
SEQ ID NO: 6 sets out the DNA sequence of PCR primer 4;
SEQ ID NO: 7 sets out the sequence of gpd promoter and Kozak sequence, the gpd promoter has residues: 1-870, the restriction enzyme sites, residues: 871-882 and the Kozak sequence: residues:883-892;
SEQ ID NO: 8 sets out the DNA sequence of PCR primer 5;
SEQ ID NO: 9 sets out the DNA sequence of PCR primer 6;
SEQ ID NO: 10 sets out the amino acid sequence of *T. emersonii* cellobiohydrolase I;
SEQ ID NO: 11 sets out the coding sequence *T. emersonii* GBH (DNA, coding region)
SEQ ID NO: 12 sets out the amino acid sequence of *T. emersonii* β-glucanase CEA (protein);
SEQ ID NO: 13 sets out the coding sequence of *T. emersonii* β-glucanase CEA (DNA, coding region)
SEQ ID NO: 14 sets out the amino acid sequence of *T. emersonii* β-glucosidase (protein)
SEQ ID NO: 15 sets out the coding sequence of *T. emersonii* β-glucosidase (DNA, coding region)
SEQ ID NO: 16 sets out the amino acid sequence of *T. emersonii* cellobiohydrolase II (protein)
SEQ ID NO: 17 sets out the coding sequence of *T. emersonii* cellobiohydrolase II (DNA, coding region), wild-type sequence.
SEQ ID NO: 18 sets out the aminoacid sequence of a Size 209 aa unknown protein from *T. emersonii*.
SEQ ID NO: 19 sets out the coding sequence of an unknown protein from *T. emersonii* having aminoacid sequence according to SEQ ID NO: 18.
SEQ ID NO: 20 sets out the aminoacid sequence of *T. emersonii* swollenin.
SEQ ID NO: 21 sets out the coding sequence of *T. emersonii* swollenin.
SEQ ID NO: 22 sets out the aminoacid sequence of *T. emersonii* acetyl xylan esterase.
SEQ ID NO: 23 sets out the coding sequence of *T. emersonii* acetyl xylan esterase.
SEQ ID NO: 24 sets out the aminoacid sequence of *T. emersonii* xylanase.
SEQ ID NO: 25 sets out the coding sequence of *T. emersonii* xylanase.

DETAILED DESCRIPTION OF A PREFERRED EMBODIMENT

Throughout the present specification and the accompanying claims, the words "comprise" and "include" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

According to the present invention it has now been shown that the above transformation techniques can be used to obtain a high level of expression of heterologous polypeptides or to enhance the production of homologous polypeptides in *Talaromyces*.

As used herein "transformant" means a cell that has been the object of transformation. "Transformant" and "recombinant cell" are herein used as synonyms.

"Transformation" herein means the genetic alteration of a cell by means of recombinant technology. It may result in the uptake, incorporation, and expression of genetic material (DNA, RNA or protein) or mutation or deletion of genetic material in the cell, through human intervention.

Nucleic acid construct: The term "nucleic acid construct" as used herein refers to a nucleic acid molecule, either single- or double-stranded, which is isolated from a naturally occurring gene or which has been modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

As used herein, the terms "gene" and "recombinant gene" refer to nucleic acid molecules which may be isolated from chromosomal DNA, which include an open reading frame encoding a polypeptide, e.g. cellulase, for instance a cellobiohydrolase.

A gene may include coding sequences, non-coding sequences, introns and/or regulatory sequences. Moreover, the term "gene" may refer to an isolated nucleic acid molecule as defined herein.

As used herein the expression "heterologous polypeptides" means polypeptides not produced by *Talaromyces* whereas "homologous polypeptides" means polypeptides produced by *Talaromyces* itself. Substrate (also called feedstock) herein is used to refer to a substance that comprises carbohydrate material, which may be treated with enzymes according to the invention, so that the carbohydrate material therein is modified. In addition to the carbohydrate material the substrate may contain any other component, including but not limited to non-carbohydrate material and starch. Carbohydrate in this context includes all saccharides, for example polysaccharides, oligosaccharides, disaccharides or monosaccharides. "Cellulase inducer" is herein defined as a compound that induces the production of cellulase in *Talaromyces*. Examples of cellulase inducers are pure cellulose cellobiose, sophorose and gentiobiose or any lignocellulosic material.

A polypeptide according to the invention may modify a carbohydrate material by chemically modifying or physically modifying such material. Chemical modification of the carbohydrate material may result in the degradation of such material, for example by hydrolysis, oxidation or other chemical modification such as by the action of a lyase. Physical modification may or may not be accompanied by chemical modification.

Different embodiments of the invention are described in more detail below.

*Talaromyces* Transformants

The invention provides *Talaromyces* Transformants. The *Talaromyces* Transformants are prepared by transformation of a *Talaromyces* host, such as *Talaromyces emersonii* with recombinantly introduced DNA. As indicated above, the invention provides a *Talaromyces* transformant capable of producing cellulase in the absence of cellulase inducer in a glucose medium, having a cellulase activity of 2 WSU/ml or more in 16 times diluted supernatant or broth or even more diluted supernatant or broth. In an embodiment the *Talaromyces* transformant has a cellulase activity of 3 WSU/ml or more in 16 times diluted supernatant or broth or even more diluted supernatant or broth, in a further embodiment 5 WSU/ml or more in 16 times diluted supernatant or broth or even more diluted supernatant or broth. In further embodiment the *Talaromyces* transformant has a cellulase activity of 2 or more WSU/ml in 16 to 10000 times diluted supernatant or broth, 3 or more WSU in a 16 times to 5000 times diluted supernatant or broth, 3 or more WSU/ml in a 16 times to 2500 times diluted supernatant or broth.

In one embodiment the *Talaromyces* transformant has an endoglucanase activity of 50 WBCU/ml or more.

In an embodiment, the *Talaromyces* transformant has a total cellulase content as determined by APEX of 38% or more, 39% or more, 40% or more, 41% or more, 42% or more, 43% or more, 44% or more, 45% or more, 46% or more, 47% or more and/or 48% or more.

In a further embodiment, the *Talaromyces* transformants according to any of claims 1 to 4, harbouring two or more recombinant genes capable of expressing cellulase. *Talaromyces* transformants according to the invention, wherein the two or more genes capable of expressing cellulase include cellobiohydrolase, endoglucanase and/or beta-glucosidase gene.

The invention also includes an embodiment of a *Talaromyces* transformant wherein the cellobiohydrolyse gene is cellobiohydrolase I and/or cellobiohydrolase II. In an embodiment, in the *Talaromyces* transformant one of more genes is integrated into the genome of the *Talaromyces*. The *Talaromyces* transformant is marker-free in a further embodiment.

Host Cells

The host cells used according to the invention are cells of the genus *Talaromyces*. Preferably the *Talaromyces* host is a *Talaromyces emersonii*, *Talaromyces stipitatus*, *Talaromyces marxianus* or *Talaromyces flavus*. In an embodiment the host is *Talaromyces emersonii*, e.g. *Talaromyces emersonii* ATCC16479.

Transformation

Transformation of the host may be conducted by any suitable known methods, including e.g. electroporation methods, particle bombardment or microprojectile bombardment, protoplast methods and *Agrobacterium* mediated transformation (AMT). Preferably the protoplast method is used. Procedures for transformation are described by J. R. S. Fincham, Transformation in fungi. 1989, microbiological reviews. 53, 148-170.

To obtain transformants using the protoplast method the transformation protocol has to be optimised. For generation of protoplasts mycelium is harvested from cultures grown for 8 up to 72 hours, preferably 14 to 24 hours. The mycelium is resuspended in a buffer containing an osmotic stabiliser and a lytic enzyme preparation. An osmotic stabiliser may be selected from the group including, but not limited to, sucrose, sorbitol, mannitol, KCl, $NH_4Cl$, NaCl, $MgSO_4$, and NaCl, preferably sucrose, sorbitol or KCl, at a concentration of 0.4-1.4 M, preferably 0.8 to 1.2, most preferably 1.0 M. Lytic enzyme preparations may be selected from the group including, but not limited to, Glucanex 200G, Novozyme 234, Caylase C3, Zymolyase, and Driselase, preferably Glucanex 200G. The digestion can be carried out at a temperature in between 30° C. and 37° C. in a rotary shaker for 1 to 3 hours. Protoplasts can be separated from mycelium using a Miracloth filter, sintered glass filter, cheesecloth, 30 µm screen, or a sorbitol cushion, centrifugation, and mycelium is allowed to settle and protoplasts are harvested by decantation. After washing the protoplasts in buffer with osmotic stabilizer, $10^4$ to $10^9$ protoplasts are added to 0.1-40 µg of DNA, and, optionally a nuclease inhibitor such as Aurintricarboxylic acid, in a buffer containing an osmotic stabiliser and 10-50 mM $CaCl_2$, preferably 50 mM $CaCl_2$. Optionally, the mixture is incubated for 15-30 minutes at 4° C. or at room temperature. Polyethylene glycol (PEG4000, PEG6000 or PEG8000, preferably PEG4000) is added to the mixture with a final concentration of 6 to 55%. Addition of PEG may be performed in sequential steps in which the PEG concentration is gradually increased. In between PEG additions the suspension is incubated for 5-30 minutes at 4° C.-37° C. Preferably, 6% PEG4000 (final concentration) is added to the protoplast and DNA suspension, incubated for 10 minutes at room temperature, and subsequently a second amount of PEG4000 is added up to a final concentration of 51% followed by an incubation of 15 minutes at 25° C. An aliquot of the mixture is either directly added to soft agar and poured on selective regeneration plates, or protoplasts are washed and plated on selective regeneration plates. Soft agar contains growth medium with an osmotic stabiliser with or without selection marker and a low concentration of agar that allows pouring the agar at 40° C.-60° C. Regeneration medium contains growth medium with an osmotic stabiliser, which may be the same osmotic stabiliser as used for protoplast formation.

The polynucleotide may be DNA, RNA or protein. In case of DNA, a vector is used with promoter, coding region, and terminator sequence, a so-called expression cassette. Using the desired polynucleotide sequence as a hybridization probe, nucleic acid molecules (i.e. genes) according to the invention can be isolated using standard hybridization and cloning techniques (e. g., as described in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989).

A nucleic acid may be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis.

Furthermore, oligonucleotides corresponding to or hybridizable to a nucleotide sequence according to the invention can be prepared by standard synthetic techniques, e.g., using an automated DNA synthesizer.

Depending on the desired functionality, the result of the transformation process according to the invention may be (heterologous) expression, over-expression, controlled regulation and/or deletion of particular genes. The poly or oligo nucleotides herein may be synthetic polynucleotides.

Introduction of genes into the host may be episomal, using a plasmid with the gene of interest, or the gene may be integrated into the genome of the host during the transformation process in one or more copies. Corresponding expression constructs can be made.

In an embodiment of the invention the transformation process is conducted as a co-transformation, i.e. transformation with two or more types of recombinant DNA. For instance, co-transformation may be executed with a) a vector containing a marker and b) a vector containing one or more genes of interest.

In an embodiment of the invention, transformation may use libraries of DNA, genomic DNA, RNA, cDNA or proteins.

The transformation of the *Talaromyces* host is conducted with a selection marker. For stable transformation of the *Talaromyces* cells, we have found that, depending upon the expression vector and transfection technique used, only a small fraction of cells may integrate the foreign DNA into their genome. In order to identify and select these integrants, a gene that encodes a selection marker (e.g., resistance to antibiotics) is generally introduced into the host cells along with the gene of interest. Suitable selection markers are for instance amdS, argB (ornithine carbamoyltransferase), bar (phoshinothricin acetyltransferase), carboxin resistance, hemA (5-aminolevulinate), hemB (porphobilinogen synthase), ble (phleomicin resistance), hygB (hygroycin phosphotransferase), natR (nourseothricin resistance), niaD (nitrate reductase), pyrG (orotidine-5'-phosphate decarboxylase), DHFR, sC (sulfate adenyltransferase), trpC (anthranilate synthase), pyroA, riboB. Suitable for use in a *Talaromyces* cell are the amdS gene (EP 635574 B1, WO 97/06261), ble gene (Mattern, I. E., Punt, P. J., Van den Hondel, C. A. M. J. J., 1988. A vector of *Aspergillus* transformation conferring phleomycin resistance. Fungal Genet. Newsl. 35, 25), and hygB gene (Punt P. J., Oliver R. P., Dingemanse M. A., Pouwels P. H., van den Hondel C. A. M. J. J., 1987. Transformation of *Aspergillus* based on the hygromycin B resistance marker from *Escherichia coli*. Gene. 56:117-24). In one embodiment, an amdS gene is used, e.g. an amdS gene from *A. nidulans* or *A. niger*. In an embodiment, the selection marker gene is the *A. nidulans* amdS coding sequence fused to the *A. nidulans* gpdA promoter (see EP 635574 B1). AmdS genes from other filamentous fungi may also be used (WO 97/06261).

More specifically it has been shown that selection for *Talaromyces* strains transformed with DNA encoding a desired polypeptide is possible by use of the marker genes used for transformation of *A. niger*. Due to the phylogenetic distance between the latter fungus and *Talaromyces* this could not be foreseen.

In an embodiment, the transformation may be performed more than one time, i.e. a transformed strain may be transformed again, once, twice or more times. In an embodiment thereof, the host for transformation in a second transformation is the *Talaromyces* transformant isolated from a first transformation, and similarly a preceding strain is the *Talaromyces* host for subsequent transformation in multiple transformations. In an embodiment thereof another marker may be used in one or more different steps of transformation, for example use of phleomycin and hygromycin as different markers. The resulting strains of multiples transformations are herein designated as multiple transformants. Accordingly, in an embodiment, the invention relates to a process for production of a *Talaromyces* multiple transformant, wherein in a first transformation isolated *Talaromyces* transformant is used as *Talaromyces* host and is transformed in a second transformation and in step (e) of the second transformation a *Talaromyces* multiple transformant is isolated.

In an embodiment, in the first transformation a different selection marker is used than in the second transformation for example use of phleomycin and hygromycin as different markers.

In an embodiment the selection marker is deleted from the transformed host cell after introduction of the expression construct so as to obtain transformed host cells capable of producing the polypeptide which are free of selection marker genes, i.e. marker-free. Such approach is described in EP 0

Vectors

Polynucleotides of the invention can be incorporated into a recombinant replicable vector, for example a cloning or expression vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells are described below.

Therefore a further aspect of the invention pertains to vectors, including cloning and expression vectors, comprising a polynucleotide of the invention encoding a polypeptide or a functional equivalent thereof and methods of growing, transforming or transfecting such vectors in a suitable host cell, for example under conditions in which expression of a polypeptide of the invention occurs. As used herein, the term "vector" refers to a nucleic acid molecule capable of transporting another nucleic acid to which it has been linked.

Vectors may be used in vitro, for example for the production of RNA or used to transfect or transform a host cell.

The vector may further include sequences flanking the polynucleotide which comprise sequences homologous to eukaryotic genomic sequences or viral genomic sequences. This will allow the introduction of the polynucleotides of the invention into the genome of a host cell.

The vector system may be a single vector, such as a single plasmid, or two or more vectors, such as two or more plasmids, which together contain the total DNA to be introduced into the genome of the host cell.

The vector into which the expression cassette or polynucleotide of the invention is inserted may be any vector which may conveniently be subjected to recombinant DNA procedures, and the choice of the vector will often depend on the host cell into which it is to be introduced.

A vector according to the invention may be an autonomously replicating vector, i.e. a vector which exists as an extra-chromosomal entity, the replication of which is independent of chromosomal replication, e. g. a plasmid. Alternatively, the vector may be one which, when introduced into a host cell, is integrated into the host cell genome and replicated together with the chromosome (s) into which it has been integrated.

One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. The terms "plasmid" and "vector" can be used interchangeably herein as the plasmid is the most commonly used form of vector. However, the invention is intended to include such other forms of expression vectors, such as cosmid, viral vectors (e.g., replication defective retroviruses, adenoviruses and adeno-associated viruses) and phage vectors which serve equivalent functions.

Vectors according to the invention may be used in vitro, for example for the production of RNA or used to transfect or transform a host cell.

The vector or expression construct is preferably integrated in the genome of the host cell in order to obtain stable transformants. In a further embodiment, the vector or expression construct is a minichromosome, or an artificial chromosome. An autonomously maintained cloning vector may comprise the AMA1-sequence (see e.g. Aleksenko and Clutterbuck (1997), Fungal Genet. Biol. 21: 373-397). In case the expression constructs are integrated in the host cells genome, the constructs are either integrated at random loci in the genome, or at predetermined target loci using homologous recombination, in which case the target loci preferably comprise a highly expressed gene.

A vector of the invention may comprise two or more, for example three, four or five, polynucleotides of the invention, for example for overexpression.

The recombinant expression vectors of the invention comprise a nucleic acid of the invention in a form suitable for expression of the nucleic acid in a host cell, which means that the recombinant expression vector includes one or more regulatory sequences, selected on the basis of the host cells to be used for expression, which is operably linked to the nucleic acid sequence to be expressed.

Within a vector, such as an expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell), i.e. the term "operably linked" refers to a juxtaposition wherein the components described are in a relationship permitting them to function in their intended manner. A regulatory sequence such as a promoter, enhancer or other expression regulation signal "operably linked" to a coding sequence is positioned in such a way that expression of the coding sequence is achieved under condition compatible with the control sequences or the sequences are arranged so that they function in concert for their intended purpose, for example transcription initiates at a promoter and proceeds through the DNA sequence encoding the polypeptide.

A vector or expression construct for a given host cell may thus comprise the following elements operably linked to each other in a consecutive order from the 5'-end to 3'-end relative to the coding strand of the sequence encoding the polypeptide of the first invention: (1) a promoter sequence capable of directing transcription of the nucleotide sequence encoding the polypeptide in the given host cell; translation initiation sequence including Kozak (see WO2006/077258) (2) optionally, a signal sequence capable of directing secretion of the polypeptide from the given host cell into a culture medium; optionally, a pre-pro-sequence for efficient secretion (3) a DNA sequence of the invention encoding a mature and preferably active form of a polypeptide having cellulase activity; and preferably also (4) a transcription termination region (terminator) capable of terminating transcription downstream of the nucleotide sequence encoding the polypeptide. See also optimal translation termination signal in WO2006/07725. This also includes a poly Adenylation signal for poly A+ mRNA generation. The control sequence may also be a polyadenylation sequence, a sequence which is operably linked to the 3'-terminus of the nucleic acid sequence and which, when transcribed, is recognized by the filamentous fungal cell as a signal to add polyadenosine residues to transcribed mRNA. Any polyadenylation sequence, which is functional in the cell, may be used in the present invention. Optional polyadenylation sequences for filamentous fungal cells are obtained from the genes encoding *A. oryzae* TAKA amylase, *A. niger* glucoamylase, *A. nidulans* anthranilate synthase, *Fusarium oxysporum* trypsin-like protease and *A. niger* alpha-glucosidase. The control sequence may also be a suitable transcription terminator sequence, a sequence recognized by a filamentous fungal cell to terminate transcription. The terminator sequence is operably linked to the 3'-terminus of the nucleic acid sequence encoding the polypeptide. Any terminator, which is functional in the cell, may be used in the present invention.

Optional terminators for filamentous fungal cells are obtained from the genes encoding *A. oryzae* TAKA amylase, *A. niger* glucoamylase (glaA), *A. nidulans* anthranilate synthase, *A. niger* alpha-glucosidase, trpC gene and *Fusarium oxysporum* trypsin-like protease.

Downstream of the nucleotide sequence according to the invention there may be a 3' untranslated region containing one or more transcription termination sites (e. g. a terminator). The origin of the terminator is less critical. The terminator can, for example, be native to the DNA sequence encoding the polypeptide. Preferably a filamentous fungal terminator is used in filamentous fungal host cells. More preferably, the terminator is endogenous to the host cell (in which the nucleotide sequence encoding the polypeptide is to be expressed).

In the transcribed region, a ribosome binding site for translation may be present. The coding portion of the mature transcripts expressed by the constructs will include a translation initiating AUG at the beginning and a termination codon appropriately positioned at the end of the polypeptide to be translated. See also remarks about Kozak and stop as in WO2006/07725)

The term "promoter" is defined herein as a DNA sequence that binds RNA polymerase and directs the polymerase to the correct downstream transcriptional start site of a nucleic acid sequence encoding a biological compound to initiate transcription. RNA polymerase effectively catalyzes the assembly of messenger RNA complementary to the appropriate DNA strand of a coding region. The term "promoter" will also be understood to include the 5'-non-coding region (between promoter and translation start) for translation after transcription into mRNA, cis-acting transcription control elements such as enhancers, and other nucleotide sequences capable of interacting with transcription factors. The promoter may be any appropriate promoter sequence suitable for a eukaryotic or prokaryotic host cell, which shows transcriptional activity, including mutant, truncated, and hybrid promoters, and may be obtained from genes encoding extra-cellular or intracellular polypeptides either homologous (native) or heterologous (foreign) to the cell. The promoter may be a constitutive or inducible promoter. Examples of inducible promoters that can be used are a starch-, copper-, oleic acid-inducible promoters. The promoter may be selected from the group, which includes but is not limited to promoters obtained from the genes encoding *A. oryzae* TAKA amylase, *Rhizomucor miehei* aspartic proteinase, *A. niger* neutral alpha-amylase, *A. niger* acid stable alpha-amylase, *A. niger* or *A. awamori* glucoamylase (glaA), *R. miehei* lipase, *A. oryzae* alkaline protease, *A. oryzae* triose phosphate isomerase, *A. nidulans* acetamidase, the NA2-tpi promoter (a hybrid of the promoters from the genes encoding *A. niger* neutral alpha-amylase and *A. oryzae* triose phosphate isomerase), promoters obtained from the genes encoding cbh1, cbh2, eg1, eg2, eg3, eg5, eg6, xln1, xln2 or xyl1, and mutant, truncated, and hybrid promoters thereof. In an embodiment, the promoter is chosen from the promoter of the DNA sequence encoding the polypeptide or a heterologous promoter chosen from the group consisting of: promoters of *A. niger* glaA, *T. emersonii* cbh1, and *T. emersonii* bg, or functional parts thereof optionally preceded by upstream activating sequences.

In a further embodiment, promoters for use in filamentous fungal cells are a promoter, or a functional part thereof, from a protease gene; e. g., from the *F. oxysporum* trypsin-like protease gene (U.S. Pat. No. 4,288,627), *A. oryzae* alkaline protease gene (alp), *A. niger* pacA gene, *A. oryzae* alkaline protease gene, *A. oryzae* neutral metalloprotease gene, *A. niger* aspergillopepsin protease pepA gene, or *F. venenatum* trypsin gene, *A. niger* aspartic protease pepB gene. Other promoters are the promoters described in WO2006/092396 and WO2005/100573, which are herein incorporated by reference.

The use of multiple promoters in a single strain is described in WO 2008/098933. The teaching of WO 2008/098933 may be applied herein.

It will be appreciated by those skilled in the art that the design of the expression vector can depend on such factors as the level of expression of polypeptide desired, etc. The vectors, such as expression vectors, of the invention can be introduced into host cells to thereby produce polypeptides or peptides, encoded by nucleic acids as described herein (e.g. polypeptides, mutant forms of polypeptides, fragments, variants or functional equivalents thereof. Accordingly, expression vectors useful in the present invention include chromosomal-, episomal- and virus-derived vectors e.g., vectors derived from bacterial plasmids, bacteriophage, yeast episome, yeast chromosomal elements, viruses such as baculoviruses, papova viruses, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. According to the invention, culture medium is used as described herein in the examples and culture conditions as described in the examples or alternative medium and cultures conditions that have similar performance.

Integration

According to an embodiment of the invention integration is achieved. In such embodiment, an integrative cloning vector may integrate at random or at a predetermined target locus in the chromosome(s) of the host cell into which it is to be integrated. In an embodiment of the invention, an integrative cloning vector may comprise a DNA fragment which is homologous to a DNA sequence in a predetermined target locus in the genome of host cell for targeting the integration of the cloning vector to this predetermined locus. In order to promote targeted integration, the cloning vector may be preferably linearized prior to transformation of the host cell. Linearization may preferably be performed such that at least one but preferably either end of the cloning vector is flanked by sequences homologous to the target locus. The length of the homologous sequences flanking the target locus is preferably at least about 0.1 kb, such as about at least 0.2 kb, more preferably at least about 0.5 kb, even more preferably at least about 1 kb, most preferably at least about 2 kb. Preferably, the parent host strains may be modified for improved frequency of targeted DNA integration as described in WO05/095624 and/or WO2007/115886.

Preferably, the efficiency of targeted integration into the genome of the host cell, i.e. integration in a predetermined target locus, is increased by augmented homologous recombination abilities of the host cell. Such phenotype of the cell preferably involves a deficient hdfA or hdfB gene as described in WO2005/095624. WO2005/095624 discloses a method to obtain a filamentous fungal cell comprising increased efficiency of targeted integration.

The vector may contain a polynucleotide of the invention oriented in an antisense direction to provide for the production of antisense RNA. The synthetic polynucleotides may be optimized in codon use, preferably according to the methods described in WO2006/077258 and/or PCT/EP2007/055943, which are herein incorporated by reference. PCT/EP2007/055943 addresses codon-pair optimization. Codon-pair optimization is a method wherein the nucleotide sequences encoding a polypeptide have been modified with respect to their codon-usage, in particular the codon-pairs that are used, to obtain improved expression of the nucleotide sequence encoding the polypeptide and/or improved production of the encoded polypeptide. Codon pairs are defined as sets of two subsequent triplets (codons) in a coding sequence.

Engineering Embodiments

When the polypeptide according to the invention is to be secreted from the host cell into the cultivation medium, an appropriate signal sequence can be added to the polypeptide in order to direct the de novo synthesized polypeptide to the secretion route of the host cell. The person skilled in the art knows to select an appropriate signal sequence for a specific host. The signal sequence may be native to the host cell, or may be foreign to the host cell. As an example, a signal sequence from a polypeptide native to the host cell can be used. Preferably, said native polypeptide is a highly secreted polypeptide, i.e. a polypeptide that is secreted in amounts higher than 10% of the total amount of polypeptide being secreted.

As an alternative for a signal sequence, the polypeptide of the invention can be fused to a secreted carrier polypeptide, or part thereof. Such chimeric construct is directed to the secretion route by means of the signal sequence of the carrier polypeptide, or part thereof. In addition, the carrier polypeptide will provide a stabilizing effect to the polypeptide according to the invention and or may enhance solubility. Such carrier polypeptide may be any polypeptide. Preferably, a highly secreted polypeptide is used as a carrier polypeptide. The carrier polypeptide may be native or foreign to the polypeptide according to the invention. The carrier polypeptide may be native of may be foreign to the host cell. Examples of such carrier polypeptides are glucoamylase, pre-pro sequence of alpha-Mating factor, cellulose binding domain of *Clostridium cellulovorans* cellulose binding polypeptide A, glutathione S-transferase, chitin binding domain of *Bacillus circulans* chitinase A1, maltose binding domain encoded by the malE gene of *E. coli* K12, beta-galactosidase, and alkaline phosphatase. An optional carrier polypeptide for expression of such chimeric construct in *Aspergillus* cells is glucoamylase. The carrier polypeptide and polypeptide according to the invention may contain a specific amino acid motif to facilitate isolation of the polypeptide; the polypeptide according to the invention may be released by a special releasing agent. The releasing agent may be a proteolytic enzyme or a chemical agent. An example of such amino acid motif is the KEX protease cleavage site, which is well-known to the person skilled in the art.

A signal sequence can be used to facilitate secretion and isolation of a polypeptide or polypeptide of the invention. Signal sequences are typically characterized by a core of hydrophobic amino acids, which are generally cleaved from the mature polypeptide during secretion in one or more cleavage events. Such signal peptides contain processing sites that allow cleavage of the signal sequence from the mature polypeptides as they pass through the secretory pathway. The signal sequence directs secretion of the polypeptide, such as from a eukaryotic host into which the expression vector is transformed, and the signal sequence is subsequently or concurrently cleaved. The polypeptide can then be readily purified from the extracellular medium by known methods. Alternatively, the signal sequence can be linked to the polypeptide of interest using a sequence, which facilitates purification, such as with a GST domain. Thus, for instance, the sequence encoding the polypeptide may be fused to a marker sequence, such as a sequence encoding a peptide, which facilitates purification of the fused polypeptide. In certain embodiments of this aspect of the invention, the marker sequence is a hexa-histidine peptide, such as the tag provided in a pQE vector (Qiagen, Inc.), among others, many of which are commercially available. As described in Gentz et al, *Proc. Natl. Acad. Sci. USA* 86:821-824 (1989), for instance, hexa-histidine provides for convenient purification of the fusion polypeptide. The HA tag is another peptide useful for purification which corresponds to an epitope derived of influenza hemaglutinin polypeptide, which has been described by Wilson et al., *Cell* 37:767 (1984), for instance.

Generally, the transformant may be constructed by reducing or eliminating expression of certain genes.

Reduction or deletion of these genes may be advantageous since it may increase the yield of desirable polypeptides and may also reduce break-down of desirable polypeptides under influence of polypeptide expressed by the reduced or deleted gene. The reduction or deletion may be accomplished using one or more methods well known in the art, for example, insertions, disruptions, replacements, or deletions. Methods for reduction or deletion can be site-directed or random mutagenesis methods. The portion of the gene to be modified or inactivated may be, for example, the coding region or a regulatory element required for expression of the coding region. An example of such a regulatory or control sequence of a gene may be a promoter sequence or a functional part thereof, i.e., a part which is sufficient for affecting expression of the gene. Other control sequences for possible modification include, but are not limited to, a leader, propeptide sequence, prepropeptide, Kozak, transcription initiation, signal sequence, transcription terminator, transcriptional activator, translational initiation site, and translational termination site.

In an embodiment, the polynucleotides of the present invention as described herein may be over-expressed in a microbial strain of the invention compared to the parent microbial strain in which said gene is not over-expressed. Over-expression of a polynucleotide sequence is defined herein as the expression of the said sequence gene which results in an activity of the enzyme encoded by the said sequence in a microbial strain being at least about 1.2-fold the activity of the enzyme in the parent microbial; at least 1.5-fold the activity, preferably the activity of said enzyme is at least about 2-fold, at least about 3-fold, at least about 4-fold, at least about 5-fold, at least about 10-fold, at least about 20-fold, at least about 50-fold, at least about 100-fold, at least about 200-fold, at least about 500-fold, at least about 1000-fold the activity of the enzyme in the parent microbial.

In one embodiment, a fusion polypeptide may be produced. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In a further embodiment, the fusion gene can be synthesized by conventional techniques including automated DNA synthesizers. Alternatively, PCR amplification of gene fragments can be carried out using anchor primers, which give rise to complementary overhangs between two consecutive gene fragments which can subsequently be annealed and reamplified to generate a chimeric gene sequence (see, for example, Current Protocols in Molecular Biology, eds. Ausubel et al. John Wiley & Sons: 1992). Moreover, many expression vectors are commercially available that already encode a fusion moiety (e.g, a GST polypeptide). An encoding nucleic acid can be cloned into such an expression vector such that the fusion moiety is linked in-frame to the polypeptide In such a way that the fused polypeptides are in frame and expression of the fused polypeptide is under control of the same promoter (s) and terminator. The hybrid polypeptides may comprise a combination of partial or complete polypeptide sequences obtained from at least two different polypeptides wherein one or more may be heterologous to the host cell.

Polypeptide Expression/Production

According to the invention the polypeptide is expressed by the *Talaromyces* transformant. The *Talaromyces* transformant may thus be used to in the preparation of a polypeptide according to the invention. Such a method comprises cultivating a host cell (e. g. transformed as described above) under conditions to provide for expression of a coding sequence encoding the polypeptide, and optionally recovering the expressed polypeptide.

In the context of the present invention, the term "recombinant" refers to any genetic modification not exclusively involving naturally occurring processes and/or genetic modifications induced by subjecting the host cell to random mutagenesis but also gene disruptions and/or deletions and/or specific mutagenesis, for example. Consequently, combinations of recombinant and naturally occurring processes and/or genetic modifications induced by subjecting the host cell to random mutagenesis are construed as being recombinant.

The recombinant *Talaromyces* cells (transformants) according to the invention may be cultured using procedures known in the art. For each combination of a promoter and a host cell, culture conditions are available which are conducive to the expression the DNA sequence encoding the polypeptide. After reaching the desired cell density or titre of the polypeptide the culture is stopped and the polypeptide is recovered using known procedures.

The fermentation medium can comprise a culture medium containing a carbon source (e. g. glucose, maltose, molasses, starch, cellulose, xylan, pectin, lignocellolytic biomass hydrolysate, etc.), a nitrogen source (e. g. ammonium sulphate, ammonium nitrate, ammonium chloride, etc.), an organic nitrogen source (e. g. yeast extract, malt extract, peptone, etc.) and inorganic nutrient sources (e. g. phosphate, magnesium, potassium, zinc, iron, etc.). Optionally, an inducer (e. g. cellulose, pectin, xylan, maltose, maltodextrin or xylogalacturonan) may be included.

The selection of the appropriate medium may be based on the choice of expression host and/or based on the regulatory requirements of the expression construct. Such media are known to those skilled in the art. The medium may, if desired, contain additional components favouring the transformed expression hosts over other potentially contaminating microorganisms.

The fermentation can be performed over a period of from about 0.5 to about 30 days. It may be a batch, fed-batch, or continuous process, suitably at a temperature in the range of, for example, from about 20 to about 90° C., preferably 20-55° C. more preferably 40-50° C. and/or at a pH, for example, from about 2 to about 8, preferably from about 3 to about 5. The appropriate conditions are usually selected based on the choice of the expression host and the polypeptide to be expressed.

After fermentation, if necessary, the cells can be removed from the fermentation broth by means of centrifugation or filtration. After fermentation has stopped or after removal of the cells, the polypeptide of the invention may then be recovered and, if desired, purified and isolated by conventional means.

Polypeptide/Polypeptide Compositions

The invention provides a polypeptide or polypeptide composition that comprises a cellulase and/or a hemicellulase and/or a pectinase.

Herein, a cellulase is any polypeptide which is capable of degrading or modifying cellulose and/or glucans. A polypeptide which is capable of degrading cellulose is one which is capable of catalysing the process of breaking down cellulose into smaller units, either partially, for example into cellodextrins, or completely into glucose monomers. A cellulase according to the invention may give rise to a mixed population of cellodextrins and glucose monomers when contacted with the cellulose. Such degradation will typically take place by way of a hydrolysis reaction.

Herein, a hemicellulase is any polypeptide which is capable of degrading or modifying hemicellulose. That is to say, a hemicellulase may be capable of degrading or modifying one or more of xylan, araban, glucuronoxylan, arabinogalactan, arabinoxylan, glucomannan, galactomannan and xyloglucan. A polypeptide which is capable of degrading a hemicellulose is one which is capable of catalysing the process of breaking down the hemicellulose into smaller polysaccharides, either partially, for example into oligosaccharides, or completely into sugar monomers, for example hexose or pentose sugar monomers. A hemicellulase according to the invention may give rise to a mixed population of oligosaccharides and sugar monomers when contacted with the hemicellulase. Such degradation will typically take place by way of a hydrolysis reaction.

Herein, a pectinase is any polypeptide which is capable of degrading or modifying pectin. A polypeptide which is capable of degrading pectin is one which is capable of catalysing the process of breaking down pectin into smaller units, either partially, for example into oligosaccharides, or completely into sugar monomers. A pectinase according to the invention may give rise to a mixed population of oligosacchardies and sugar monomers when contacted with the pectinase. Such degradation will typically take place by way of a hydrolysis reaction.

Accordingly, a composition of the invention may comprise any cellulase, for example, a cellobiohydrolase, an endo-$\beta$-1, 4-glucanase, a $\beta$-glucosidase or a $\beta$-(1,3)(1,4)-glucanase.

Herein, a cellobiohydrolase (EC 3.2.1.91) is any polypeptide which is capable of catalysing the hydrolysis of 1,4-β-D-glucosidic linkages in cellulose or cellotetraose, releasing cellobiose from the non-reducing ends of the chains. This enzyme may also be referred to as cellulase 1,4-β-cellobiosidase, 1,4-β-cellobiohydrolase, 1,4-β-D-glucan cellobiohydrolase, avicelase, exo-1,4-β-D-glucanase, exocellobiohydrolase or exoglucanase.

Herein, an endo-β-1,4-glucanase (EC 3.2.1.4) is any polypeptide which is capable of catalysing the endohydrolysis of 1,4-β-D-glucosidic linkages in cellulose, lichenin or cereal β-D-glucans. Such a polypeptide may also be capable of hydrolyzing 1,4-linkages in β-D-glucans also containing 1,3-linkages. This enzyme may also be referred to as cellulase, avicelase, β-1,4-endoglucan hydrolase, β-1,4-glucanase, carboxymethyl cellulase, celludextrinase, endo-1,4-β-D-glucanase, endo-1,4-β-D-glucanohydrolase, endo-1,4-β-glucanase or endoglucanase.

Herein, a β-glucosidase (EC 3.2.1.21) is any polypeptide which is capable of catalysing the hydrolysis of terminal, non-reducing β-D-glucose residues with release of β-D-glucose. Such a polypeptide may have a wide specificity for β-D-glucosides and may also hydrolyze one or more of the following: a β-D-galactoside, an α-L-arabinoside, a β-D-xyloside or a β-D-fucoside. This enzyme may also be referred to as amygdalase, β-D-glucoside glucohydrolase, cellobiase or gentobiase.

Herein a β-(1,3)(1,4)-glucanase (EC 3.2.1.73) is any polypeptide which is capable of catalyzing the hydrolysis of 1,4-β-D-glucosidic linkages in β-D-glucans containing 1,3- and 1,4-bonds. Such a polypeptide may act on lichenin and cereal β-D-glucans, but not on β-D-glucans containing only 1,3- or 1,4-bonds. This enzyme may also be referred to as licheninase, 1,3-1,4-β-D-glucan 4-glucanohydrolase, β-glucanase, endo-β-1,3-1,4 glucanase, lichenase or mixed linkage β-glucanase. An alternative for this type of enzyme is EC 3.2.1.6, which is described as endo-1,3(4)-beta-glucanase. This type of enzyme hydrolyses 1,3- or 1,4-linkages in beta-D-glucans when the glucose residue whose reducing group is involved in the linkage to be hydrolysed is itself substituted at C-3. Alternative names include endo-1,3-beta-glucanase, laminarinase, 1,3-(1,3;1,4)-beta-D-glucan 3 (4) glucanohydrolase; substrates include laminarin, lichenin and cereal beta-D-glucans.

A composition of the invention may comprise any hemicellulase, for example, an endoxylanase, a β-xylosidase, an α-L-arabinofuranosidase, an 1,4-beta-D-arabinoxylan arabinofuranohydrolase, an acetyl-xylan esterase, an α-D-glucuronidase, an cellobiohydrolase, a feruloyl esterase, a coumaroyl esterase, an α-galactosidase, a β-galactosidase, a β-mannanase or a β-mannosidase.

Herein, an endoxylanase (EC 3.2.1.8) is any polypeptide which is capable of catalyzing the endohydrolysis of 1,4-β-D-xylosidic linkages in xylans. This enzyme may also be referred to as endo-1,4-β-xylanase or 1,4-β-D-xylan xylanohydrolase. An alternative is EC 3.2.1.136, a glucuronoarabinoxylan endoxylanase, an enzyme that is able to hydrolyse 1,4 xylosidic linkages in glucuronoarabinoxylans.

Herein, a β-xylosidase (EC 3.2.1.37) is any polypeptide which is capable of catalyzing the hydrolysis of 1,4-β-D-xylans, to remove successive D-xylose residues from the non-reducing termini. Such enzymes may also hydrolyze xylobiose. This enzyme may also be referred to as xylan 1,4-β-xylosidase, 1,4-β-D-xylan xylohydrolase, exo-1,4-β-xylosidase or xylobiase.

Herein, an α-L-arabinofuranosidase (EC 3.2.1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase.

Herein, an α-D-glucuronidase (EC 3.2.1.139) is any polypeptide which is capable of catalyzing a reaction of the following form: alpha-D-glucuronoside+H(2)O=an alcohol+D-glucuronate. This enzyme may also be referred to as alpha-glucuronidase or alpha-glucosiduronase. These enzymes may also hydrolyse 4-O-methylated glucoronic acid, which can also be present as a substituent in xylans. Alternative is EC 3.2.1.131: xylan alpha-1,2-glucuronosidase, which catalyses the hydrolysis of alpha-1,2-(4-O-methyl)glucuronosyl links.

Herein, an cellobiohydrolase (EC 3.1.1.72) is any polypeptide which is capable of catalyzing the deacetylation of xylans and xylo-oligosaccharides. Such a polypeptide may catalyze the hydrolysis of acetyl groups from polymeric xylan, acetylated xylose, acetylated glucose, alpha-napthyl acetate or p-nitrophenyl acetate but, typically, not from triacetylglycerol. Such a polypeptide typically does not act on acetylated mannan or pectin.

Herein, an acetyl-xylan esterase (EC 3.1.1.6) is any polypeptide which is capable of hydrolysis of specifically the ester linkages of the acetyl groups in positions 2 and/or 3 of the xylose moieties of natural xylan.

Herein, a feruloyl esterase (EC 3.1.1.73) is any polypeptide which is capable of catalyzing a reaction of the form: feruloyl-saccharide+H(2)O=ferulate+saccharide. The saccharide may be, for example, an oligosaccharide or a polysaccharide. It may typically catalyze the hydrolysis of the 4-hydroxy-3-methoxycinnamoyl (feruloyl) group from an esterified sugar, which is usually arabinose in 'natural' substrates. p-nitrophenol acetate and methyl ferulate are typically poorer substrates. This enzyme may also be referred to as cinnamoyl ester hydrolase, ferulic acid esterase or hydroxycinnamoyl esterase. It may also be referred to as a hemicellulase accessory enzyme, since it may help xylanases and pectinases to break down plant cell wall hemicellulose and pectin.

Herein, a coumaroyl esterase (EC 3.1.1.73) is any polypeptide which is capable of catalyzing a reaction of the form: coumaroyl-saccharide+H(2)O=coumarate+saccharide. The saccharide may be, for example, an oligosaccharide or a polysaccharide. This enzyme may also be referred to as trans-4-coumaroyl esterase, trans-p-coumaroyl esterase, p-coumaroyl esterase or p-coumaric acid esterase. This enzyme also falls within EC 3.1.1.73 so may also be referred to as a feruloyl esterase.

Herein, an α-galactosidase (EC 3.2.1.22) is any polypeptide which is capable of catalyzing the hydrolysis of terminal, non-reducing α-D-galactose residues in α-D-galactosides, including galactose oligosaccharides, galactomannans, galactans and arabinogalactans. Such a polypeptide may also be capable of hydrolyzing α-D-fucosides. This enzyme may also be referred to as melibiase.

Herein, a β-galactosidase (EC 3.2.1.23) is any polypeptide which is capable of catalyzing the hydrolysis of terminal non-reducing β-D-galactose residues in β-D-galactosides. Such a polypeptide may also be capable of hydrolyzing α-L-arabinosides. This enzyme may also be referred to as exo-(1→4)-β-D-galactanase or lactase.

Herein, a β-mannanase (EC 3.2.1.78) is any polypeptide which is capable of catalyzing the random hydrolysis of 1,4-β-D-mannosidic linkages in mannans, galactomannans and glucomannans. This enzyme may also be referred to as mannan endo-1,4-β-mannosidase or endo-1,4-mannanase.

Herein, a β-mannosidase (EC 3.2.1.25) is any polypeptide which is capable of catalyzing the hydrolysis of terminal, non-reducing β-D-mannose residues in β-D-mannosides. This enzyme may also be referred to as mannanase or mannase.

A composition of the invention may comprise any pectinase, for example an endo polygalacturonase, a pectin methyl esterase, an endo-galactanase, a beta galactosidase, a pectin acetyl esterase, an endo-pectin lyase, pectate lyase, alpha rhamnosidase, an exo-galacturonase, an exo-polygalacturonate lyase, a rhamnogalacturonan hydrolase, a rhamnogalacturonan lyase, a rhamnogalacturonan acetyl esterase, a rhamnogalacturonan galacturonohydrolase or a xylogalacturonase.

Herein, an endo-polygalacturonase (EC 3.2.1.15) is any polypeptide which is capable of catalyzing the random hydrolysis of 1,4-α-D-galactosiduronic linkages in pectate and other galacturonans. This enzyme may also be referred to as polygalacturonase pectin depolymerase, pectinase, endopolygalacturonase, pectolase, pectin hydrolase, pectin polygalacturonase, poly-α-1,4-galacturonide glycanohydrolase, endogalacturonase; endo-D-galacturonase or poly(1,4-α-D-galacturonide) glycanohydrolase.

Herein, a pectin methyl esterase (EC 3.1.1.11) is any enzyme which is capable of catalyzing the reaction: pectin+n $H_2O$=n methanol+pectate. The enzyme may also been known as pectinesterase, pectin demethoxylase, pectin methoxylase, pectin methylesterase, pectase, pectinoesterase or pectin pectylhydrolase.

Herein, an endo-galactanase (EC 3.2.1.89) is any enzyme capable of catalyzing the endohydrolysis of 1,4-β-D-galactosidic linkages in arabinogalactans. The enzyme may also be known as arabinogalactan endo-1,4-β-galactosidase, endo-1, 4-β-galactanase, galactanase, arabinogalactanase or arabinogalactan 4-β-D-galactanohydrolase.

Herein, a pectin acetyl esterase is defined herein as any enzyme which has an acetyl esterase activity which catalyzes the deacetylation of the acetyl groups at the hydroxyl groups of GalUA residues of pectin Herein, an endo-pectin lyase (EC 4.2.2.10) is any enzyme capable of catalyzing the eliminative cleavage of (1→4)-α-D-galacturonan methyl ester to give oligosaccharides with 4-deoxy-6-O-methyl-α-D-galact-4-enuronosyl groups at their non-reducing ends. The enzyme may also be known as pectin lyase, pectin trans-eliminase; endo-pectin lyase, polymethylgalacturonic transeliminase, pectin methyltranseliminase, pectolyase, PL, PNL or PMGL or (1→4)-6-O-methyl-α-D-galacturonan lyase.

Herein, a pectate lyase (EC 4.2.2.2) is any enzyme capable of catalyzing the eliminative cleavage of (1→4)-α-D-galacturonan to give oligosaccharides with 4-deoxy-α-D-galact-4-enuronosyl groups at their non-reducing ends. The enzyme may also be known polygalacturonic transeliminase, pectic acid transeliminase, polygalacturonate lyase, endopectin methyltranseliminase, pectate transeliminase, endogalacturonate transeliminase, pectic acid lyase, pectic lyase, α-1,4-D-endopolygalacturonic acid lyase, PGA lyase, PPase-N, endo-α-1,4-polygalacturonic acid lyase, polygalacturonic acid lyase, pectin trans-eliminase, polygalacturonic acid trans-eliminase or (1→4)-α-D-galacturonan lyase.

Herein, an alpha rhamnosidase (EC 3.2.1.40) is any polypeptide which is capable of catalyzing the hydrolysis of terminal non-reducing α-L-rhamnose residues in α-L-rhamnosides or alternatively in rhamnogalacturonan. This enzyme may also be known as α-L-rhamnosidase T, α-L-rhamnosidase N or α-L-rhamnoside rhamnohydrolase.

Herein, exo-galacturonase (EC 3.2.1.82) is any polypeptide capable of hydrolysis of pectic acid from the non-reducing end, releasing digalacturonate. The enzyme may also be known as exo-poly-α-galacturonosidase, exopolygalacturonosidase or exopolygalacturanosidase.

Herein, exo-galacturonase (EC 3.2.1.67) is any polypeptide capable of catalyzing: $(1,4-\alpha-D-galacturonide)_n+H_2O$= $(1,4-\alpha-D-galacturonide)_{n-1}$+D-galacturonate. The enzyme may also be known as galacturan 1,4-α-galacturonidase, exopolygalacturonase, poly(galacturonate) hydrolase, exo-D-galacturonase, exo-D-galacturonanase, exopoly-D-galacturonase or poly(1,4-α-D-galacturonide) galacturonohydrolase.

Herein, exopolygalacturonate lyase (EC 4.2.2.9) is any polypeptide capable of catalyzing eliminative cleavage of 4-(4-deoxy-α-D-galact-4-enuronosyl)-D-galacturonate from the reducing end of pectate, i.e. de-esterified pectin. This enzyme may be known as pectate disaccharide-lyase, pectate exo-lyase, exopectic acid transeliminase, exopectate lyase, exopolygalacturonic acid-trans-eliminase, PATE, exo-PATE, exo-PGL or (1→4)-α-D-galacturonan reducing-end-disaccharide-lyase.

Herein, rhamnogalacturonan hydrolase is any polypeptide which is capable of hydrolyzing the linkage between galactosyluronic acid and rhamnopyranosyl in an endo-fashion in strictly alternating rhamnogalacturonan structures, consisting of the disaccharide [(1,2-alpha-L-rhamnoyl-(1,4)-alpha-galactosyluronic acid].

Herein, rhamnogalacturonan lyase is any polypeptide which is any polypeptide which is capable of cleaving α-L-Rhap-(1→4)-α-D-GalpA linkages in an endo-fashion in rhamnogalacturonan by beta-elimination.

Herein, rhamnogalacturonan acetyl esterase is any polypeptide which catalyzes the deacetylation of the backbone of alternating rhamnose and galacturonic acid residues in rhamnogalacturonan.

Herein, rhamnogalacturonan galacturonohydrolase is any polypeptide which is capable of hydrolyzing galacturonic acid from the non-reducing end of strictly alternating rhamnogalacturonan structures in an exo-fashion.

Herein, xylogalacturonase is any polypeptide which acts on xylogalacturonan by cleaving the β-xylose substituted galacturonic acid backbone in an endo-manner. This enzyme may also be known as xylogalacturonan hydrolase.

Herein, an α-L-arabinofuranosidase (EC 3.2.1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase.

Herein, endo-arabinanase (EC 3.2.1.99) is any polypeptide which is capable of catalyzing endohydrolysis of 1,5-α-arabinofuranosidic linkages in 1,5-arabinans. The enzyme may also be know as endo-arabinase, arabinan endo-1,5-α-L-arabinosidase, endo-1,5-α-L-arabinanase, endo-α-1,5-arabanase; endo-arabanase or 1,5-α-L-arabinan 1,5-α-L-arabinanohydrolase.

A composition of the invention will typically comprise at least one cellulase and/or at least one hemicellulase and/or at least one pectinase (one of which is a polypeptide according to the invention). A composition of the invention may comprise a cellobiohydrolase, an endoglucanase and/or a β-glucosidase. Such a composition may also comprise one or more hemicellulases and/or one or more pectinases.

One or more (for example two, three, four or all) of an amylase, a protease, a lipase, a ligninase, a hexosyltransferase or a glucuronidase may be present in a composition of the invention.

"Protease" includes enzymes that hydrolyze peptide bonds (peptidases), as well as enzymes that hydrolyze bonds between peptides and other moieties, such as sugars (glycopeptidases). Many proteases are characterized under EC 3.4, and are suitable for use in the invention incorporated herein by reference. Some specific types of proteases include, cysteine proteases including pepsin, papain and serine proteases including chymotrypsins, carboxypeptidases and metalloendopeptidases.

"Lipase" includes enzymes that hydrolyze lipids, fatty acids, and acylglycerides, including phosphoglycerides, lipopolypeptides, diacylglycerols, and the like. In plants, lipids are used as structural components to limit water loss and pathogen infection. These lipids include waxes derived from fatty acids, as well as cutin and suberin.

"Ligninase" includes enzymes that can hydrolyze or break down the structure of lignin polymers. Enzymes that can break down lignin include lignin peroxidases, manganese peroxidases, laccases and feruloyl esterases, and other enzymes described in the art known to depolymerize or otherwise break lignin polymers. Also included are enzymes capable of hydrolyzing bonds formed between hemicellulosic sugars (notably arabinose) and lignin. Ligninases include but are not limited to the following group of enzymes: lignin peroxidases (EC 1.11.1), manganese peroxidases (EC 1.11.1.13), laccases (EC 1.10.3.2) and feruloyl esterases (EC 3.1.1.73).

"Hexosyltransferase" (2.4.1-) includes enzymes which are capable of transferring glycosyl groups, more specifically hexosyl groups. In addition to transfer of a glycosyl-group from a glycosyl-containing donor to another glycosyl-containing compound, the acceptor, the enzymes can also transfer the glycosyl-group to water as an acceptor. This reaction is also known as a hydrolysis reaction, instead of a transfer reaction. An example of a hexosyltransferase which may be used in the invention is a β-glucanosyltransferase. Such an enzyme may be able to catalyze degradation of (1,3)(1,4) glucan and/or cellulose and/or a cellulose degradation product.

"Glucuronidase" includes enzymes that catalyze the hydrolysis of a glucoronoside, for example β-glucuronoside to yield an alcohol. Many glucuronidases have been characterized and may be suitable for use in the invention, for example β-glucuronidase (EC 3.2.1.31), hyaluronoglucuronidase (EC 3.2.1.36), glucuronosyl-disulfoglucosamine glucuronidase (3.2.1.56), glycyrrhizinate β-glucuronidase (3.2.1.128) or α-D-glucuronidase (EC 3.2.1.139).

A composition of the invention may comprise an expansin or expansin-like polypeptide, such as a swollenin (see Saloheimo et al., Eur. J. Biohem. 269, 4202-4211, 2002) or a swollenin-like polypeptide.

Expansins are implicated in loosening of the cell wall structure during plant cell growth. Expansins have been proposed to disrupt hydrogen bonding between cellulose and other cell wall polysaccharides without having hydrolytic activity. In this way, they are thought to allow the sliding of cellulose fibers and enlargement of the cell wall. Swollenin, an expansin-like polypeptide contains an N-terminal Carbohydrate Binding Module Family 1 domain (CBD) and a C-terminal expansin-like domain. For the purposes of this invention, an expansin-like polypeptide or swollenin-like polypeptide may comprise one or both of such domains and/or may disrupt the structure of cell walls (such as disrupting cellulose structure), optionally without producing detectable amounts of reducing sugars.

Alternative polypeptides that may be present are for instance chosen from the group of catalase, laccase, phenoloxidase, oxidase, oxidoreductases, cellulase, xylanase, peroxidase, lipase, hydrolase, esterase, cutinase, protease and other proteolytic polypeptides, aminopeptidase, carboxypeptidase, phytase, lyase, pectinase and other pectinolytic enzymes, amylase, glucoamylase, alpha-galactosidase, beta-galactosidase, alpha-glucosidase, beta-glucosidase, mannosidase, isomerase, invertase, transferase, ribonuclease, chitinase, mutanase and deoxyribonuclease.

The invention further relates to compositions comprising one or more of the polypeptides according to the invention.

In one embodiment, the polypeptide of the invention is a hemicellulase, and the composition of the invention will typically comprise a cellulase and/or a pectinase in addition to the polypeptide of the invention.

In a further embodiment, the polypeptide of the invention is a pectinase, and the composition of the invention will typically comprise a cellulase and/or a hemicellulase in addition to the polypeptide of the invention.

In a further embodiment, the polypeptide of the invention is a cellulase, and the composition of the invention will typically comprise a hemicellulase and/or a pectinase in addition to the polypeptide of the invention.

In an embodiment, the cellulase is one or more of CBH I, CBH II, EG or BG. The polypeptide may be a single cellulase and/or a hemicellulase or a pectinase or a mixture of cellulase and/or a hemicellulase and/or a pectinase and or other polypeptides. In an embodiment, the polypeptide is a cellulase which is a mixture of two polypeptides selected from CBH I, CBH II, EG or BG.

Preferably the cellulase is a mixture comprising CBH I, CBH II, EG and BG. A composition of the invention may comprise one, two or three classes of cellulase, for example one, two or all of an endo-1,4-β-glucanase (EG), an exocellobiohydrolase (CBH) and a β-glucosidase (BG).

A composition of the invention may comprise a polypeptide which has the same enzymatic activity, for example the same type of cellulase, hemicellulase and/or pectinase activity as that provided by a polypeptide of the invention.

A composition of the invention may comprise a polypeptide which has a different type of cellulase activity and/or hemicellulase activity and/or pectinase activity than that provided by a polypeptide of the invention. For example, a composition of the invention may comprise one type of cellulase and/or hemicellulase activity and/or pectinase activity provided by a polypeptide of the invention and a second type of cellulase and/or hemicellulase activity and/or pectinase activity provided by an additional hemicellulase/pectinase.

A composition of the invention may comprise the polypeptide product of a cellulose integrating polypeptide, scaffoldin or a scaffoldin-like polypeptide, for example CipA or CipC from *Clostridium thermocellum* or *Clostridium cellulolyticum* respectively.

Scaffoldins and cellulose integrating polypeptides are multi-functional integrating subunits which may organize cellulolytic subunits into a multi-enzyme complex. This is accomplished by the interaction of two complementary classes of domain, i.e. a cohesion domain on scaffoldin and a dockerin domain on each enzymatic unit. The scaffoldin subunit also bears a cellulose-binding module (CBM) that mediates attachment of the cellulosome to its substrate. A scaffoldin or cellulose integrating polypeptide for the purposes of this invention may comprise one or both of such domains.

In one embodiment the polypeptide composition may comprise polypeptides that originate from other microorganisms than *Talaromyces*, e.g. *Trichoderma* CBHI, *Trichoderma* CBHII, *Trichoderma* BG and/or *Trichoderma* EG, beta-D-glucoside glucohydrolase, endo-galactanase, Swollenin, Cip1, Cip2, Xylanase III, beta-xylosidase XylA, acetylxylan esterase, chitinase, beta-mannase.

A composition of the invention may comprise a cellulose induced polypeptide or modulating polypeptide, for example as encoded by cip1 or cip2 gene or similar genes from *Trichoderma reesei/Hypocrea jacorina* (see Foreman et al., J. Biol. Chem. 278(34), 31988-31997, 2003). The polypeptide product of these genes are bimodular polypeptides, which contain a cellulose binding module and a domain which function or activity can not be related to known glycosyl hydrolase families. Yet, the presence of a cellulose binding module and the coregulation of the expression of these genes with cellulases components indicates previously unrecognised activities with potential role in biomass degradation.

A composition of the invention may be composed of a member of each of the classes of the polypeptides mentioned above, several members of one polypeptide class, or any combination of these polypeptide classes.

A composition of the invention may be composed of polypeptides, for example enzymes, from (1) commercial suppliers; (2) cloned genes expressing polypeptides, for example enzymes; (3) complex broth (such as that resulting from growth of a microbial strain in media, wherein the strains secrete polypeptides and enzymes into the media; (4) cell lysates of strains grown as in (3); and/or (5) plant material expressing polypeptides, for example enzymes. Different polypeptides, for example enzymes in a composition of the invention may be obtained from different sources.

Use of the Polypeptides

The polypeptides and polypeptide compositions according to the invention may be used in many different applications For instance they may be used to produce fermentable sugars. In one embodiment they can be used in a process for saccharification of lignocellulosic material, wherein lignocellulosic material that has been optionally pretreated, is contacted with a *Talaromyces* transformant according to the invention or a cellulase, hemicellulase or pectinase according to the invention, wherein one or more sugars are produced. The fermentable sugars can then, as part of a biofuel process, be converted into biogas or ethanol, butanol, isobutanol, 2 butanol or other suitable substances. The invention thus relates to a process for the preparation of a fermentation product, for instance ethanol, wherein sugars are fermented with a fermenting microorganism, preferably yeast, to produce the fermentation product.

Alternatively the polypeptides and their compositions may be used as enzyme, for instance in production of food products, in detergent compositions, in the paper and pulp industry and in antibacterial formulations, in pharmaceutical products such as throat lozenges, toothpastes, and mouthwash. Some of the uses will be illustrated in more detail below.

In the uses and methods described below, the components of the compositions described above may be provided concomitantly (i.e. as a single composition per se) or separately or sequentially.

The invention also relates to the use of the polypeptide according to the invention and compositions comprising such an enzyme in industrial processes.

Despite the long term experience obtained with these processes, the polypeptide according to the invention may feature a number of significant advantages over enzymes currently used. Depending on the specific application, these advantages may include aspects such as lower production costs, higher specificity towards the substrate, reduced antigenicity, fewer undesirable side activities, higher yields when produced in a suitable microorganism, more suitable pH and temperature ranges, non-inhibition by hydrophobic, lignin-derived products or less product inhibition or, in the case of the food industry a better taste or texture of a final product as well as food grade and kosher aspects.

In principle, a polypeptide or composition of the invention may be used in any process which requires the treatment of a material which comprises polysaccharide. Thus, a polypeptide or composition of the invention may be used in the treatment of polysaccharide material. Herein, polysaccharide material is a material which comprises or consists essential of one or, more typically, more than one polysaccharide.

Typically, plants and material derived therefrom comprise significant quantities of non-starch polysaccharide material. Accordingly, a polypeptide of the invention may be used in the treatment of a plant or fungal material or a material derived therefrom.

Lignocellulose

The polypeptides may advantageously be used to degrade lignocellulosic material. The major polysaccharides are cellulose (glucans), hemicelluloses (xylans, heteroxylans and xyloglucans). In addition, some hemicellulose may be present as glucomannans, for example in wood-derived feedstocks. The enzymatic hydrolysis of these polysaccharides to soluble sugars, for example glucose, xylose, arabinose, galactose, fructose, mannose, rhamnose, ribose, D-galacturonic acid and other hexoses and pentoses occurs under the action of different enzymes acting in concert.

In addition, pectins and other pectic substances such as arabinans may make up considerably proportion of the dry mass of typically cell walls from non-woody plant tissues (about a quarter to half of dry mass may be pectins).

Cellulose is a linear polysaccharide composed of glucose residues linked by β-1,4 bonds. The linear nature of the cellulose fibers, as well as the stoichiometry of the β-linked glucose (relative to α) generates structures more prone to interstrand hydrogen bonding than the highly branched α-linked structures of starch. Thus, cellulose polymers are generally less soluble, and form more tightly bound fibers than the fibers found in starch.

Hemicellulose is a complex polymer, and its composition often varies widely from organism to organism, and from one tissue type to another. In general, a main component of hemicellulose is β-1,4-linked xylose, a five carbon sugar. However, this xylose is often branched at O-3 and/or O-2 and can be substituted with linkages to arabinose, galactose, mannose, glucuronic acid, galacturonic acid or by esterification to acetic acid (and esterification of ferulic acid to arabinose). Hemicellulose can also contain glucan, which is a general term for β-linked six carbon sugars (such as the β-(1,3)(1,4) glucans and heteroglucans mentioned previously) and additionally glucomannans (in which both glucose and mannose are present in the linear backbone, linked to each other by β-linkages).

Pectic substances include pectins, arabinans, galactans and arabinogalactans. Pectins are the most complex polysaccharides in the plant cell wall. They are built up around a core chain of α(1,4)-linked D-galacturonic acid units interspersed to some degree with L-rhamnose. In any one cell wall there are a number of structural units that fit this description and it has generally been considered that in a single pectic molecule, the core chains of different structural units are continuous with one another.

The principal types of structural unit are: galacturonan (homogalacturonan), which may be substituted with methanol on the carboxyl group and acetate on O-2 and O-3; rhamnogalacturonan I (RGI), in which galacturonic acid units alternate with rhamnose units carrying (1,4)-linked galactan and (1,5)-linked arabinan side-chains. The arabinan side-chains may be attached directly to rhamnose or indirectly through the galactan chains; xylogalacturonan, with single xylosyl units on O-3 of galacturonic acid (closely associated with RGI); and rhamnogalacturonan II (RGII), a particularly complex minor unit containing unusual sugars, for example apiose. An RGII unit may contain two apiosyl residues which, under suitable ionic conditions, can reversibly form esters with borate.

The composition, nature of substitution, and degree of branching of hemicellulose is very different in dicotyledonous plants (dicots, i.e., plant whose seeds have two cotyledons or seed leaves such as lima beans, peanuts, almonds, peas, kidney beans) as compared to monocotyledonous plants (monocots; i.e., plants having a single cotyledon or seed leaf such as corn, wheat, rice, grasses, barley). In dicots, hemicellulose is comprised mainly of xyloglucans that are 1,4-β-linked glucose chains with 1,6-β-linked xylosyl side chains. In monocots, including most grain crops, the principal components of hemicellulose are heteroxylans. These are primarily comprised of 1,4-β-linked xylose backbone polymers with 1,3-α linkages to arabinose, galactose, mannose and glucuronic acid or 4-O-methyl-glucuronic acid as well as xylose modified by ester-linked acetic acids. Also present are β glucans comprised of 1,3- and 1,4-β-linked glucosyl chains. In monocots, cellulose, heteroxylans and β-glucans may be present in roughly equal amounts, each comprising about 15-25% of the dry matter of cell walls. Also, different plants may comprise different amounts of, and different compositions of, pectic substances. For example, sugar beet contains about 19% pectin and about 21% arabinan on a dry weight basis.

Accordingly, a composition of the invention may be tailored in view of the particular feedstock (also called substrate) which is to be used. That is to say, the spectrum of activities in a composition of the invention may vary depending on the feedstock in question.

Enzyme combinations or physical treatments can be administered concomitantly or sequentially. The enzymes can be produced either exogenously in microorganisms, yeasts, fungi, bacteria or plants, then isolated and added to the lignocellulosic feedstock. Alternatively, the enzymes are produced, but not isolated, and crude cell mass fermentation broth, or plant material (such as corn stover), and the like are added to the feedstock. Alternatively, the crude cell mass or enzyme production medium or plant material may be treated to prevent further microbial growth (for example, by heating or addition of antimicrobial agents), then added to the feedstock. These crude enzyme mixtures may include the organism producing the enzyme. Alternatively, the enzyme may be produced in a fermentation that uses feedstock (such as corn stover) to provide nutrition to an organism that produces an enzyme(s). In this manner, plants that produce the enzymes may serve as the lignocellulosic feedstock and be added into lignocellulosic feedstock. The carbohydrate polymers (cellulose and hemicelluloses) are tightly bound to the lignin by hydrogen and covalent bonds. Accordingly, a polypeptide of the invention may be used in the treatment of lignocellulolytic material. Herein, lignocellulolytic material is a material which comprises or consists essential of lignocellulose. Thus, in a method of the invention for the treatment of a non-starch polysaccharide, the non-starch polysaccharide may be a lignocellulosic material/biomass.

Accordingly, the invention provides a method of treating a substrate comprising non-starch polysaccharide in which the treatment comprises the degradation and/or hydrolysis and/or modification of cellulose and/or hemicellulose and/or a pectic substance.

Endo-1,4-β-glucanases (EG) and exo-cellobiohydrolases (CBH) catalyze the hydrolysis of insoluble cellulose to cellooligosaccharides (cellobiose as a main product), while β-glucosidases (BG) convert the oligosaccharides, mainly cellobiose and cellotriose to glucose.

Xylanases together with other accessory enzymes, for example α-L-arabinofuranosidases, feruloyl and acetylxylan esterases, glucuronidases, and β-xylosidases, catalyze the hydrolysis of hemicelluloses.

Pectinases, for example an endo polygalacturonase, a pectin methyl esterase, an endo-galactanase, a beta galactosidase, a pectin acetyl esterase, an endo-pectin lyase, pectate lyase, alpha rhamnosidase, an exo-galacturonase, an expolygalacturonate lyase, a rhamnogalacturonan hydrolase, a rhamnogalacturonan lyase, a rhamnogalacturonan acetyl esterase, a rhamnogalacturonan galacturonohydrolase, a xylogalacturonase, an α-arabinofuranosidase Degradation in this context indicates that the treatment results in the generation of hydrolysis products of cellulose and/or hemicellulose and/or a pectic substance, i.e. saccharides of shorter length are present as result of the treatment than are present in a similar untreated non-starch polysaccharide. Thus, degradation in this context may result in the liberation of oligosaccharides and/or sugar monomers.

All plants contain non-starch polysaccharide as do virtually all plant-derived polysaccharide materials. Accordingly, in a method of the invention for the treatment of substrate comprising a non-starch polysaccharide, said substrate may be provided in the form of a plant or a plant derived material or a material comprising a plant or plant derived material, for example a plant pulp, a plant extract, a foodstuff or ingredient therefore, a fabric, a textile or an item of clothing.

Lignocellulolytic biomass suitable for use in the invention includes biomass and can include virgin biomass and/or non-virgin biomass such as agricultural biomass, commercial organics, construction and demolition debris, municipal solid waste, waste paper and yard waste. Common forms of biomass include trees, shrubs and grasses, wheat, wheat straw, sugar cane bagasse, corn, corn husks, corn cobs, corn kernel including fiber from kernels, products and by-products from milling of grains such as corn, wheat and barley (including wet milling and dry milling) often called "bran or fibre" as well as municipal solid waste, waste paper and yard waste. The biomass can also be, but is not limited to, herbaceous material, agricultural residues, forestry residues, municipal solid wastes, waste paper, and pulp and paper mill residues. "Agricultural biomass" includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, fruit peels, vines, sugar beet pulp, wheat midlings, oat hulls, and hard and soft woods (not including woods with deleterious materials). In addition, agricultural biomass includes organic waste materials generated from agricultural processes including farming and forestry activities, specifically including forestry wood waste. Agricultural biomass may be any of the aforestated singularly or in any combination or mixture thereof. Further examples of suitable biomass are orchard primings, chaparral, mill waste, urban wood waste, municipal waste, logging waste, forest thinnings, short-rotation woody crops, industrial waste, wheat straw, oat straw, rice straw, barley straw, rye straw, flax straw, soy hulls, rice hulls, rice straw, corn gluten feed, oat hulls, sugar cane, corn stover, corn stalks, corn cobs, corn husks, prairie grass, gamagrass, foxtail; sugar beet pulp, citrus fruit pulp, seed hulls, cellulosic animal wastes, lawn clippings, cotton, seaweed, trees, shrubs, grasses, wheat, wheat straw, sugar cane bagasse, corn, corn husks, corn hobs, corn kernel, fiber from kernels, products and by-products from wet or dry milling of grains, municipal solid waste, waste paper, yard waste, herbaceous material, agricultural residues, forestry residues, municipal solid waste, waste paper, pulp, paper mill residues, branches, bushes, canes, corn, corn husks, an energy crop, forest, a fruit, a flower, a grain, a grass, a herbaceous crop, a leaf, bark, a needle, a log, a root, a sapling, a shrub, switch grass, a tree, a vegetable, fruit peel, a vine, sugar beet pulp, wheat midlings, oat hulls, hard or soft wood, organic waste material generated from an agricultural process, forestry wood waste, or a combination of any two or more thereof.

Apart from virgin biomass or feedstocks already processed in food and feed or paper and pulping industries, the biomass/feedstock may additionally be pretreated with heat, mechanical and/or chemical modification or any combination of such methods in order to enhance enzymatic degradation.

Pretreatment

Before enzymatic treatment, the lignocellulosic material may be pretreated. The pretreatment may comprise exposing the lignocellulosic material to an acid, a base, an ionic liquid, a solvent, heat, a peroxide, ozone, mechanical shredding, grinding, milling or rapid depressurization, or a combination of any two or more thereof. This chemical pretreatment is often combined with heat-pretreatment, e.g. between 150-220 C for 1 to 30 minutes.

After the pretreatment step, a liquefaction/hydrolysis or presaccharification step involving incubation with an enzyme or enzyme mixture can be utilized. The pretreatment step can be performed at many different temperatures. In an embodiment, the pretreatment occur at the temperature best suited to the enzyme mix being tested, or the predicted enzyme optimum of the enzymes to be tested. The temperature of the pretreatment may range from about 10° C. to about 95° C., about 20° C. to about 85° C., about 30° C. to about 70° C., about 40° C. to about 60° C., about 37° C. to about 50° C., preferably about 37° C. to about 80° C., more preferably about 60-70° C. even more preferably around 65° C. The pH of the pretreatment mixture may range from about 2.0 to about 10.0, but is preferably about 3.0 to about 7.0, more preferably about 4.0 to about 6.0, even more preferably about 4.0 to about 5.0. Again, the pH may be adjusted to maximize enzyme activity and may be adjusted with the addition of the enzyme. Comparison of the results of the assay results from this test will allow one to modify the method to best suit the enzymes being tested.

The liquefaction/hydrolysis or presaccharification step reaction may occur from several minutes to several hours, such as from about 1 hour to about 120 hours, preferably from about 2 hours to about 48 hours, more preferably from about 2 to about 24 hours, most preferably for from about 2 to about 6 hours. The cellulase treatment may occur from several minutes to several hours, such as from about 6 hours to about 120 hours, preferably about 12 hours to about 72 hours, more preferably about 24 to 48 hours.

Saccharification

The invention provides a method for producing a sugar from a lignocellulosic material which method comprises contacting a polypeptide of the invention to a composition of the invention with the lignocellulosic material.

Such a method allows free sugars (monomers) and/or oligosaccharides to be generated from lignocellulosic biomass. These methods involve converting lignocellulosic biomass to free sugars and small oligosaccharides with a polypeptide or composition of the invention.

The process of converting a complex carbohydrate such as lignocellulose into sugars preferably allows conversion into fermentable sugars. Such a process may be referred to as "saccharification." Accordingly, a method of the invention may result in the liberation of one or more hexose and/or pentose sugars, such as one or more of glucose, xylose, arabinose, galactose, galacturonic acid, glucuronic acid, mannose, rhamnose, ribose and fructose.

Accordingly, a further aspect of the invention includes methods that utilize the polypeptide of composition of the invention described above together with further enzymes or physical treatments such as temperature and pH to convert the lignocellulosic plant biomass to sugars and oligosaccharides.

While the composition has been discussed as a single mixture it is recognized that the enzymes may be added sequentially where the temperature, pH, and other conditions may be altered to increase the activity of each individual enzyme. Alternatively, an optimum pH and temperature can be determined for the enzyme mixture.

The enzymes are reacted with substrate under any appropriate conditions. For example, enzymes can be incubated at about 25° C., about 30° C., about 35° C., about 37° C., about 40° C., about 45° C., about 50° C., about 55° C., about 60° C., about 65° C., about 70° C., about 75° C., about 80° C., about 85° C., about 90° C. or higher. That is, they can be incubated at a temperature of from about 20° C. to about 95° C., for example in buffers of low to medium ionic strength and/or from low to neutral pH. By "medium ionic strength" is intended that the buffer has an ion concentration of about 200 millimole (mM) or less for any single ion component. The pH may range from about pH 2.5, about pH 3.0, about pH 3.5, about pH 4.0, about pH 4.5, about pH 5, about pH 5.5, about pH 6, about pH 6.5, about pH 7, about pH 7.5, about pH 8.0, to about pH 8.5. Generally, the pH range will be from about pH 3.0 to about pH 7. For the production of ethanol an acidic medium may be used, e.g. pH=4, whereas for the production of biogas neutral pH, e.g. pH=7 may be used. Incubation of enzyme combinations under these conditions results in release or liberation of substantial amounts of the sugar from the lignocellulose. By substantial amount is intended at least 20%, 30%, 40%, 50%, 60%, 70%, 80%, 90%, 95% or more of available sugar.

The polypeptides, such as enzymes, can be produced either exogenously in microorganisms, yeasts, fungi, bacteria or plants, then isolated and added, for example, to lignocellulosic feedstock. Alternatively, the enzymes are produced, but not isolated, and crude cell mass fermentation broth, or plant material (such as corn stover), and the like may be added to, for example, the feedstock. Alternatively, the crude cell mass or enzyme production medium or plant material may be treated to prevent further microbial growth (for example, by heating or addition of antimicrobial agents), then added to, for example, a feedstock. These crude enzyme mixtures may include the organism producing the enzyme. Alternatively, the enzyme may be produced in a fermentation that uses feedstock (such as corn stover) to provide nutrition to an organism that produces an enzyme(s). In this manner, plants that produce the enzymes may themselves serve as a lignocellulosic feedstock and be added into lignocellulosic feedstock.

Fermentation of Sugars

The fermentable sugars can be converted to useful value-added fermentation products, non-limiting examples of which include amino acids, vitamins, pharmaceuticals, animal feed supplements, specialty chemicals, chemical feedstocks, plastics, solvents, fuels, or other organic polymers, lactic acid, and ethanol, including fuel ethanol. In particular the sugars may be used as feedstocks for fermentation into chemicals, plastics, such as for instance succinic acid and (bio) fuels, including ethanol, methanol, butanol synthetic liquid fuels and biogas.

For instance, in the method of the invention, an enzyme or combination of enzymes acts on a lignocellulosic substrate or plant biomass, serving as the feedstock, so as to convert this complex substrate to simple sugars and oligosaccharides for the production of ethanol or other useful fermentation products.

Sugars released from biomass can be converted to useful fermentation products such a one of those including, but not limited to, amino acids, vitamins, pharmaceuticals, animal feed supplements, specialty chemicals, chemical feedstocks, plastics, and ethanol, including fuel ethanol.

Accordingly, the invention provides a method for the preparation of a fermentation product, which method comprises:

a. degrading lignocellulose using a method as described herein; and b. fermentation of the resulting material, thereby to prepare a fermentation product.

The fermentation may be carried out under aerobic or anaerobic conditions. Preferably, the process is carried out under micro-aerophilic or oxygen limited conditions.

An anaerobic fermentation process is herein defined as a fermentation process run in the absence of oxygen or in which substantially no oxygen is consumed, preferably about 5 or less, about 2.5 or less or about 1 mmol/L/h or less, and wherein organic molecules serve as both electron donor and electron acceptors.

An oxygen-limited fermentation process is a process in which the oxygen consumption is limited by the oxygen transfer from the gas to the liquid. The degree of oxygen limitation is determined by the amount and composition of the ingoing gasflow as well as the actual mixing/mass transfer properties of the fermentation equipment used. Preferably, in a process under oxygen-limited conditions, the rate of oxygen consumption is at least about 5.5, more preferably at least about 6 and even more preferably at least about 7 mmol/L/h.

A method for the preparation of a fermentation product may optionally comprise recovery of the fermentation product.

SSF

Fermentation and Saccharification may also be executed in Simultaneous Saccharification and Fermentation (SSF) mode. One of the advantages of this mode is reduction of the sugar inhibition on enzymatic hydrolysis (Sugar inhibition on cellulases is described by Caminal B&B Vol XXVII Pp 1282-1290).

Fermentation Products

Fermentation products which may be produced according to the invention include amino acids, vitamins, pharmaceuticals, animal feed supplements, specialty chemicals, chemical feedstocks, plastics, solvents, fuels, or other organic polymers, lactic acid, and ethanol, including fuel ethanol (the term "ethanol" being understood to include ethyl alcohol or mixtures of ethyl alcohol and water).

Specific value-added products that may be produced by the methods of the invention include, but not limited to, biofuels (including ethanol and butanol and a biogas); lactic acid; a plastic; a specialty chemical; an organic acid, including citric acid, succinic acid, fumaric acid, itaconic acid and maleic acid; 3-hydroxy-propionic acid, acrylic acid; acetic acid; 1,3-propane-diol; ethylene, glycerol; a solvent; an animal feed supplement; a pharmaceutical, such as a β-lactam antibiotic or a cephalosporin; vitamins; an amino acid, such as lysine, methionine, tryptophan, threonine, and aspartic acid; an industrial enzyme, such as a protease, a cellulase, an amylase, a glucanase, a lactase, a lipase, a lyase, an oxidoreductases, a transferase or a xylanase; and a chemical feedstock.

Biogas

The invention also provides use of a polypeptide or composition a described herein in a method for the preparation of biogas. Biogas typically refers to a gas produced by the biological breakdown of organic matter, for example non-starch carbohydrate containing material, in the absence of oxygen. Biogas originates from biogenic material and is a type of biofuel. One type of biogas is produced by anaerobic digestion or fermentation of biodegradable materials such as biomass, manure, silage or sewage, municipal waste, and energy crops. This type of biogas is comprised primarily of methane and carbon dioxide. The gas methane, can be combusted or oxidized with oxygen. Air contains 21% oxygen. This energy release allows biogas to be used as a fuel. Biogas can be used as a low-cost fuel in any country for any heating purpose, such as cooking. It can also be utilized in modern waste management facilities where it can be used to run any type of heat engine, to generate either mechanical or electrical power.

The first step in microbial biogas production consists in the enzymatic degradation of polymers and complex substrates (for example non-starch carbohydrate). Accordingly, the invention provides a method for preparation of a biogas in which a substrate comprising non-starch carbohydrate is contacted with a polypeptide or composition of the invention, thereby to yield fermentable material which may be converted into a biogas by an organism such as a microorganism. In such a method, a polypeptide of the invention may be provided by way of an organism, for example a microorganism which expresses such a polypeptide.

Use of Enzymes in Food Products

The polypeptides and compositions of the invention may be used in a method of processing plant material to degrade or modify the cellulose or hemicellulose or pectic substance constituents of the cell walls of the plant or fungal material. Such methods may be useful in the preparation of food product. Accordingly, the invention provides a method for preparing a food product which method comprises incorporating a polypeptide or composition of the invention during preparation of the food product.

The invention also provides a method of processing a plant material which method comprises contacting the plant material with a polypeptide or composition of the invention to degrade or modify the cellulose in the (plant) material. Preferably the plant material is a plant pulp or plant extract, such as juices.

The present invention also provides a method for reducing the viscosity, clarity and/or filterability of a plant extract which method comprises contacting the plant extract with a polypeptide or composition of the invention in an amount effective in degrading cellulose or hemicellulose or pectic substances contained in the plant extract.

Plant and cellulose/hemicellulose/pectic substance-containing materials include plant pulp, parts of plants and plant extracts. In the context of this invention an extract from a plant material is any substance which can be derived from plant material by extraction (mechanical and/or chemical), processing or by other separation techniques. The extract may be juice, nectar, base, or concentrates made thereof. The plant material may comprise or be derived from vegetables, e. g., carrots, celery, onions, legumes or leguminous plants (soy, soybean, peas) or fruit, e. g., pome or seed fruit (apples, pears, quince etc.), grapes, tomatoes, citrus (orange, lemon, lime, mandarin), melons, prunes, cherries, black currants, redcurrants, raspberries, strawberries, cranberries, pineapple and other tropical fruits, trees and parts thereof (e. g. pollen, from pine trees), or cereal (oats, barley, wheat, maize, rice). The material (to be hydrolysed) may also be agricultural residues, such as sugar beet pulp, corn cobs, wheat straw, (ground) nutshells, or recyclable materials, e. g. (waste) paper.

The polypeptides of the invention can thus be used to treat plant material including plant pulp and plant extracts. They may also be used to treat liquid or solid foodstuffs or edible foodstuff ingredients, or be used in the extraction of coffee, plant oils, starch or as a thickener in foods.

Typically, the polypeptides of the invention are used as a composition/enzyme preparation as described above. The composition will generally be added to plant pulp obtainable by, for example mechanical processing such as crushing or milling plant material. Incubation of the composition with the plant will typically be carried out for at time of from 10 minutes to 5 hours, such as 30 minutes to 2 hours, preferably for about 1 hour. The processing temperature is preferably from about 10° C. to about 55° C., e. g. from about 15° C. to about 25° C., optimally about 20° C. and one can use from about 10 g to about 300 g, preferably from about 30 g to about 70 g, optimally about 50 g of enzyme per ton of material to be treated.

All of the enzyme(s) or their compositions used may be added sequentially or at the same time to the plant pulp. Depending on the composition of the enzyme preparation the plant material may first be macerated (e. g. to a pure) or liquefied. Using the polypeptides of the invention processing parameters such as the yield of the extraction, viscosity of the extract and/or quality of the extract can be improved.

Alternatively, or in addition to the above, a polypeptide of the invention may be added to the raw juice obtained from pressing or liquefying the plant pulp. Treatment of the raw juice will be carried out in a similar manner to the plant pulp in respect of dosage, temperature and holding time. Again, other enzymes such as those discussed previously may be included. Typical incubation conditions are as described in the previous paragraph.

Once the raw juice has been incubated with the polypeptides of the invention, the juice is then centrifuged or (ultra) filtered to produce the final product.

After treatment with the polypeptide of the invention the (end) product can be heat treated, e. g. at about 100° C. for a time of from about 1 minute to about 1 hour, under conditions to partially or fully inactivate the polypeptide(s) of the invention.

A composition containing a polypeptide of the invention may also be used during the preparation of fruit or vegetable purees.

The polypeptide of the invention may also be used in brewing, wine making, distilling or baking. It may therefore used in the preparation of alcoholic beverages such as wine and beer. For example it may improve the filterability or clarity, for example of beers, wort (e.g. containing barley and/or sorghum malt) or wine.

Furthermore, a polypeptide or composition of the invention may be used for treatment of brewers spent grain, i.e. residuals from beer wort production containing barley or malted barley or other cereals, so as to improve the utilization of the residuals for, e.g., animal feed.

The polypeptide may assist in the removal of dissolved organic substances from broth or culture media, for example where distillery waste from organic origin is bioconverted into microbial biomass. The polypeptide of the invention may improve filterability and/or reduce viscosity in glucose syrups, such as from cereals produced by liquefaction (e.g. with α-amylase).

In baking the polypeptide may improve the dough structure, modify its stickiness or suppleness, improve the loaf volume and/or crumb structure or impart better textural characteristics such as break, shred or crumb quality.

The present invention thus relates to methods for preparing a dough or a cereal-based food product comprising incorporating into the dough a polypeptide or composition of the present invention. This may improve one or more properties of the dough or the cereal-based food product obtained from the dough relative to a dough or a cereal-based food product in which the polypeptide is not incorporated.

The preparation of the cereal-based food product according to the invention further can comprise steps known in the art such as boiling, drying, frying, steaming or baking of the obtained dough.

Products that are made from a dough that is boiled are for example boiled noodles, dumplings, products that are made from fried dough are for example doughnuts, beignets, fried noodles, products that are made for steamed dough are for example steamed buns and steamed noodles, examples of products made from dried dough are pasta and dried noodles and examples of products made from baked dough are bread, cookies, cake.

The term "improved property" is defined herein as any property of a dough and/or a product obtained from the dough, particularly a cereal-based food product, which is improved by the action of the polypeptide according to the invention relative to a dough or product in which the polypeptide according to the invention is not incorporated. The improved property may include, but is not limited to, increased strength of the dough, increased elasticity of the dough, increased stability of the dough, improved machineability of the dough, improved proofing resistance of the dough, reduced stickiness of the dough, improved extensibility of the dough, increased volume of the cereal-based food product, reduced blistering of the cereal-based food product, improved crumb structure of the baked product, improved softness of the cereal-based food product, improved flavour of the cereal-based food product, improved anti-staling of the cereal-based food product. Improved properties related to pasta and noodle type of cereal-based products are for example improved firmness, reduced stickiness, improved cohesiveness and reduced cooking loss.

The improved property may be determined by comparison of a dough and/or a cereal-based food product prepared with and without addition of a polypeptide of the present invention. Organoleptic qualities may be evaluated using procedures well established in the baking industry, and may include, for example, the use of a panel of trained taste-testers.

The term "dough" is defined herein as a mixture of cereal flour and other ingredients firm enough to knead or roll. Examples of cereals are wheat, rye, corn, maize, barley, rice, groats, buckwheat and oat. Wheat is I here and hereafter intended to encompass all known species of *Triticum* genus, for example aestivum, durum and/or spelta. Examples of suitable other ingredients are: the polypeptide according to the present invention, additional enzymes, chemical additives and/or processing aids. The dough may be fresh, frozen, pre-pared, or pre-baked. The preparation of a dough from the ingredients described above is well known in the art and comprises mixing of said ingredients and processing aids and one or more moulding and optionally fermentation steps. The preparation of frozen dough is described by Kulp and Lorenz in Frozen and Refrigerated Doughs and Batters.

The term "cereal-based food product" is defined herein as any product prepared from a dough, either of a soft or a crisp character. Examples of cereal-based food products, whether of a white, light or dark type, which may be advantageously produced by the present invention are bread (in particular white, whole-meal or rye bread), typically in the form of loaves or rolls, French baguette-type bread, pasta, noodles, doughnuts, bagels, cake, pita bread, tortillas, tacos, cakes, pancakes, biscuits, cookies, pie crusts, steamed bread, and crisp bread, and the like.

The term "baked product" is defined herein as any cereal-based food product prepared by baking the dough.

Non-starch polysaccharides (NSP) can increase the viscosity of the digesta which can, in turn, decrease nutrient availability and animal performance. The use of the polypeptide of the present invention can improve phosphorus utilization as well as cation minerals and polypeptide during animal digesta.

Adding specific nutrients to feed improves animal digestion and thereby reduces feed costs. A lot of feed additives are being currently used and new concepts are continuously developed. Use of specific enzymes like non-starch carbohydrate degrading enzymes could breakdown the fibre releasing energy as well as increasing the polypeptide digestibility due to better accessibility of the polypeptide when the fibre gets broken down. In this way the feed cost could come down as well as the polypeptide levels in the feed also could be reduced.

Non-starch polysaccharides (NSPs) are also present in virtually all feed ingredients of plant origin. NSPs are poorly utilized and can, when solubilized, exert adverse effects on digestion. Exogenous enzymes can contribute to a better utilization of these NSPs and as a consequence reduce any anti-nutritional effects. Non-starch carbohydrate degrading enzymes of the present invention can be used for this purpose in cereal-based diets for poultry and, to a lesser extent, for pigs and other species.

A non-starch carbohydrate degrading polypeptide/enzyme of the invention (of a composition comprising the polypeptide/enzyme of the invention) may be used in the detergent industry, for example for removal from laundry of carbohydrate-based stains. A detergent composition may comprise a polypeptide/enzyme of the invention and, in addition, one or more of a cellulase, a hemicellulase, a pectinase, a protease, a lipase, a cutinase, an amylase or a carbohydrase.

Use of Enzymes in Detergent Compositions

A detergent composition comprising a polypeptide or composition of the invention may be in any convenient form, for example a paste, a gel, a powder or a liquid. A liquid detergent may be aqueous, typically containing up to about 70% water and from about 0 to about 30% organic solvent or non-aqueous material.

Such a detergent composition may, for example, be formulated as a hand or machine laundry detergent composition including a laundry additive composition suitable for pretreatment of stained fabrics and a rinse added fabric softener composition, or be formulated as a detergent composition for use in general household hard surface cleaning operations, or be formulated for hand or machine dish washing operations. In general, the properties of the enzyme should be compatible with the aselected detergent (for example, pH-optimum, compatibility with other enzymatic and/or non-enzymatic ingredients, etc.) and the enzyme(s) should be present in an effective amount. A detergent composition may comprise a surfactant, for example an anionic or non-ionic surfactant, a detergent builder or complexing agent, one or more polymers, a bleaching system (for example an $H_2O_2$ source) or an enzyme stabilizer. A detergent composition may also comprise any other conventional detergent ingredient such as, for example, a conditioner including a clay, a foam booster, a sud suppressor, an anti-corrosion agent, a soil-suspending agent, an an-soil redeposition agent, a dye, a bactericide, an optical brightener, a hydrotropes, a tarnish inhibitor or a perfume.

Use of Enzymes in Paper and Pulp Processing

A polypeptide or composition of the present invention may be used in the paper and pulp industry, inter alia in the bleaching process to enhance the brightness of bleached pulps whereby the amount of chlorine used in the bleaching stages may be reduced, and to increase the freeness of pulps in the recycled paper process (Eriksson, K. E. L., Wood Science and Technology 24 (1990):79-101; Paice, et al., Biotechnol. and Bioeng. 32 (1988):235-239 and Pommier et al., Tappi Journal (1989):187-191). Furthermore, a polypeptide or composition of the invention may be used for treatment of lignocellulosic pulp so as to improve the bleachability thereof. Thereby the amount of chlorine need to obtain a satisfactory bleaching of the pulp may be reduced.

A polypeptide or composition of the invention may be used in a method of reducing the rate at which cellulose-containing fabrics become harsh or of reducing the harshness of cellulose-containing fabrics, the method comprising treating cellulose-containing fabrics with a polypeptide or composition as described above. The present invention further relates to a method providing colour clarification of coloured cellulose-containing fabrics, the method comprising treating coloured cellulose-containing fabrics with a polypeptide or composition as described above, and a method of providing a localized variation in colour of coloured cellulose-containing fabrics, the method comprising treating coloured cellulose-containing fabrics with a polypeptide or composition as described above. The methods of the invention may be carried out by treating cellulose-containing fabrics during washing. However, if desired, treatment of the fabrics may also be carried out during soaking or rinsing or simply by adding the polypeptide or composition as described above to water in which the fabrics are or will be immersed.

Other Enzyme Uses

In addition, a polypeptide or composition of the present invention can also be used in antibacterial formulation as well as in pharmaceutical products such as throat lozenges, toothpastes, and mouthwash.

The following Examples illustrate the invention:

EXAMPLES

General Materials and Methods

Strains

*Talaromyces emersonii* strains of the present invention are derived from ATCC16479, which was formerly *Penicillium geosmithia emersonii*. Other designations of *T. emersonii* ATCC16479 are CBS393.64, IFO31232 and IMI116815.

DNA Procedures

Standard DNA procedures were carried out as described elsewhere (Sambrook et al., 1989, *Molecular cloning: a laboratory manual*, $2^{nd}$ Ed., Cold Spring Harbor Laboratory Press, Cold Spring Harbor, N.Y.) unless otherwise stated. DNA was amplified using the proofreading enzyme Phusion polymerase (Finnzymes). Restriction enzymes were from Invitrogen or New England Biolabs.

Media and Solutions:

Potato Dextrose Agar, PDA, (Fluka, Cat. No. 70139)

| | |
|---|---|
| Potato extract | 4 g/l |
| Dextrose | 20 g/l |
| Bacto agar | 15 g/l |
| pH | 5.4 |
| Water | Adjust to one liter |
| Sterilize | 20 min at 120° C. |

*Talaromyces agar* Medium

| | |
|---|---|
| Salt fraction no. 3 | 15 g |
| Cellulose (3%) | 30 g |
| Bacto peptone | 7.5 g |
| Grain flour | 15 g |
| $KH_2PO_4$ | 5 g |
| $CaCl_2 \cdot 2aq$ | 1 g |
| Bacto agar | 20 g |
| pH | 6.0 |
| Water | Adjust to one liter |
| Sterilize | 20 min at 120° C. |

Salt Fraction Composition

The salt fraction was fitting the disclosure of WO98/37179, Table 1. Deviations from the composition of this table were $CaCl2.2aq$ 1.0 g/l, KCl 1.8 g/L, citric acid 1aq 0.45 g/L (chelating agent).

Shake Flask Media

*Talaromyces* Medium 1

| | |
|---|---|
| Glucose | 20 g/L |
| Yeast extract (Difco) | 20 g/L |
| Clerol FBA3107 (AF) | 4 drops/L |
| pH | 6.0 |
| Sterilize | 20 min at 120° C. |

*Talaromyces* Medium 2

| | |
|---|---|
| Salt fraction | 15 g |
| Cellulose | 30 g |
| Bacto peptone | 7.5 g |
| Grain flour | 15 g |
| $KH_2PO_4$ | 10 g |
| $CaCl_2 \cdot 2H20$ | 0.5 g |
| Clerol FBA3107 (AF) | 0.4 ml |
| pH | 5 |
| Water | Adjust to one liter |
| Sterilize | 20 min at 120° C. |

*Talaromyces* Medium 3

| | |
|---|---|
| Salt fraction | 15 g |
| Glucose | 50 g |
| Bacto peptone | 7.5 g |
| $KH_2PO_4$ | 10 g |
| $CaCl_2 \cdot 2H_2 0$ | 0.5 g |
| Clerol FBA3107 (AF) | 0.4 ml |
| pH | 5 |
| Water | Adjust to one liter |
| Sterilize | 20 min at 120° C. |

Spore Batch Preparation

Strains were grown from stocks on *Talaromyces* agar medium in 10 cm diameter Petri dishes for 5-7 days at 40° C. Strain stocks were stored at −80° C. in 10% glycerol.

Shake Flask Growth Protocol

Spores were directly inoculated into 500 ml shake flasks containing 100 ml of either *Talaromyces* medium 1 or 2 and incubated at 45° C. at 250 rpm in an incubator shaker for 3-4 days.

Sample Preparation

For shake flask cultures, 3 ml of culture broth was transferred to a 12 ml disposable tube and centrifuged for 10 min at 5200 g. At least 1 ml of supernatant was harvested.

Protein Analysis

Protein samples were separated under reducing conditions on NuPAGE 4-12% Bis-Tris gel (Invitrogen, Breda, The Netherlands) and stained as indicated. Gels were stained with either InstantBlue (Expedeon, Cambridge, United Kingdom), SimplyBlue safestain (Invitrogen, Breda, The Netherlands) or Sypro Ruby (Invitrogen, Breda, The Netherlands)) according to manufacturer's instructions.

For Western blotting, proteins were transferred to nitrocellulose. The nitrocellulose filter was blocked with TBST (Tris buffered saline containing 0.1% Tween 40) containing 3% skim-milk and incubated for 16 hours with anti-FLAG M2 antibody (Sigma, Zwijndrecht, The Netherlands). Blots were washed twice with TBST for 10 minutes and stained with Horse-radish-peroxidase conjugated rabbit-anti-mouse antibody (DAKO, Glostrup, Denmark) for 1 hour. After washing the blots five times with TBST for 10 minutes, proteins were visualized using SuperSignal (Pierce, Rockford, U.S.A).

Cellulase Assays

1. Wheat Straw Assay (WSU Assay).

Preparation of Pre-Treated, Washed Wheat Straw Substrate.

The washed wheat straw substrate was homogenised using an ultra-turrax, washed, lyophilized and grinded prior to analysis.

Measurement of Cellulase Activity in WSU/ml

Cellulase activity was herein measured in terms of "Wheat Straw Units" (WSU) per milliliter in a Wheat Straw assay (WSU assay). The washed wheat straw substrate was ultraturraxed, washed, lyophilized and grinded prior to analysis.

400 μl of supernatants harvested from shake flask experiments were diluted 16-fold. Duplicate, 200 μl samples were transferred to two suitable vials: one vial containing 700 μL 3% (w/w) dry matter of the pretreated, washed wheat straw substrate and 100 μl 250 mM citrate buffer, buffered at pH 4.5. The other vial consisted of a blank, where the 700 μl 3% (w/w) dry matter pretreated, washed wheat straw substrate was replaced by 700 μl water, with 100 μl 250 mM citrate buffer, buffered at pH 4.5. The assay samples are incubated for 20 and/or 60 hr at 65° C. After incubation of the assay samples, a fixed volume of $D_2O$ containing an internal standard, maleic acid is added. The amount of sugar released, is based on the signal between 5.25-5.20 ppm, relative to Dimethyl-sila-pentane-sulfonate determined by means of 1D $^1H$ NMR operating at a proton frequency of 500 MHz, using a pulse program with water suppression, at a temperature of 27° C. The cellulase enzyme solution may contain residual sugars. Therefore, the results of the assay are corrected for the sugar content of the enzyme solution.

2. Endoglucanases Activity (WBCU)

Endoglucanase catalyses the hydrolysis of carboxymethyl cellulose. The amount of reducing sugars formed during the enzyme reaction was determined with dinitrosalisylic acid reagent. The samples were incubated in the presence of carboxymethyl cellulose (Novacel, ref.394) solution 18 g/L in acetate buffer pH 4.60 at 37° C. The incubation was stopped after 60 minutes by adding sodium hydroxide solution. Samples were boiled for 5 minutes in the presence of dinitrosalisylic acid (Acros 15644500) reagent. After diluting with water, intensity of the colour was measured at 540 nm. The methodology was used as a relative method. The results were related to a cellulase composition with an officially assigned activity. The activity was expressed in WBCU units. WBCU unit is defined as the amount of cellulase that hydrolyses in one hour a number of glycosidic bonds equivalent to the production of 0.5 mg glucose under the condition of the assay. The activity was calculated using standard calculation protocols known in the art, by plotting the deltaOD$_{540}$ versus the activity of samples with known activity, followed by the calculation of the activity of the unknown samples using the equation generated form the calibration line.

Example 1

Transformation of *Talaromyces Emersonii* with Plasmids Containing Phleomycin Resistance Markers This example describes a method to transform *T. emersonii* with pAN8-1 plasmid carrying a phleomycin resistance marker (Mattern, I. E., Punt, P. J., Van den Hondel, C. A. M. J. J., 1988. A vector of *Aspergillus* transformation conferring phleomycin resistance. Fungal Genet. Newsl. 35, 25).

Transformation of *T. emersonii* with pAN8-1

Spores were grown for 16 hours at 45° C. in a rotary shaker at 250 rpm in YGG medium (per liter: 8 g KCl, 16 g glucose.H$_2$O, 20 ml of 10% yeast extract, 10 ml of 100× pen/strep, 6.66 g YNB+amino acids, 1.5 g citric acid, and 6 g K$_2$HPO$_4$). Mycelium was harvested by using Miracloth filter (Calbiochem, Nottingham, United Kingdom). For protoplast formation, per 2 g of mycelium 10 ml of STC buffer (per liter: 218 g Sorbitol (1.2 M), 7.35 g CaCl$_2$.2H$_2$O, 10 mM Tris/HCl pH7.5) and 1 ml of glucanex solution (250 mg/ml Glucanex 200G (Novozymes, Bagsvaerd, Denmark) in H$_2$O) was added. The mixture was incubated in a rotary shaker at 100 rpm at 34° C. for 90-150 minutes. Protoplasts were separated from mycelium using a Miraclot filter and STC was added to a final volume of 45 ml. The protoplast suspension was centrifuged for 5 minutes at 1560 g at 4° C. and resuspended in STC-buffer at a concentration of $10^8$ protoplasts/ml. For transformation, 200 μl of protoplast suspension was added to 10 μg of pAN8-1 DNA in TE buffer (10 mM Tris-HCl pH 7.5, 0.1 mM EDTA) and 18 μl of 0.4 M Aurintricarboxylic acid. Subsequently, 100 μl of a PEG solution (20% PEG 4000 (Merck, Nottingham, United Kingdom) in STC) was added, and after incubation of the DNA-protoplast suspension for 10 minutes at room temperature, 1.5 ml of PEG solution (60% PEG 4000 (Merck) in STC) was added slowly, with repeated mixing of the tubes. After incubation for 15 minutes at 25° C., suspensions were diluted with 2 ml of STC and mixed by inversion. Approximately 200 to 600 μl of protoplast suspension was added to 5 ml of soft agar (Regeneration medium containing 6 g/L agar, without selection) and directly plated on 10 cm petri dishes with 20 ml of Regeneration medium containing 10 μg/ml phleomycin. Regeneration medium contains per liter: 6 g NaNO$_3$, 0.52 g KCl, 1.52 g KH$_2$PO$_4$, 1.12 ml 4 M KOH, 0.52 g MgSO$_4$.7H$_2$O, 22 mg ZnSO$_4$.7H$_2$O, 11 mg H$_3$BO$_3$, 5 mg FeSO$_4$.7H$_2$O, 1.7 mg CoCl$_2$.6H$_2$O, 1.6 mg CuSO$_4$.5H$_2$O, 5 mg MnCl$_2$.4H$_2$O, 1.5 mg Na$_2$MoO$_4$.2H$_2$O, 50 mg EDTA, 10 ml 100× Pen/strep (Gibco), 2.5 g glucose, 2.5 g yeast extract, 341 g sucrose, and 20 g agar (in overlay 6 g/L).

After incubation for 4-6 days at 40° C., conidiospores of transformants were transferred to plates consisting of PDA supplemented with 10 μg/ml phleomycin and incubated for 2 days at 40° C.

PCR Analysis of Transformants on Fungal Mycelium

Transformants were incubated on Potato Dextrose Agar-containing plates for two days at 40° C. Approximately one third of a colony was incubated for 1 hour at 37° C. in 25 μl KC buffer (60 g/l KCl, 2 g/l citric acid, pH 6.2), supplemented with 5 mg/ml Glucanex 200G (Novozymes, Bagsvaerd, Denmark). Subsequently, 75 μl of DNA dilution buffer (10 mM Tris-HCl, 1 mM EDTA, 10 mM NaCl, pH 7.5) was added. Samples were incubated for 5 minutes at 98° C. and, subsequently, diluted by adding 100 μl of H$_2$O. A 5 μl aliquot of the mixture was used as template for PCR.

Primers were synthesized by Invitrogen (Breda, The Netherlands). The following PCR primers were used to amplify a 278 nucleotide fragment of the β-lactamase gene of pAN8-1:

```
Amp-For (SEQ ID NO: 1): TATGCAGTGCTGCCATAACCAT;
and

Amp-Rev (SEQ ID NO: 2): GCAGAAGTGGTCCTGCAACTTT
```

PCR conditions for the reactions: 50 μl reaction mix with 5 μl of template DNA, 20 pmol of each primer, 0.2 mM of dNTPs, 1× Phusion HF buffer and 1 U of Phusion DNA-Polymerase, according to Phusion High-Fidelity DNA Polymerase Manual (Finnzymes, Espoo, Finland), 30 s denaturation at 98° C., amplification in 30 cycles (10 s 98° C., 10 s 60° C., 15 s 72° C.), and a final incubation of 10 min at 72° C.

The results of the agarose gel is presented in FIG. 1. A specific PCR band of 278 nucleotides was observed in transformants, but not in the empty strain, indicating that transformants contain the ampicillin gene of the pAN8-1 vector. Thus, *T. emersonii* is successfully transformed with the pAN8-1 vector.

In order to determine whether pAN8-1 is integrated into the genome a Southern blot was performed. Chromosomal DNA was isolated from transformants using the Puregene Yeast and Bacteria Kit (Gentra Systems Inc., Minneapolis, USA). Transformants were grown for 16 hours in 10 ml of YGG medium at 45° C. and the mycelium was used for chromosomal DNA isolation. Lysis of the mycelium (~50 mg fresh weight) was performed by adding 250 µl Cell Suspension Buffer (Puregene kit, Gentra Systems, Minneapolis, USA) and 50 µl of Glucanex 200G (Novozymes, Bagsvaerd, Denmark, 100 mg/ml in KCl-citrate buffer pH6.2). The resuspended mycelium was incubated at 37° C. for 1 hour. Subsequently, a centrifugation step was performed (1 minute at 15.700 g) and the formed pellet was resuspended in 600 µl of Cell Lysis Solution and 3 µl Proteinase K solution (20 mg/ml, Invitrogen, Breda, The Netherlands) was added followed by an incubation at 55° C. for 1 hour. The subsequent steps including RNAse Treatment, Protein Precipitation, DNA Precipitation and DNA Hydration were performed according to suppliers protocol for Gram positive bacteria.

Chromosomal DNA was digested with MluI and electrophoresed on a 0.7% (w/v) agarose gel. DNA was transferred to Hybond N+ (GE Healthcare, Eindhoven, The Netherlands) by vacuum blotting. Blots were subsequently pre-hybridised for approximately 1 hour at 42° C. in ECL Gold hybridisation buffer (GE Healthcare, Eindhoven, The Netherlands) and hybridised overnight at 42° C. with a labelled probe representing the ampicillin resistance gene present on pAN8-1. The probe was obtained by PCR using primer Amp-For (SEQ ID NO: 1) and Amp-Rev (SEQ ID NO: 2) and pAN8-1 as template. PCR conditions for the reaction: 30 s denaturation at 98° C., amplification in 30 cycles (10 s 98° C., 10 s 60° C., 20 s 72° C.), and a final incubation of 5 min at 72° C. The probe was labelled according to the ECL method (GE Healthcare, Eindhoven, The Netherlands). After hybridisation, blots were washed and treated with detection reagent according to the ECL method (GE Healthcare, Eindhoven, The Netherlands). Signal was detected using the Biorad ChemiDoc XRS apparatus according to supplier's instructions.

Figure 2:
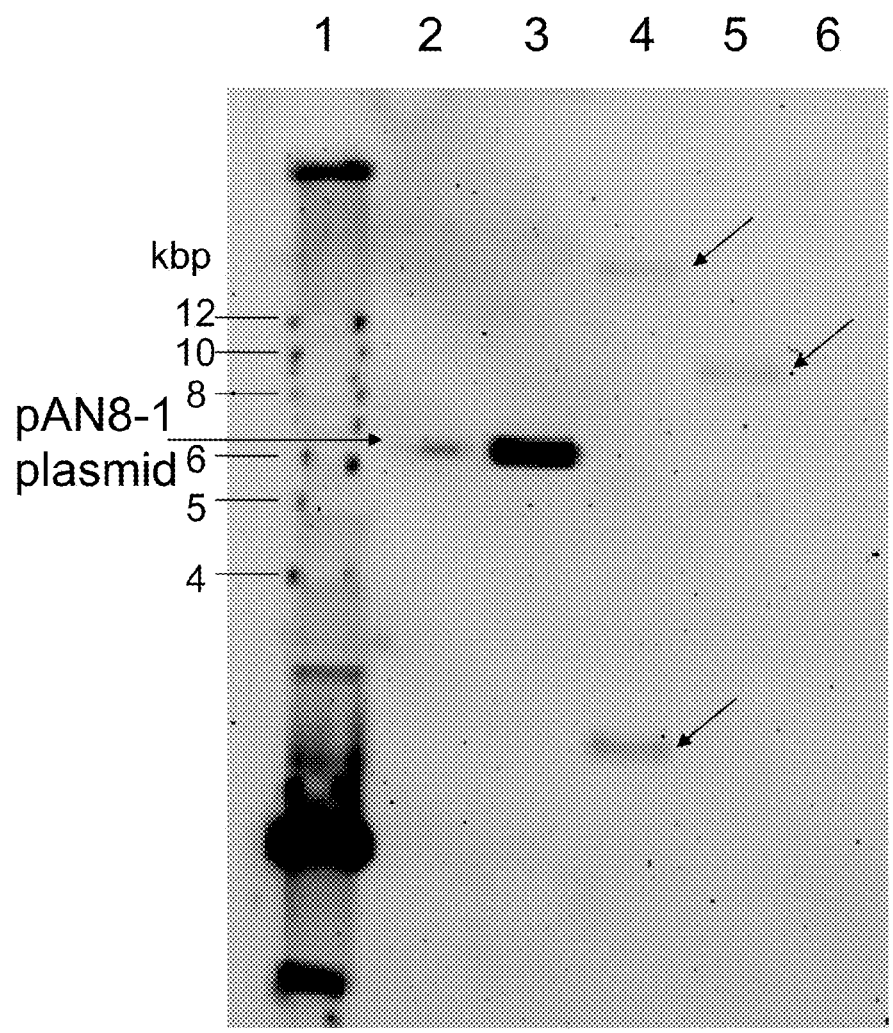
FIG. 2. Detection of pAN8-1 integration into the *T. emersonii* genome. Southern blot detection of pAN8-1 DNA using a labelled β-lactamase probe. Lane 1 contains a molecular weight marker; Lane 2 and 3 contain, respectively, 0.5 and 5 ng of pAN8-1 plasmid DNA; Lane 4 and 5 contains MluI digested chromosomal DNA of two different pAN8-1 *T. emersonii* transformants (specific bands are indicated by arrows); lane 6 contains MluI digested chromosomal DNA of an empty strain.

The Southern blot result is presented in FIG. 2. In lanes 2 and 3, two concentrations of pAN8-1 plasmid were loaded on the gel, which were detected as 6.1 kbp bands on the Southern blot. The 6.1 kbp band was not observed in pAN8-1 *T. emersonii* transformants (lanes 4 and 5), but, instead, the β-lactamase probe hybridised with chromosomal DNA fragments of different lengths, indicating that the plasmid is integrated into the genome.

The stability of the transformed phenotype was checked by purifying pAN8-1 transformants on Potato Dextrose Agar-containing plates without phleomycin selection. Single colonies were subsequently purified on Potato Dextrose Agar-containing plates with phleomycin selection. Out of 20 transformants tested, all appeared to be phleomycin resistant. Thus, the pAN8-1 vector is stably integrated into the *T. emersonii* genome.

This experiment clearly demonstrated that *T. emersonii* can be transformed with a plasmid, which is stably integrated into the *T. emersonii* genome.

Example 2

Transformation of *Talaromyces Emersonii* with Plasmids Encoding *Talaromyces emersonii* Cellulases This example describes the cloning and expression of FLAG-tagged *T. emersonii* beta-glucanase CEB protein in *T. emersonii*.

Figure 3:
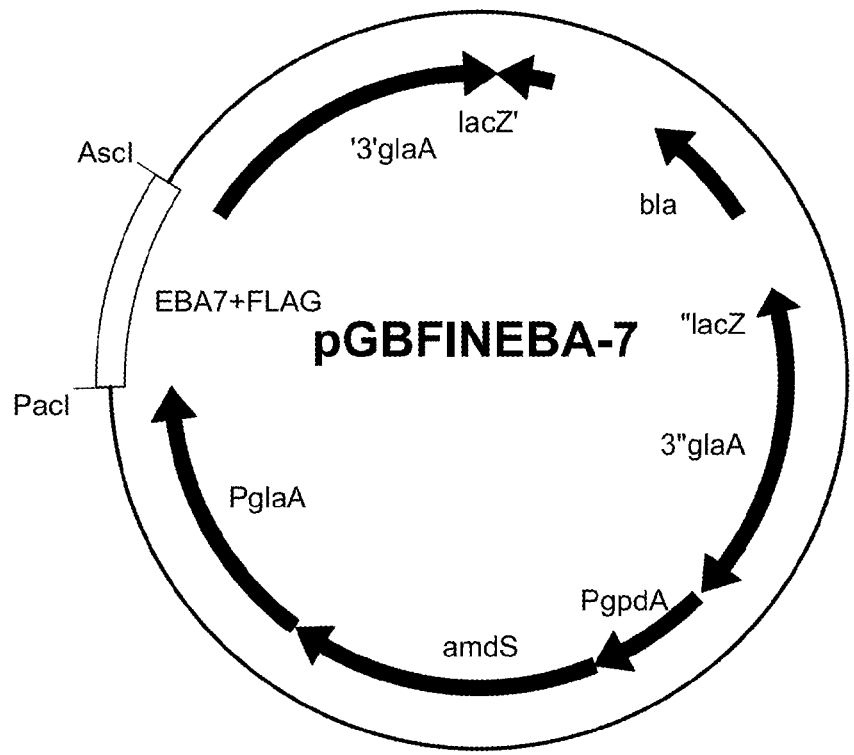
FIG. 3. Map of pGBFINEBA7 for expression of FLAG-tagged *T. emersonii* beta-glucanase CEB protein. pGBFINEBA7 is a pGBFIN5-based plasmid. Depicted are the FLAG-tagged *T. emersonii* beta-glucanase CEB protein (EBA7+FLAG) expressed from the *Aspergillus niger* glucoamylase promoter (PglaA). In addition, the selection marker gene (amdS), expressed from the *Aspergillus nidulans* glyceraldehyde-3-phosphate dehydrogenase promoter (Pgpd) and the glucoamylase flanks (3' glaA and 3"glaA) of the expression cassette are depicted.

Cloning of *T emersonii* Expression Plasmid pGBFINEBA7 Encoding FLAG-Tagged *T. emersonii* Beta-Glucanase CEB Protein The gene encoding *T. emersonii* beta-glucanase CEB protein and a C-terminal FLAG-tag was synthesised by DNA2.0 (Menlo Park, USA) and cloned as PacI/AscI fragment into pGBFIN-5, which plasmid is described in WO 9932617. The pGBFIN5 expression vector comprises the glucoamylase promoter, cloning site, terminator region, an amdS marker operably linked to the gpd promoter, and 3' and 3" glaA flanks. The amino acid and nucleotide sequences of the FLAG-tagged *T. emersonii* beta-glucanase CEB protein is represented by SEQ ID NO: 3 and SEQ ID NO: 4, respectively. FIG. 3 represents a map of pGBFINEBA7 containing the *T. emersonii* beta-glucanase CEB protein under control of the glucoamylase promoter within vector pGBFIN-5.

Transformation of *T. emersonii* with pGBFINEBA7

*T. emersonii* transformation was performed according to the protocol described in Example 1, with the exception that *T. emersonii* was co-transformed with 2 µg of pAN8-1 and 10 µg of pGBFINEBA7 DNA. Co-transformants were identified by PCR analysis. The presence of pAN8-1 plasmid was determined by using primer Amp-For (SEQ ID NO: 1) and Amp-Rev (SEQ ID NO: 2). The following primers were used to amplify the *T. emersonii* β-glucanase CEB coding sequence:

EBA7-For (SEQ ID NO: 5): CAGCTTAATTAACACCGT-CAAAATGGACCGTATAC; and

EBA7-Rev (SEQ ID NO: 6): GGCGCGCCTTTACTTGT-CATCATCATCCTTGTAGTCTGACTG-GAAGGTGCTGCCAAT G. PCR conditions were used as described in Example 1.

*T. emersonii* Shake Flask Fermentations

Transformants were grown in shakeflasks using *Talaromyces* medium 1 and *Talaromyces* medium 2, and samples were taken after 72 hours. Proteins in 65 µl of supernatant were precipitated by adding 228 µl TCA-aceton (1.2 g trichloric acid, 9 ml of acetone, 1 ml of $H_2O$. After precipitating for 3 hours at −20° C., samples were centrifuged at 14.000 rpm at 4° C. for 10 min in an eppendorf centrifuge and pellets were washed with acetone. Dried pellets were dissolved in 1× sample buffer (25 µl of LDS sample buffer (Invitrogen, Breda, The Netherlands), 10 µl of reducing agent (Invitrogen, Breda, The Netherlands), 65 µl of $H_2O$).

Protein Analysis

Protein samples were separated under reducing conditions on NuPAGE 4-12% Bis-Tris gel (Invitrogen, Breda, The Netherlands). Gels were incubated with InstantBlue (Expedeon, Cambridge, United Kingdom) according to manufacturer's instructions or used for Western blotting using a FLAG-specific antibody.

Figure 4A:
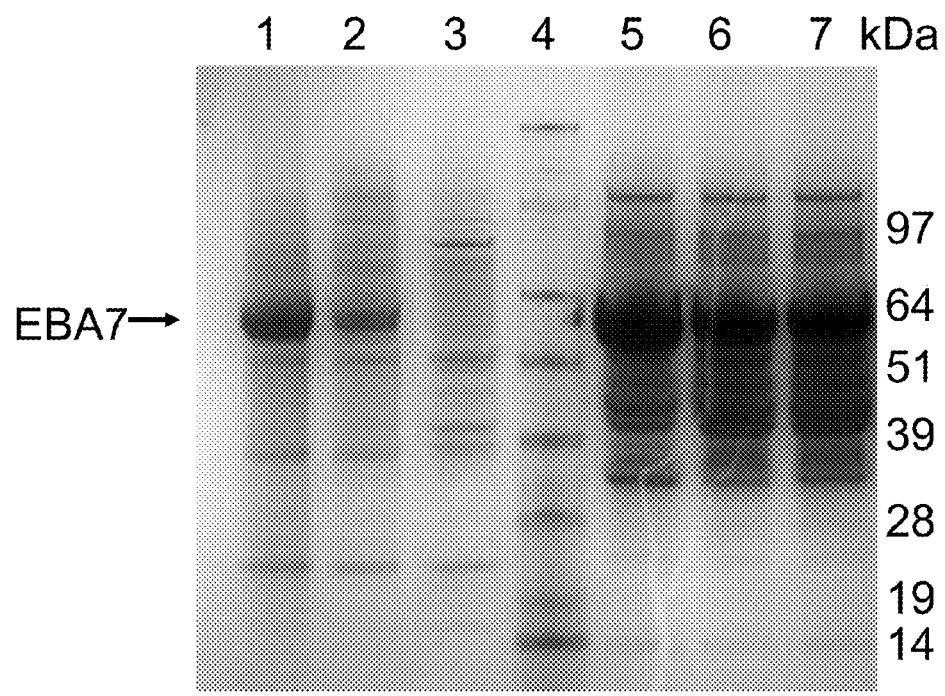
FIG. 4. Detection of FLAG-tagged *T. emersonii* beta-glucanase CEB protein, expressed in *T. emersonii*.
Figure 4B:
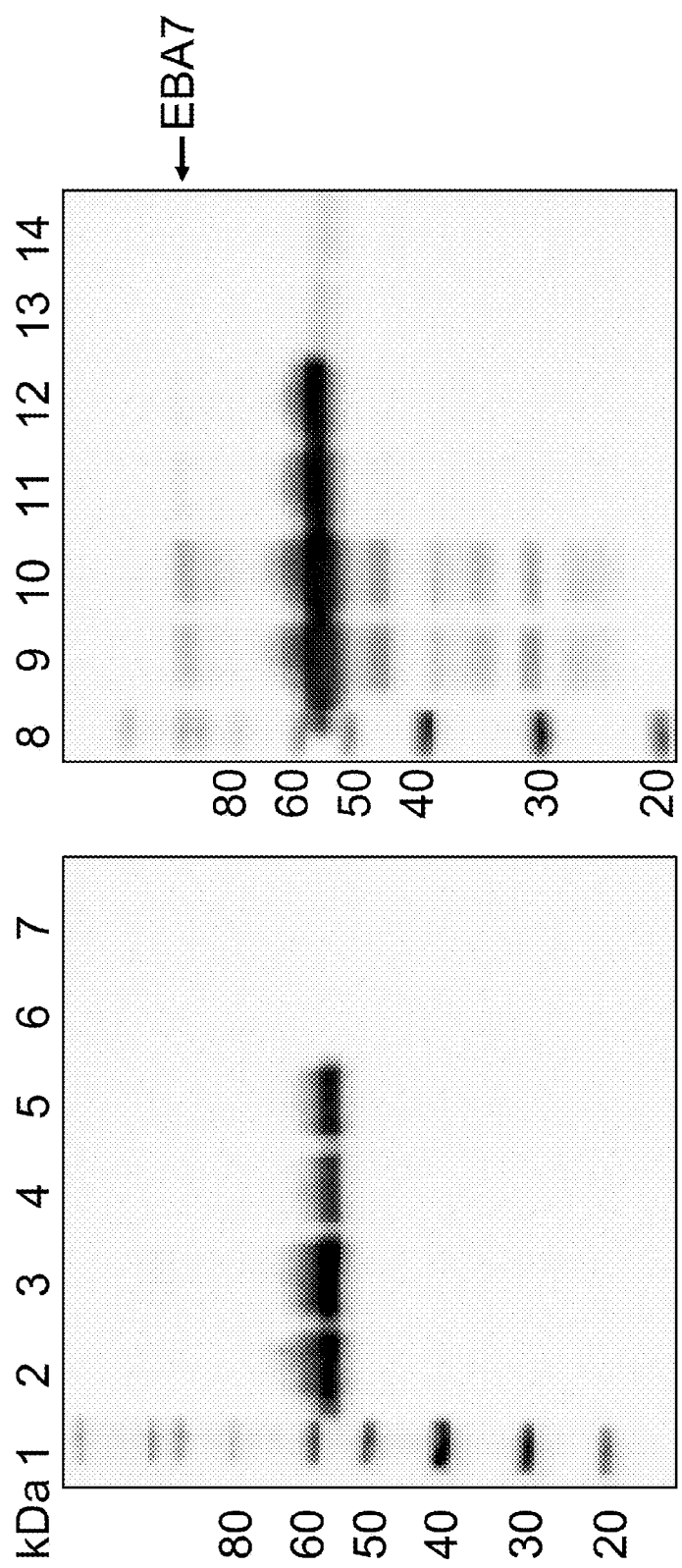

The results of the InstantBlue protein gel stain and Western blotting are presented in FIGS. 4A and 4B, respectively. The InstantBlue stained gel showed a specific EBA7-FLAG band of about 58 kDa in supernatants of pGBFINEBA7 transformants grown in *Talaromyces* medium 1 (lanes 1 and 2). The EBA7-FLAG band could not be observed in supernatants of transformants grown in *Talaromyces* medium 2 due to the high protein background of proteins that are induced on cellulose (lanes 5 and 6). However, on Western blot we could observe a specific EBA7-FLAG protein band in supernatants of pGBFINEBA7 transformants grown in each of the media, indicating that EBA7-FLAG protein is produced in glucose and cellulose based medium. As we could not detect any FLAG signal on Western blot in supernatants of the empty strain (lanes 6 and 7, 13 and 14 in FIG. 4B), the expressed protein is a recombinant protein.

Copy Number Determination of pGBFINEBA7 in *T. emersonii* Transformants

Two transformants were tested for EBA7-FLAG expression, transformant 1#6 and 1#14, and more product was observed in transformant 1#6 (compare lane 1 and lane 2 in FIG. 4A; compare lanes 2+3 and lane 4+5 in FIG. 4B). In order to test whether the difference in expression level is due to differences in copy number, chromosomal DNA was isolated and used for a PCR reaction. Chromosomal DNA was isolated from mycelium grown for 24 hours at 45° C. in a rotary shaker at 250 rpm in YGG medium using the FastDNA Spin Kit (MP Biomedicals, Solon—USA) according to supplier's manual. Approximately 100 ng of DNA was used as template for PCR. Part of the expression cassette was amplified using primer EBA7-For (SEQ IS NO:5) and primer EBA7-Rev (SEQ IS NO: 6). Actin primers were used as a control for the amount of DNA that was used for the PCR reactions. The following primers were used to amplify part of the *T. emersonii* actin gene:
Actin-For (SEQ ID NO: 8): CCACCTTCAACTCCATCATGAAG; and actin-Rev (SEQ ID NO: 9): TTAGAAGCACTTGCGGTGGA. The PCR mixture was the same as described in EXAMPLE 1 and following PCR conditions were used: 30 s denaturation at 98° C., amplification in 20 cycles (10 s 98° C., 15 s 60° C., 30 s 72° C.), and a final incubation of 5 min at 72° C.

Figure 4C:
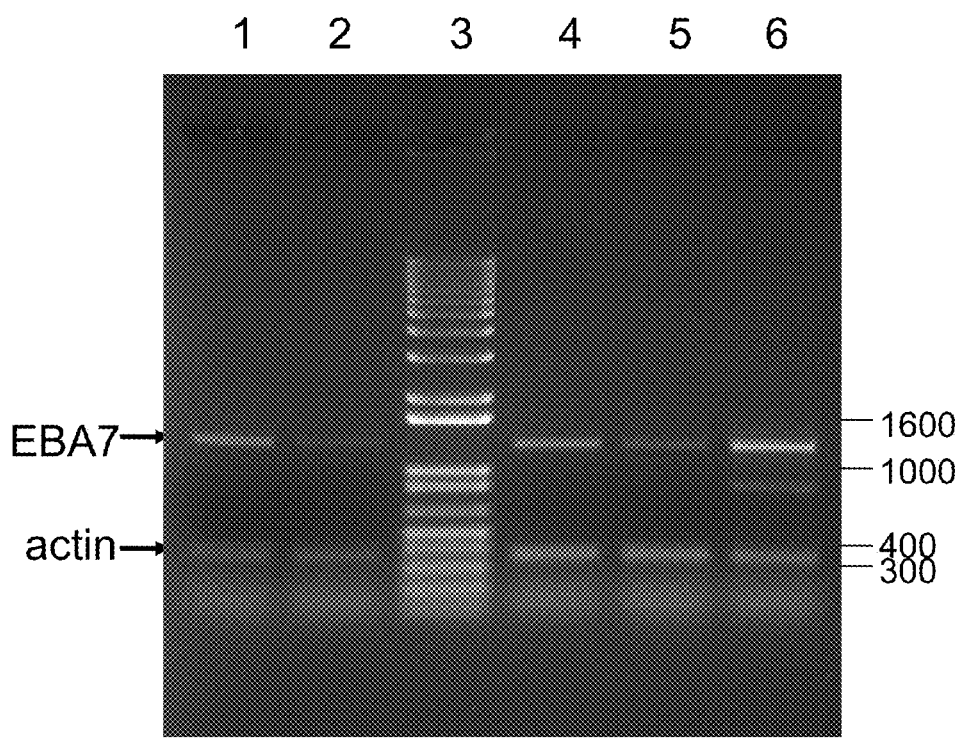

As is shown in FIG. 4C, transformant 1#6 (lane 1) showed a stronger expression cassette PCR signal compared to transformant 1#14 (lane 2), which is in agreement with the difference in expression level. The result indicates that transformant 1#6 contains multiple copies of pGBFINEBA7.

Thus, a recombinant protein was successfully expressed in *T. emersonii*. In addition, it is possible to generate transformants with multiple copies of the gene of interest.

Example 3

Cellulase Activity Measurement of Supernatants Isolated from *Talaromyces emersonii* Transformed with pGBFINEBA7

This example describes the measurement of endoglucanase activity in supernatants of *T. emersonii* transformed with pGBFINEBA7 (see EXAMPLE 2 for description of transformant). Activity was measured by using carboxymethyl cellulose as substrate and detecting reducing sugars by using dinitrosalisylic acid reagent.

*T. emersonii* transformants containing pGBFINEBA7 (see EXAMPLE 2) were used to inoculate 100 ml of *Talaromyces* medium 1 and incubated at 45° C. at 250 rpm in an incubator shaker for 3 days. Supernatants were harvested and used to measure endoglucanase activity. The results of the tests in the endoglucanase activity assay are shown in Table 1.

TABLE 1

Results of endoglucanse activity measurement in supernatants of an empty strain and a *T. emersonii* transformant

| Strain | Endoglucanse activity (WBCU/ml) |
|---|---|
| pGBFINEBA7 1#6 | 321 |
| Empty strain | <10 |

*T. emersonii* transformants expressing recombinant *T. emersonii* endoglucanase showed at least 32 times more endoglucanase activity compared to the wild-type strain.

This experiment clearly demonstrated that recombinant *T. emersonii* endoglucanase expressed in *T. emersonii* is active. Therefore, enzymes can be expressed in *T. emersonii*.

Example 4

Comparison Between Expression Driven by the Glucoamylase Promoter and the Glyceraldehyde-3-Phosphate Dehydrogenase Promoter in *Talaromyces emersonii*

This example describes the cloning and expression of FLAG-tagged *T. emersonii* beta-glucanase CEB protein in *T. emersonii* under control of the glyceraldehyde-3-phosphate dehydrogenase (gpd) promoter. Expression is compared with expression of pGBFINEBA7.

Cloning of *T. emersonii* Expression Plasmid pGBFIN-Pgpd-EBA7 Encoding FLAG-Tagged *T. emersonii* Beta-Glucanase CEB Protein Driven by the Gpd Promoter The gene consisting of the gpd promoter and the coding region of *T. emersonii* beta-glucanase CEB protein and a C-terminal FLAG-tag was synthesised by DNA2.0 (Menlo Park, USA) and cloned via a 3-point ligation as XhoI/HindIII, HindIII/AscI fragments into pGBFIN38, which plasmid is described in WO2008053018. The pGBFIN38 expression vector comprises the gpd promoter, cloning site, terminator region, an amdS marker operably linked to the gpd promoter, and 3' and 3" glaA flanks. The nucleotide sequences of the gpd promoter and Kozak sequence is represented by SEQ ID NO: 7. The amino acid and nucleotide sequences of the FLAG-tagged *T. emersonii* beta-glucanase CEB protein is represented by SEQ ID NO: 3 and SEQ ID NO: 4, respectively. FIG. 5 represents a map of pGBFIN-Pgpd-EBA7 containing the *T. emersonii* beta-glucanase CEB protein under control of the gpd promoter within vector pGBFIN-38.

Transformation of *T. emersonii* with pGBFIN-Pgpd-EBA7

Transformation of *T. emersonii* with pGBFIN-Pgpd-EBA7 was performed as described in EXAMPLE 2.

*T. emersonii* Shake Flask Fermentations

*T. emersonii* transformants containing either pGBFINEBA7 (transformant 1#6, see EXAMPLE 2) or pGBFIN-Pgpd-EBA7 were used for shake flask fermentations. Shake flask fermentations and analysis of protein expression by Western blot analysis using a FLAG-specific antibody were performed as described in EXAMPLE 2.

The results of the Western blot is presented in FIG. 6. Several dilutions of supernatants were separated on gel to be able to compare expression between transformants. Supernatants (1:100 dilution) of day 3 cultures of transformant 1#6 in which EBA7 is driven by the glaA promoter showed a strong (overexposed) EBA7-FLAG band (lanes 9 and 15). Undiluted day 3 supernatant of three transformants in which EBA7 is driven by the gpd promoter (lanes 5, 8 and 14) showed a band on Western blot, but the band was of less intensity compared to the 100 times diluted supernatant of transformant 1#6. No expression of EBA7-FLAG was observed in supernatants of an empty strain (lanes 1, 10 and 11). Copy number estimations by PCR revealed that transformant 8#18 contains the lowest amount of copies, while transformants 8#32 contains the highest amount of copies (FIG. 4C, lanes 4-6), which correlates with EBA7-FLAG expression observed on Western blot (FIG. 6, compare lanes 4, 7 and 13). As the copy number of pGBFINEBA7 transformant 1#6 is comparable to pGBFIN-Pgpd-EBA7 transformant 8#14 (compare lane 1 with lane 4 in FIG. 4C), while EBA7-FLAG expression in supernatants of transformant 1#6 is much higher compared to expression in transformant 8#14, the glaA promoter is stronger than the gpd promoter.

Endoglucanase Activity Assay (WBCU)

Samples of the shake flask experiment were also analysed for endoglucanase activity. The same method was performed as described in EXAMPLE 3. The results of the tests in the endoglucanase activity assay are shown in Table 2.

TABLE 2

Results of endoglucanse activity measurement in supernatants of an empty strain and T. emersonii transformants

| Strain | Endoglucanase activity (WBCU/ml) |
|---|---|
| pGBFINEBA7 1#6 | 321 |
| pGBFIN-Pgpd-EBA7 8#14 | <10 |
| pGBFIN-Pgpd-EBA7 8#18 | <10 |
| pGBFIN-Pgpd-EBA7 8#32 | <10 |
| Empty strain | <10 |

Endoglucanase activity in supernatants of transformants of pGBFIN-Pgpd-EBA7 was not increased above the background of the assay (<10 WBCU/ml), while endoglucanase activity in supernatants of transformants of pGBFINEBA7 1#6 was at least 32 times higher compared to the wild-type strain (321 WBCU/ml).

Example 5

Overexpression of Multiple *Talaromyces Emersonii* Cellulases in *Talaromyces emersonii*

This example describes the cloning and expression of *T. emersonii* cellobiohydrolase-I (CBHI), *T. emersonii* cellobiohydrolase-II (CBHII), *T. emersonii* beta-glucanase CEA (EG), and *T. emersonii* β-glucosidase (BG) in *T. emersonii*. In addition, cellulase activity of transformants is compared with cellulase activity of an empty strain after growing the strains on glucose.

Cloning of *T emersonii* Genes in Expression Vectors

The genes encoding *T. emersonii* cellobiohydrolase-I (CBHI), *T. emersonii* beta-glucanase CEA (EG), and *T. emersonii* β-glucosidase (BG) were synthesised by DNA2.0 (Menlo Park, USA) and cloned as EcoRI/SnaBI fragment into the pGBTOP12 vector, comprising the glucoamylase promoter and terminator sequence, resulting in vector pGBTOPEBA205, pGBTOPEBA8 and pGBTOPEBA4, respectively. For cloning purposes, 198 nucleotides of the 3' part of the glucoamylase promoter was also synthesised with the genes. The amino acid sequences of the *T. emersonii* cellobiohydrolase-I (CBHI), *T. emersonii* beta-glucanase CEA (EG), and *T. emersonii* β-glucosidase (BG) are represented by SEQ ID NO: 10, 12, and 14, respectively. The DNA sequences of the genes are represented by SEQ ID NO: 11, 13 and 15, respectively. FIG. 7 represents a map of a pGBTOPEBA205 containing the *T. emersonii* CBHI protein under control of the glaA promoter within vector pGBTOP12. pGBTOPEBA205 is representative for pGBTOPEBA8, which comprises *T. emersonii* EG, and pGBTOPEBA4, which comprises *T. emersonii* BG.

The gene encoding *T. emersonii* cellobiohydrolase-II (CBHII), was obtained from a *T. emersonii* cDNA library described in patent WO/2001/070998. FIG. 8 represents a map of pGBFINEBA176 containing the *T. emersonii* CBHII protein under control of the glaA promoter within vector pGBFIN11. The amino acid sequence and nucleotide sequence are represented by SEQ ID NO: 16 and 17, respectively.

Transformation of *T. emersonii* with Constructs Encoding Cellulases

Transformation of *T. emersonii* with constructs encoding cellulases was performed as described in EXAMPLE 1. In total, 10 μg of DNA was used to co-transform *T. emersonii:* 1 μg of pAN8-1 and 2 μg of each of the vectors pGBTOPEBA4, pGBTOPEBA8, pGBTOPEBA205 and pGBFINEBA176.

Screening for Transformants Expressing all 4 Cellulases

Transformants were picked from plates and further grown into 96 wells microtiter plates (MTP) containing *Talaromyces* agar medium for 5 days at 40° C. The plates were replica plated using a 96-pin replicator into 96-well MTPs containing PDA medium. The MTP plates were incubated for 3 days at 40° C. and used to harvest spores for shake flask analysis. To do this, 100 μl of *Talaromyces* medium 1 was added to each well and after resuspending the mixture, 30 μl of spore suspension was used to inoculate 170 μl of *Talaromyces* medium 1 in MTP plates. The 96-well plates were incubated in humidity shakers (Infors) for 44° C. at 550 rpm, and 80% humidity for 96 hours. Plungerplates were used to push down the mycelium and, subsequently, approximately 100 μl of supernatant was harvested per well.

Approximately 10 μl of supernatant was analysed for protein expression using the E-PAGE 96 Protein electrophoresis system (Invitrogen, Breda, The Netherlands). Gels were stained with SimplyBlue protein staining and transformants expressing multiple cellulases were selected. Spores of interesting transformants were harvested from MTP master plates and used for spore batch preparations.

*T. emersonii* Shake Flask Fermentations and Sample Analysis

*T. emersonii* transformants expressing one or more cellulases were used for shake flask fermentations in *Talaromyces* medium 2 containing 5% of glucose. Analysis of protein expression by SDS-PAGE analysis was performed as described in EXAMPLE 2. Proteins were visualised using SYPRO Ruby protein straining.

The results of the SYPRO Ruby stained SDS-PAGE gel is presented in FIG. 9A. The different transformants expressed different combinations and expression levels of cellulases. The supernatant of transformant 20 (strain 20), contained all 4 cellulases, while, in contrast, no cellulase proteins were observed in the empty strain (FBG142). Therefore, multiple cellulases can simultaneously be overexpressed in *T. emersonii* in the presence of glucose.

Figure 9B:
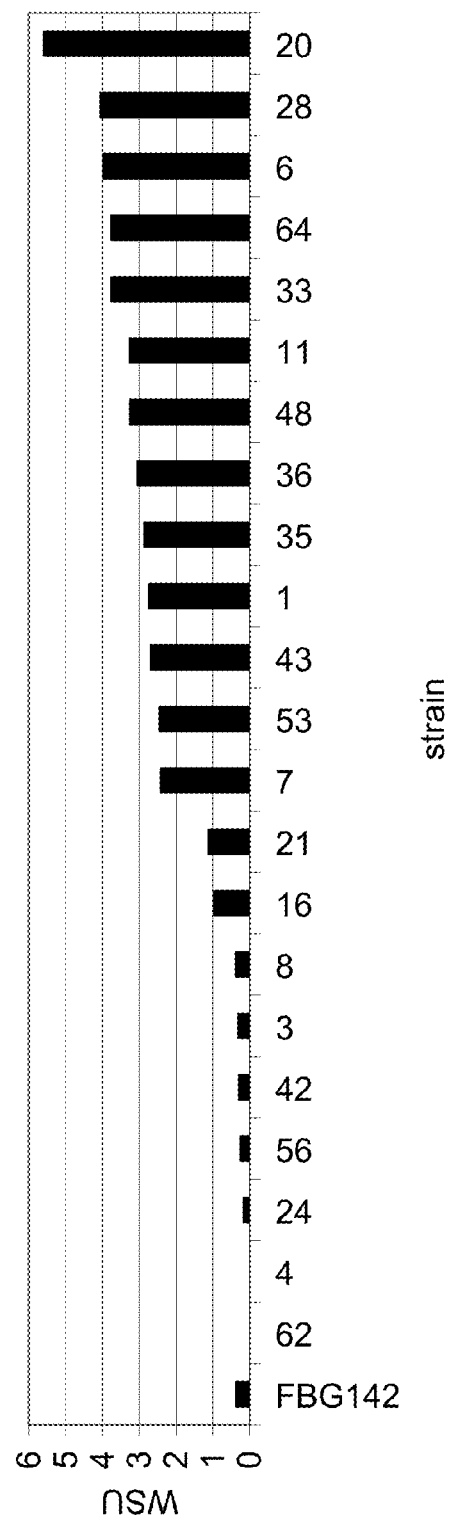

In order to test cellulase activity in *T. emersonii* transformants expressing one or more cellulases, WSU activity was measured in supernatants of an empty strain and the transformants. The results of the WSU assay is shown in FIG. 9B. In supernatants harvested after 72 hours from cultures of the empty strain grown in medium containing glucose no WSU activity could be measured. In contrast, in transformants a range of activities could be observed.

Transformant 20 expressing all 4 cellulases showed highest activity: almost 6 WSU/ml, or 5 WSU/ml or more. Transformants 20 and 28 had an activity of 4 WSU/ml or more, Transformants 20, 28, 6, 64, 33, 11 and 48 had an activity of 3 WSU/ml or more, Transformants 20, 28, 6, 64, 33, 11, 48, 36, 35 and 1 had an activity of 2.5 WSU/ml or more, and Transformants 20, 28, 6, 64, 33, 11, 48, 36, 35, 1, 43, 53 and 7 had an activity of 2 WSU/ml or more. All other transformants had an activity well below 1.5 WSU/ml.

To test whether transformant 20 also produced cellulase activity in the absence of an inducer, a shake flask fermentation was performed using *Talaromyces* medium 3. Supernatants were harvested at day 3, 4 and 5 and analysed for WSU activity. The results of the WSU assay are shown in Table 3.

TABLE 3

Results of WSU activity measurement in supernatants of an empty strain and *T. emersonii* transformant 20 in *Talaromyces* medium 3.

| Strain | cellulase activity (WSU/ml) | | |
|---|---|---|---|
|  | Day 3 | Day 4 | Day 5 |
| Transformant 20 (multiple recombinant cellulases) | 6.1 | 7.7 | 8.1 |
| Empty strain | 0.0 | 0.4 | 0.9 |

No cellulase activity was observed in day 3 sups of an empty strain, while some activity was observed at later timepoints. In contrast, the transformant overexpressing multiple cellulases under control of the glaA promoter showed WSU activity at day 3 (6.1 WSU/ml), and the activity further increased over time.

This experiment strongly indicates that *T. emersonii* transformants comprising multiple (for example 4 in this example) cellulases under control of the glaA promoter are able to produce cellulase activity in glucose containing medium with and without cellulose. The transformant can be obtained by screening a pool of transformants that have been transformed with 4 cellulase constructs.

Example 6

Second Transformation of *Talaromyces emersonii* Transformants Overexpression Multiple Talaromyces Emersonii Cellulases This example describes the second transformation of transformant EBAT147-1 with (hemi)cellulases and the second selection marker hygromycin B. The cloning of *T. emersonii* unknown protein, *T. emersonii* swollenin, *T. emersonii* acetyl xylan esterase and *T. emersonii* xylanase is described, and the transformation of *T. emersonii* transformant EBAT147-1 with *T. emersonii* cellobiohydrolase-II (CBHII), *T. emersonii* beta-glucanase CEA (EG), *T. emersonii* β-glucosidase (BG) *T. emersonii* unknown protein, *T. emersonii* swollenin, *T. emersonii* acetyl xylan esterase and *T. emersonii* xylanase.

Cloning of *T. emersonii* (Hemi)Cellulases in Expression Vectors

The genes encoding *T. emersonii* unknown protein and *T. emersonii* swollenin, were synthesised by DNA2.0 (Menlo Park, USA) and cloned as EcoRI/SnaBI fragment into the pGBTOP12 vector, comprising the glucoamylase promoter and terminator sequence, resulting in vector pGBTOPEBA224, and pGBTOPEBA225, respectively. For cloning purposes, 198 nucleotides of the 3' part of the glucoamylase promoter was also synthesised with the genes. The amino acid sequences of the *T. emersonii* unknown protein and *T. emersonii* swollenin are represented by SEQ ID NO: 18 and 20, respectively. The DNA sequences of the genes are represented by SEQ ID NO: 19 and 21, respectively. pGBTOPEBA205 (FIG. 7) is representative for pGBTOPEBA224, which comprises *T. emersonii* unknown protein, and pGBTOPEBA225, which comprises *T. emersonii* swollenin.

The genes encoding *T. emersonii* acetyl xylan esterase (ACE) and *T. emersonii* xylanase were obtained from a *T. emersonii* cDNA library described in patent WO/2001/070998. pGBFINEBA176 (FIG. 8) is representative for pGBFINEBA193, which comprises *T. emersonii* ACE and pGBFINEBA179 which comprises *T. emersonii* xylanase. The amino acid sequences of the *T. emersonii* ACE and *T. emersonii* xylanase are represented by SEQ ID NO: 22 and 24, respectively. The DNA sequences of the genes are represented by SEQ ID NO: 23 and 25, respectively.

Transformation of *T. emersonii* with Constructs Encoding (Hemi)Cellulases

Transformation of *T. emersonii* with constructs encoding cellulases was performed as described in EXAMPLE 5, with the exception that instead of pAN8-1, carrying the phleomycin selection marker, pAN7 carrying the hygromycin B selection marker was used (Punt P J, Oliver R P, Dingemanse M A, Pouwels P H, van den Hondel C A. 1987. Transformation of *Aspergillus* based on the hygromycin B resistance marker from *Escherichia coli*. Gene. 1987; 56(1):117-24. In total, 19 μg of DNA was used to co-transform *T. emersonii*: 1 μg of pAN7-1, 1 μg of each of the vectors pGBTOPEBA4, pGBTOPEBA8, and pGBFINEBA176, and 2.5 μg of each of the vectors pGBTOPEBA205, pGBTOPEBA224, pGBTOPEBA225, pGBFINEBA179 and pGBFINEBA193.

Screening for Transformants with Improved Cellulase Activity.

Transformants were picked from plates and further analysed as described in Example 5. Based on SDS-PAGE and WSU results, the most interesting transformant, EBAT147-2, was selected for spore batch preparation and tested in a 10-liter batch fermentation (see EXAMPLE 7).

Methods of Examples 7 and 8

Protein Measurement Assays

1. Total Protein

The method was a combination of precipitation of protein using trichloro acetic acid (TCA) to remove disturbing substances and allow determination of the protein concentration with the colorimetric Biuret reaction. In the Biuret reaction, a copper (II) ion is reduced to copper (I), which forms a complex with the nitrogens and carbons of the peptide bonds in an alkaline solution. A violet color indicates the presence of proteins. The intensity of the color, and hence the absorption at 546 nm, is directly proportional to the protein concentration, according to the Beer-Lambert law. The standardisation was performed using BSA (Bovine Serum Albumine) and the protein content was expressed in g protein as BSA equivalent/L or mg protein as BSA equivalent/ml. The protein content was calculated using standard calculation protocols known in the art, by plotting the OD546 versus the concentration of samples with known concentration, followed by the calculation of the concentration of the unknown samples using the equation generated from the calibration line.

2. Individual Proteins Using APEX Proteomics Analysis

Materials

LC-MS/MS system consisted of an Accela and an LTQ-Velos from Thermo Fisher (San Jose, Calif., USA). Columns were purchased from Agilent:Zorbax 2.1 mm×5 mm C18 column 1.8 _m particles. A Biofuse fresco from Heraeus centrifuge was used for centrifugation of eppendorf tubes, a Beckman Coulter Allegra X-15R was used for centrifugation of Greiner tubes. A thermomixer comfort from Eppendorf (Hamburg, Germany) was used for incubations and Eppendorf Lo-bind tubes were used for all experiments. Database searches were performed, using the Sorcerer 2 (SageN, San Diego, Calif., USA) search engine operating the Trans-Proteomics Pipeline (TPP).

The identification results were processed using Absolute Protein Expression software (APEX) http://pfgrc.jcvi.org/index.php/bioinformatics/apex.html, freeware to obtain protein quantities.

Buffers A and B LC-MS grade 0.1% Formic Acid (FA) in water and 0.1% FA in acetonitrile respectively were purchased from Biosolve (Valkenswaard, The Netherlands). Bovine Serum Albumin (BSA) Urea, Iodo Acetamide (IAA) and Trichloroacetic acid (TCA), 6.1 N solution, were purchased from Sigma Aldrich (St. Louis, Mo., USA). The TCA solution was 4.5 times diluted to obtain a 20% TCA solution. Dithiothreitol (DTT) was purchased from Roche Applied Science (Indianapolis Ind., USA). Formic acid (FA) was purchased from JT Baker (Phillipsburg, N.J., USA). Sequencing grade trypsin was purchased from Roche applied science (Penzberg, Germany).

TCA Precipitation and Digestion

Samples were carefully de-frozen and stored on ice as much as possible during sample preparation. The samples were diluted to a protein concentration of 5 mg/ml.

Hundred µl sample and 50 µl 0.1 mg/ml BSA were 1:1 diluted with 20% TCA. Samples were incubated at 4° C. for 30 minutes and the proteins were pelleted by centrifugation 10 minutes at 13000 rpm 4° C. The supernatant was removed and the pellets were washed with 200 µl acetone −20° C. Again the proteins were pelleted by centrifugation 10 minutes at 13000 rpm 4° C. and the supernatant was removed.

The washed pellets were dissolved in 75 µl 8M urea. This solution was diluted with 392.5 µl 100 mM NH4HCO3. Five µl 500 mM DTT was added and the samples were incubated at room temperature for 30 minutes under maximum agitation in a Thermomixer. The cysteines were alkylated by adding 13.5 µl 550 mM IAA and incubation at room temperature for 30 minutes under maximum agitation in a Thermomixer in the dark. Digestion was performed by adding 20 µl 250 µg/ml trypsin pH 3 and incubation at 37° C. over night under maximum agitation in the Thermomixer. Another 5 µl of 250 µg/ml trypsin pH 3 was added and digestion was continued for 3 hours at 37° C. to ensure completion.

The samples were analyzed on the Accela LTQ-Velos system (Thermo Electron).
- Column: Agilent 2.1 mm×5 mm C18 column 1.8 µm particles
- Gradient 80 minutes from 5-40% AcN 0.1% Formic Acid
- 2 minutes 40-60% AcN 0.1% Formic Acid
- Flow 400 µL/min
- Injection volume: 20 µl
- Total runtime including injection, column washing and re-equilibration 85 minutes
- MS method: 10th order double play enhanced MS m/z 300-2000 and MS/MS on the top 10 peaks
- Charge state rejection only allowing 2+ and 3+ ions
- Dynamic exclusion: repeat 1, exclusion duration 10 seconds
- Data Analysis Using Sorcerer and Spotfire The data were searched against the *Talaromyces emersonii* database (TEMER), which was manually edited to contain the sequences of BSA internal standard. Database searching was performed on the Sorcerer 2, using the TPP. Statistical analysis of the data was performed using standard statistical tools.

Filter Paper Assay (FPU2% Assay)

Cellulase activity was measured in term of "filter paper units" (FPU) per milliliter in a Filter Paper Unit assay (FPU assay) of original (undiluted) enzyme solution. The method was modified from the analytical procedure of Adney and Baker (1996, MoA Laboratory Analytical Procedures-006 entitled: Measurement of cellulase activities by Adney and Baker (1996) www.nrel.gov/biomass/analytical_procedures.html) to be more sensitive than the standard method that is based on International Union of Pure and applied chemistry (IUPAC) guidelines. For quantitative results the enzyme compositions were compared on the basis of significant and equal conversions. The value of 1.0 mg of reducing sugar as glucose from 50 mg of filter paper (2% conversion instead of the international standard of 4%) in 60 minutes was designated as the intercept for calculation filter paper units (FPU) by IUCA. In this procedure, reducing sugar yield is not a linear function of the quantity of enzyme in the assay mixture, twice the amount of enzyme will not be expected to yield twice the amount of reducing sugar in equal time. The assay procedure therefore involved finding a dilution of the original enzyme stock such that a 0.5 ml aliquot of the dilution will catalyze 2% conversion in 60 minutes, and then calculating the activity (in FPU2%/ml) of the original stock from the dilution required.

FPU was calculated using the following formula:

$$\text{Filter paper activity} = 0.37/([\text{Enzyme}] \text{ releasing } 1.0 \text{ mg glucose}) \text{ [Units/ml]}$$

[Enzyme] represents the proportion of the original enzyme solution present in the directly tested enzyme dilution.

Batch Fermentation

Inoculation Procedure:

The content of one vial was added to a pre-culture medium: baffled 2 L-shake flask [20 g/L yeast extract, 20 g/L glucose, pH 6.8 (with KOH), 300 mL medium, steamsterilized 20 min at 121° C.]. Pre-culture was grown for 24-48 h at 48° C. and 200 rpm. Timing can be adapted to the shake flask configuration and the vial viability.

Main Fermentation Procedure:

The medium was composed of a mix of grain flour (3%), cellulose (6%), a nitrogen source (2.5%; examples of nitrogen sources known in the art include soy bean meal, yeast extract, corn steep liquor, ammonia, ammonium salts, nitrate salts.), as well as a salt fraction. The salt fraction was fitting with WO98/37179, Table 1, p. 12. Deviations from this table were: $CaCl_2.2aq$ 1.0 g/L, KCl 1.8 g/L citric acid.1aq 0.45 g/L (chelating agent). The medium was steam-sterilized in one fraction. Bioreactors were inoculated at ~10% inoculum ratio and the working volume was 10 L. Process pH was controlled between 5.0-3.0 (using phosphoric acid and ammonia), while temperature at 42-52° C.

Airflow was maintained between 0.5 and 1.5 vvm (volume air per volume broth per minute) and the DOT above 30% of the oxygen saturation before inoculation with the aim of agitation. Clerol was used as antifoam on a periodic manner: 2 sec. every 30 min. for the first 24 h, then 2 sec. every hour later on.

At the end of the pre-culture phase samples were taken for contamination check, glucose determination and pH measurement. During the main fermentation, samples were taken every 24 h and the following analysis were performed: contamination control, pH measurement, SDS-PAGE gels, total protein concentration determination (TCA Biuret method), and Filter Paper Unit activity (FPU2%/ml), as described above.

Example 7

Fermentation of *Talaromyces emersonii* Transformant Overexpressing Multiple Cellulases This example describes the fermentation of *T. emersonii* transformants.

Two primart transformants described in EXAMPLE 5, Transformant 20 (EBAT142-1) and transformant 64 (EBAT147-1), and one secondary transformant of EXAMPLE 6, EBAT147-2, were tested in 10-liter production fermentor as batch fermentation under cellulase inducing conditions. As controls, the empty FBG-142 and FBG-147 strains were tested.

At the end of fermentation, TCA-Biuret and cellulase activity (FPU) were determined (Table 4).

TABLE 4

Results of TCA-biuret and FPU activity measurement of supernatants of *T. emersonii* transformants and empty host strains grown in 10-liter production fermentor.

| Strain | Time (h) | TCA Biuret protein (mg/ml) | $FPU_{2\%}$/ml | Specific activity of mix (FPU/mg) |
|---|---|---|---|---|
| FBG-142 | 97 | 16.4 | 15.8 | 0.96 |
| EBAT142-1 | 93 | 15.7 | 20.9 | 1.33 |
| FBG-147 | 95 | 17.4 | 17.3 | 0.99 |
| EBAT147-1 | 93 | 19.1 | 21.6 | 1.13 |
| EBAT147-2 | 93 | 19.9 | 25 | 1.26 |

The results clearly show that *T. emersonii* transformants showed enhanced cellulase activity compared to empty host strains. Transformant EBAT142-1, expressing all four cellulases (strain 20 in FIG. 9), showed a 1.32-fold improvement in cellulase activity compared to the empty host FBG-142. Transformant EBAT147-1, expressing three cellulases (strain 64 in FIG. 9), showed a 1.25-fold improvement in cellulase activity compared to the empty host FBG-147. The secondary transformant, EBAT147-2, in which GBH and BG levels were further increased compared to the host strain EBAT147-1 and in which acetyl xylan esterase was overexpressed (see EXAMPLE 8), showed a further improvement in cellulase activity: EBAT147-2 produced 1.16-fold more cellulase activity compared to the parental strain EBAT147-1 and a 1.44-fold improvement compared to the empty host strain FBG-147.

In addition, the cellulase activity per mg of protein was increased in transformants compared to the empty host strain. In the empty host strain <1 FPU/mg protein was observed, whereas the primary transformants all showed >1.1 FPU/mg protein. The secondary transformant EBAT147-2 also showed a further 1.11-fold improvement in cellulase activity per mg of protein compared to the primary transformant EBAT147-1. All together, the results suggest that the fraction of cellulases in the supernatant of transformants is increased.

The experiment strongly indicates that it is possible to enhance cellulase activity on top of the endogenous cellulase production by *T. emersonii* by overexpressing *T. emersonii* cellulases. In addition, a second transformation of an improved transformant showed a further increase in cellulase activity.

Example 8

Analysis of *Talaromyces emersonii* Transformants Overexpressing Multiple Cellulases by Proteomics This example describes the characterization of primary transformant EBAT147-1 and secondary transformant EBAT147-2 for increased levels of overexpressed cellulases as determined by proteomics.

Supernatants of 10-liter batch fermentations of FBG-147 and transformant EBAT147-1 and EBAT147-2 (see EXAMPLE 7) were analysed using APEX proteomics analysis. The relative amount of cellulases, hemicellulases and accessory proteins are shown in Table 5.

TABLE 5

Comparison of the relative cellulase levels (APEX) of *T. emersonii* strain FBG-147 and the primary transformant EBAT147-1 and secondary transformant EBAT147-2.
Expressed in % of total protein as determined by APEX.

| Enzyme/Protein | FBG-147 | EBAT147-1 | EBAT147-2 |
|---|---|---|---|
| CBH I | 8.0 ± 0.4 | 12.5 ± 1.0* | 16.3 ± 4.7* |
| CBH II | 7.3 ± 1.2 | 8.5 ± 2.0 | 7.7 ± 3.2 |
| EG | 1.5 ± 0.7 | 1.4 ± 0.7 | 1.0 ± 0.6 |
| EG/CEA | 3.0 ± 0.9 | 5.6 ± 0.8* | 5.0 ± 0.9* |
| EG/CEB | 2.1 ± 0.9 | 2.1 ± 1.1 | 2.1 ± 0.1 |
| BG | 0.9 ± 0.1 | 1.5 ± 0.0* | 2.4 ± 0.3‡ |
| Xylanase | 3.5 ± 0.1 | 3.2 ± 0.5 | 2.7 ± 0.5 |
| Acetyl xylan esterase | 11.1 ± 3.7 | 5.3 ± 3.2 | 12.6 ± 4.3‡ |
| EG/Family 61 | 8.6 ± 1.5 | 9.5 ± 6.5 | 8.1 ± 1.9 |
| Swollenin-like protein | 1.4 ± 0.4 | 1.0 ± 0.4 | 1.0 ± 0.2 |
| Unknown protein | 3.4 ± 1.5 | 3.3 ± 1.3 | 3.9 ± 0.8 |
| Total I[b] | 36 ± 1 | 40 ± 6.7 | 48 ± 1.8* |
| Total II[c] | 51 ± 3 | 54 ± 3.8 | 63 ± 5.7* |
| Protease | 1.8 ± 0.3 | 1.1 ± 1.7 | n.d |
| Chitinase | 0.4 ± 0.2 | 0.3 ± 0.4 | 0.1 ± 0.1 |
| $FPU_{2\%}$/ml | 17.3 | 21.6 | 25 |

[a]Supernatants from approximately 95 hr 10-liter Eschweiler batch fermentations were subjected to APEX analysis. All values are expressed in percentages of the proteins detected. Values with an asterisk indicate levels that change statistically significantly between FBG-147 and the descendent strains (p-value ≤0.05 in Student's T-test, 2-sided, unequal variance). Values highlighted with a ‡ indicate levels that change statistically significantly between EBAT147-1 and the descendent strain (p-value ≤0.05 in Student's T-test, 2-sided, unequal variance). TEC levels as FPU2%/ml from batch fermentations is shown at the bottom.
[b]Total cellulase content (as determined by APEX, expressed as % of protein detected by APEX proteomics analysis): sum of CBH I, CBH II, EG, EG/CEA, EG/CEB, BG, EG/family 61 (as described in European Patent application EP10167771.4), swollenin-like protein (as described in European Patent application EP10167764.9) and unknown protein (as described in European Patent application EP10167767.2), listed in Table 5.
[c]Total cellulases and xylanases content (as determined by APEX, expressed as % of protein detected by APEX proteomics analysis): Total cellulase (% of protein detected by APEX proteomics analysis) as defined above in [b] + xylanase + acetyl xylan esterase, listed in Table 5.

The results clearly show that 3 cellulases were significantly overexpressed in transformant EBAT147-1 compared to FBG-147: CBHI expressed from plasmid pGBTOPEBA205, EG/CEA expressed from plasmid pGBTOPEBA8, and BG expressed from plasmid pGBTOPEBA4. Levels of endogenous proteins were not significantly different between EBAT147-1 and FBG-147.

In secondary transformant EBAT147-2, CBHI expressed from plasmid pGBTOPEBA205 and BG expressed from plasmid pGBTOPEBA4 were further enhanced compared to primary transformant EBAT147-1, and, in addition, acetyl xylan esterase expressed from plasmid pGBFINEBA193 was overexpressed.

The total cellulase content listed in Table 5 showed that the fraction of cellulases in the total amount of detected protein is increased in transformants.

The experiment strongly indicates that *T. emersonii* cellulases can be overexpressed by transformation of *T. emersonii* with multiple expression cassettes encoding cellulases and levels of cellulases can be further enhanced by a second transformation of a primary transformant. The results explain the improvement in cellulase activity of the transformants described in EXAMPLE 6. In addition, the fraction of cellulases in the amount of total secreted protein produced by *T.* *emersonii* can be improved by overexpressing cellulases, which is in agreement with the improved cellulase activity per mg of protein observed in transformants (EXAMPLE 6).

The invention claimed is:

1. A process for production of a *Talaromyces emersonii* transformant, said process comprising the steps of:
    (a) providing one or more expression cassettes comprising at least one polynucleotide encoding cellulose, hemicellulase, and/or pectinase, and at least one promoter for expression of said polynucleotide;
    (b) providing a selection marker included in the expression cassette of (a) and/or included in a dedicated selection marker polynucleotide;
    (c) transfecting a *Talaromyces emersonii* host which endogenously produces cellulase and/or hemicellulase with the at least one expression cassette from (a) and the selection marker from (b);
    (d) selecting the *Talaromyces emersonii* transformant which comprises said at least one expression cassette from (a) and the selection marker from (b); and
    (e) isolating said *Talaromyces emersonii* transformant.

2. A *Talaromyces emersonii* transformant obtained by the process of claim 1, wherein said expression cassette comprises a polynucleotide encoding cellulase, wherein the endogenous and exogenous cellulase expressed from said transformant has a cellulase activity of 2 wheat straw units per milliliter (WSU/ml) or more in 16 times or more diluted supernatant or broth.

3. The *Talaromyces emersonii* transformant according to claim 2, having a cellulase activity of 3 wheat straw units per milliliter (WSU/ml) or more in 16 times or more diluted supernatant and/or broth.

4. The *Talaromyces emersonii* transformant according to claim 2, said cellulase having an endoglucanase activity of 50 WBCU/ml or more, where WBCU is the amount of cellulase that hydrolyses in one hour a number of glycosidic bonds equivalent to the production of 0.5 mg glucose under assay conditions.

5. The *Talaromyces emersonii* transformant according to claim 2, said transformant comprising 2 or more expression cassettes comprising a polynucleotide encoding cellulase.

6. The *Talaromyces emersonii* transformant according to claim 5, wherein the encoded cellulase is selected from the group consisting of cellobiohydrolase, endoglucanase, and beta-glucosidase.

7. The *Talaromyces emersonii* transformant according to claim 6, wherein said cellobiohydrolase is cellobiohydrolase I and/or cellobiohydrolase II.

8. The *Talaromyces emersonii* transformant according to claim 2, wherein at least one polynucleotide encoding cellulase, hemicellulose, and/or pectinase found in the expression cassette is integrated into the genome of said *Talaromyces* transformant.

9. The *Talaromyces emersonii* transformant according to claim 2, wherein said selection marker of (b) is deleted from said *Talaromyces emersonii* transformant.

10. A process for production of a polypeptide composition comprising at least one cellulase, hemicellulase, and/or pectinase comprising the steps of:
    (a) providing one or more expression cassettes comprising at least one polynucleotide encoding cellulase, hemicellulase, and/or pectinase, and at least one promoter for expression of said polynucleotide;
    (b) providing a selection marker included in the expression cassette of (a) and/or included in a dedicated selection marker polynucleotide;
    (c) transfecting a *Talaromyces emersonii* host with the at least one expression cassette from (a) and/or the selection marker from (b);
    (d) selecting the *Talaromyces emersonii* transformant which comprises said at least one expression cassette from (a) and the selection marker from (b); and
    (e) producing the polypeptide composition comprising cellulase, hemicellulase, and/or pectinase by culturing the *Talaromyces emersonii* transformant in a suitable culture medium in which a cellulase inducer is substantially absent; and
    (f) recovering the polypeptide composition comprising cellulase, hemicellulase, and/or pectinase.

11. The process according to claim 10, wherein in (a), two or more expression cassettes are provided.

12. The process according to claim 10, wherein said promoter is selected from the group consisting of: promoters of *A. niger* glaA, *A. nidulans* gpd promoters, or functional parts thereof, said promoter optionally preceded by an upstream activating sequence.

13. The process according to claim 12, wherein said promoter is the *A. niger* glaA promoter or a functional part thereof, said promoter optionally preceded by an upstream activating sequence.

14. The process according to claim 10, wherein said selection marker is selected from the group consisting of amdS (acetamidase), hygB (hygromycin phosphotransferase) and ble (phleomycin resistance).

15. The process for saccharification of lignocellulosic material, said process comprising contacting said material with the *Talaromyces emersonii* transformant according to claim 2.

16. A process for production of *Talaromyces emersonii* multiple transformant comprising:
  (a) providing the isolated *Talaromyces emersonii* transformant of claim 2;
  (b) providing one or more expression cassettes comprising at least one polynucleotide encoding cellulase, hemicellulase, and/or pectinase, and at least one promoter for expression of said polynucleotide;
  (c) providing a selection marker included in the expression cassette of (b) and/or included in a dedicated selection marker polynucleotide;
  (d) transfecting the *Talaromyces emersonii* host of (a) with the at least one expression cassette from (b) and the selection marker from (c);
  (e) selecting the *Talaromyces emersonii* transformant which comprises said at least one expression cassette from (b) and the selection marker from (c); and
  (e) isolating said *Talaromyces emersonii* transformant, and
  (f) optionally repeating steps (a)-(e), using the isolated *Talaromyces emersonii* transformant of (e) in place of the isolated *Talaromyces emersonii* transformant of (a).

17. The process according to claim 16, wherein in said first transformation a different selection marker is used than in said second transformation.

* * * * *

UNITED STATES PATENT AND TRADEMARK OFFICE
CERTIFICATE OF CORRECTION

PATENT NO. : 8,802,415 B2  Page 1 of 1
APPLICATION NO. : 13/505697
DATED : August 12, 2014
INVENTOR(S) : Los et al.

It is certified that error appears in the above-identified patent and that said Letters Patent is hereby corrected as shown below:

In the Claims

Col. 91, line 62, Claim 4,
"qlycosidic" should be changed to <u>glycosidic</u>

Col. 92, line 39, Claim 8,
"hemicellulose" should be changed to <u>hemicellulase</u>

Col. 93, line 16, Claim 15,
"The process" should be changed to <u>A process</u>

Col. 93, line 20, Claim 16,
"of *Talaromyces*" should be changed to <u>of a *Talaromyces*</u>

Signed and Sealed this
Sixteenth Day of December, 2014

Michelle K. Lee
*Deputy Director of the United States Patent and Trademark Office*